United States Patent
Lattemann et al.

(10) Patent No.: US 10,550,397 B2
(45) Date of Patent: Feb. 4, 2020

(54) METHOD FOR PRODUCING RECOMBINANT 11-DE-O-METHYLTOMAYMYCIN

(71) Applicant: Sanofi, Paris (FR)

(72) Inventors: Claus Lattemann, Frankfurt am Main (DE); Mark Broenstrup, Frankfurt am Main (DE); Stefan Werner, Saarbrücken (DE); Rolf Müller, Blieskastel (DE); Kirsten Harmrols, Saarbrücken (DE)

(73) Assignee: SANOFI, Paris (FR)

( * ) Notice: Subject to any disclaimer, the term of this patent is extended or adjusted under 35 U.S.C. 154(b) by 709 days.

(21) Appl. No.: 14/401,109

(22) PCT Filed: May 13, 2013

(86) PCT No.: PCT/EP2013/059810
§ 371 (c)(1),
(2) Date: Nov. 13, 2014

(87) PCT Pub. No.: WO2013/171157
PCT Pub. Date: Nov. 21, 2013

(65) Prior Publication Data
US 2015/0111298 A1    Apr. 23, 2015

(30) Foreign Application Priority Data
May 14, 2012    (EP) .................................... 12305529

(51) Int. Cl.
*C12N 15/76*    (2006.01)
*C07K 14/36*    (2006.01)

(52) U.S. Cl.
CPC .............. *C12N 15/76* (2013.01); *C07K 14/36* (2013.01)

(58) Field of Classification Search
None
See application file for complete search history.

(56) References Cited

U.S. PATENT DOCUMENTS

2007/0117113 A1    5/2007    Farnet et al.

FOREIGN PATENT DOCUMENTS

FR    1516743    3/1968

OTHER PUBLICATIONS

Li, W. et al. GenBank Accession No. FJ768957.1, Apr. 2009, partial listing (including the sequence of the S. achromogenes tomA gene).*
Baltz, R.H. J. Ind. Microbiol. Biotechnol. 37:759 (2010).*
Bibb et al., "The mRNA for the 23S rRNA methylase encoded by the ermE gene of Saccharopolyspora erythraea is translated in the absence of a conventional ribosome-binding site," Mol Microbiol. 14(3):533-45 (1994).
Arima et al., "Studies on tomaymycin, a new antibiotic. I. Isolation and properties of tomaymycin," J Antibiot. 25(8):437-44 (1972).

(Continued)

*Primary Examiner* — Diana B Johannsen
(74) *Attorney, Agent, or Firm* — McDonnell Boehnen Hulbert & Berghoff LLP

(57) ABSTRACT

The present invention provides a tomaymycin biosynthetic gene cluster of *Streptomyces* species FH6421, and its use for producing 11-de-O-methyltomaymycin.

10 Claims, 5 Drawing Sheets

Specification includes a Sequence Listing.

(56) References Cited

OTHER PUBLICATIONS

Bibb et al., "Cloning and analysis of the promoter region of the erythromycin resistance gene (ermE) of Streptomyces erythraeus," Gene. 38(1-3):215-26 (1985).
Bierman et al., "Plasmid cloning vectors for the conjugal transfer of DNA from *Escherichia coli* to *Streptomyces* spp.," Gene. 116(1):43-9 (1992).
Choulet et al., "Intraspecific variability of the terminal inverted repeats of the linear chromosome of Streptomyces ambofaciens," J Bacteriol. 188(18):6599-610 (2006).
Fernandez-Moreno et al., "The act cluster contains regulatory and antibiotic export genes, direct targets for translational control by the bldA tRNA gene of Streptomyces," Cell. 66(4):769-80 (1991).
Herai et al., "Hyper-inducible expression system for streptomycetes," Proc Natl Acad Sci U S A. 101(39):14031-5 (2004).
Li et al., "Cloning and characterization of the biosynthetic gene cluster for tomaymycin, an SJG-136 monomeric analog," Appl Environ Microbiol. 75(9):2958-63 (2009).
Murakami et al., "Thiostrepton-induced gene expression in Streptomyces lividans," J Bacteriol. 171(3):1459-66 (1989).
Nishioka et al., "Mode of action of tomaymycin," J Antibiot. 25(11):660-7 (1972).
Takano et al., "Construction of thiostrepton-inducible, high-copy-number expression vectors for use in *Streptomyces* spp," Gene. 166(1):133-7 (1995).
Wehmeier et al., "New multifunctional *Escherichia coli*-Streptomyces shuttle vectors allowing blue-white screening on XGal plates," Gene. 165(1):149-50 (1995).
International Preliminary Report on Patentability issued by the International Bureau for International Application No. PCT/EP2013/059810, dated Nov. 18, 2014 (pp. 1-6).
International Search Report of the International Searching Authority for International Application No. PCT/EP2013/059810, dated Jun. 28, 2013 (pp. 1-3).
Written Opinion of the International Searching Authority for International Application No. PCT/EP2013/059810, dated Jun. 28, 2013 (pp. 1-5).

\* cited by examiner

METHOD FOR PRODUCING RECOMBINANT 11-DE-O-METHYLTOMAYMYCIN

This application is a national stage application under 35 U.S.C. § 371 of International Application No. PCT/EP2013/059810, filed May 13, 2013, which claims the benefit of European Patent Application No. 12305529.5 filed on May 14, 2012, the disclosures of each of which are explicitly incorporated by reference herein.

FIELD OF THE INVENTION

The present invention relates to a method for recombinantly producing the antibiotic 11-de-O-methyltomaymycin, as well as to nucleic acids coding for the tomaymycin biosynthetic gene cluster.

BACKGROUND

Tomaymycin is a naturally occurring antibiotic having, besides its anti-bacterial effectiveness, cytotoxic and antitumor activity. Tomaymycin belongs to the chemical group of pyrrolobenzodiazepines (PBD), which are monomeric compounds with weak antibiotic properties that specifically alkylate the minor groove of DNA at a 5'-Pu-G-Pu base sequence. Tomaymycin was isolated from the culture filtrate of *Streptomyces achromogenes* var. *tomaymyceticus* by K. Arima (Arima et al., 1972; Nishioka et al., 1972). It was found that tomaymycin is synthesized by a series of proteins that are encoded by a set of genes clustered within a gene cluster. The biosynthetic gene cluster for tomaymycin has been elucidated by Li et al. (Li et al., 2009). Tomaymycin has proven active against tumours in mice, such as sarcoma 180; the benzpyrene sarcoma; the mamma tumor; or leukosarcomatosis such as leukosarcomatosis AKR or $C_{1498}$ or against leukemia, plasmacytoma and ovarian cancer cell lines. Tomaymycin has the structural formula presented in FIG. 1(A). 11-de-O-methyltomaymycin has the empirical formula $C_{15}H_{18}N_2O_4$ and a molecular weight of 290.32. The structural formula of 11-de-O-methyltomaymycin is shown in FIG. 1(B). The tomaymycin-urea adduct is shown in FIG. 1(C).

Whereas 11-de-O-methyltomaymycin is produced during natural biosynthesis, tomaymycin is produced artificially therefrom by addition of methanol during the isolation/purification process (cf. FIG. 1).

FR 1.516.743 discloses a method for the production of tomaymycin using chromatography of a solution comprising the antibiotic adsorbed to an adsorbens, countercurrent distribution, preparation of a complex with urea and regeneration of the antibiotic from the medium comprising the complex. The medium for culturing the strain producing tomaymycin contained usual nutrients, such as an assimilable carbon and nitrogen sources, minerals and optionally growth factors. Assimilable nitrogen sources comprise, for example, nitrate, anorganic or organic ammonium salts, urea or amino acids or substances comprising nitrogen in protidic form, such as casein, soybean flour or distillers' solubles. However, none of the media indicated in FR 1.516.743 resulted in the production of high, satisfactory yields of tomaymycin.

Therefore, there is a need in the art for a method for producing high amounts of tomaymycin. This problem is solved by the present invention.

SUMMARY OF THE INVENTION

Embodiments of the invention provide a nucleic acid molecule comprising at least one nucleic acid selected from the group consisting of: (a) a nucleic acid comprising at least one of the Open Reading Frames (ORFs) 1 to 19 of SEQ ID NO: 2 that encodes proteins of SEQ ID NOs: 4 to 22 or a variant or fragment thereof, whereby the variant or fragment encodes a functionally active variant or fragment of a protein of SEQ ID NOs: 4 to 22, (b) a nucleic acid encoding at least one of the proteins of SEQ ID NOs: 4 to 22 or a functionally active variant or fragment thereof, (c) a nucleic acid encoding a protein that is at least 70%, 80%, 90%, 95% or 97% identical in amino acid sequence to a protein or fragment thereof encoded by the nucleic acid of (a) or (b), (d) a nucleic acid that hybridizes under stringent conditions with a nucleic acid of (a) to (c), (e) a nucleic acid that is complementary to a nucleic acid of (a) to (d). In certain embodiments, the nucleic acid comprises the tomaymycin biosynthetic gene cluster of SEQ ID NO: 2 or a variant or fragment sequence of SEQ ID NO: 2 harboring a variant or fragment of at least one of ORFs 1 to 19, whereby the variant or fragment encodes a functionally active variant or fragment of a protein of SEQ ID NOs: 4 to 22.

Another embodiment of the invention provides an expression vector comprising any of the above nucleic acids.

Yet another embodiment of the invention provides a cell comprising the above expression vector. In a specific embodiment, the cell is *Streptomyces* species FH6421.

An embodiment of the invention provides a method for producing a cell that harbors a tomaymycin biosynthetic gene cluster or a functionally active variant or fragment thereof. In certain embodiments, the cell harbors the tomaymycin biosynthetic gene cluster of SEQ ID NO: 1, SEQ ID NO: 2, or SEQ ID NO: 3, or a functionally active variant or fragment thereof. In other specific embodiment, the cell is a *Streptomyces* strain harboring the tomaymycin biosynthetic gene cluster of SEQ ID NO: 1, SEQ ID NO: 2, or SEQ ID NO: 3, or a functionally active variant or fragment thereof. In yet other specific embodiments, the *Streptomyces* strain is selected from the group consisting of *Streptomyces achromogenes* var. *tomaymyceticus*, *Streptomyces* species FH6421, and *Streptomyces albus*/pStW102tc. In further specific embodiments, the cell harbors at least one ORF of SEQ ID NO: 1, SEQ ID NO: 2, or SEQ ID NO: 3, or functionally active variant or fragment thereof, and is capable of producing 11-de-O-methyltomaymycin.

*albus* J1074 pStW102tcΔCG culture without feeding (grey) and feeding with 2-amino-5-bromobenzoic acid (black). Mass spectra of the obtained substances and deviations to the theoretical mass are displayed below the respective structure. D) Structure of fed (S)-4-methylenepyrrolidine-2-carboxylic acid and proposed structures for resulting mutasynthesis products, E) Extracted ion chromatogram (C14H17N2O4+: 277.11828 Da±5 ppm; C14H15N2O4+: 275.10263 Da±5 ppm) of *Streptomyces albus* J1074 pStW102tcΔHI culture without feeding (grey) and feeding with (S)-4-methylenepyrrolidine-2-carboxylic acid (black). Mass spectra of the obtained substances and deviations to the theoretical mass are displayed below the respective structure.

Figure 5A:
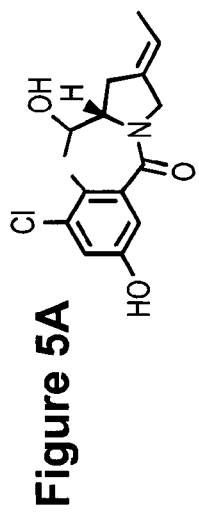
Figure 5B:
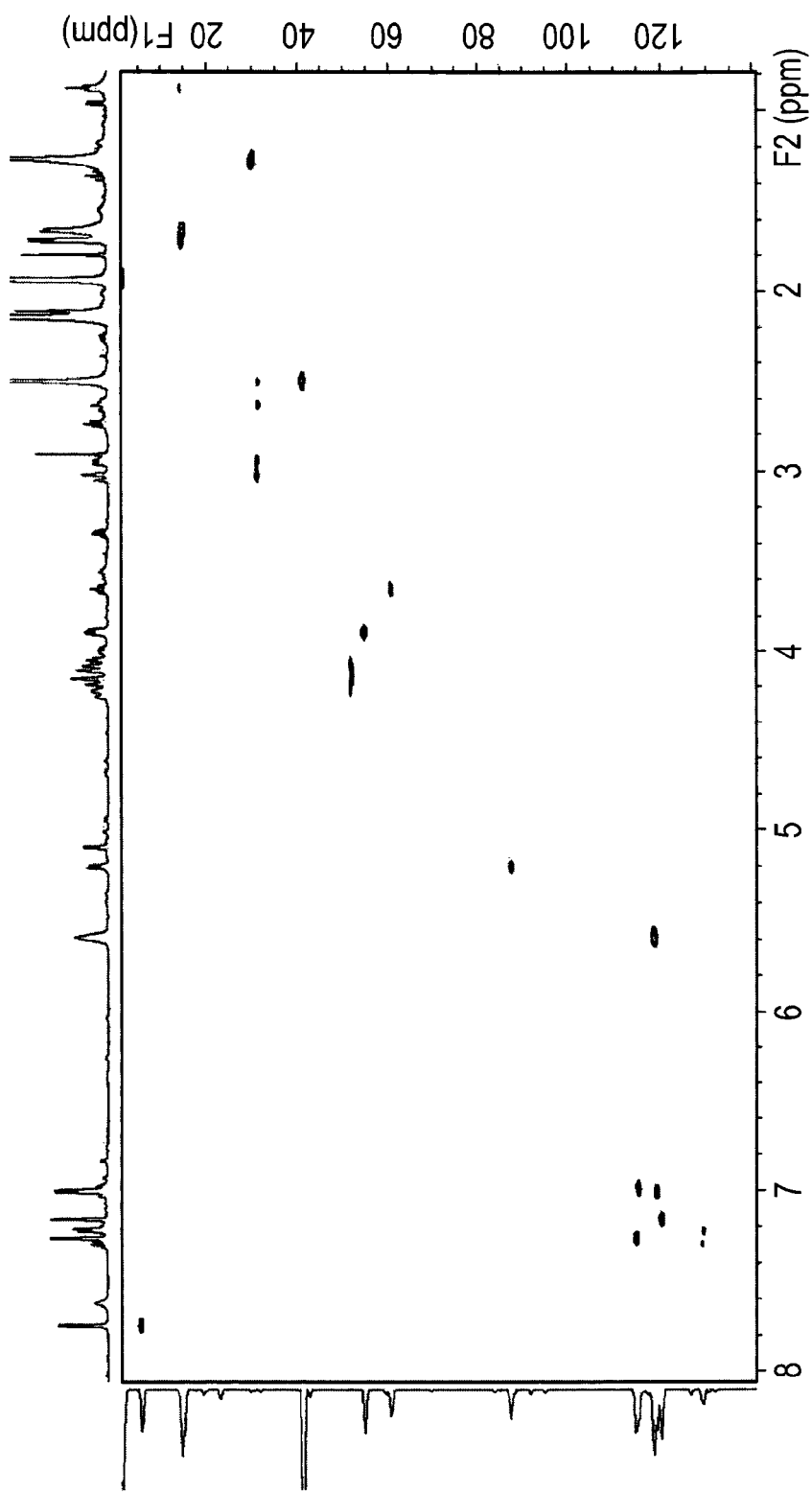

FIG. 5 is a presentation of A) Structure of 9-chloro-11-de-O-methyl-8-deshydroxy-7-hydroxytomaymycin (CDHT); B) 1H,13C-HSQC-spectrum of CDHT.

DETAILED DESCRIPTION

In one embodiment, a nucleic acid is provided comprising at least one nucleic acid selected from:
(a) a nucleic acid comprising at least one of the Open Reading Frames (ORFs) 1 to 19 as comprised by SEQ ID NO: 2 that encodes proteins of SEQ ID NOs: 4 to 22 or a variant or fragment thereof, whereby the variant or fragment encodes a functionally active variant or fragment of a protein of SEQ ID NOs: 4 to 22,
(b) a nucleic acid encoding at least one of the proteins of SEQ ID NOs: 4 to 22 or a functionally active variant or fragment thereof,
(c) a nucleic acid encoding a protein that is at least 70%, 80%, 90%, 95% or 97% identical in amino acid sequence to a protein or fragment thereof encoded by the nucleic acid of (a) or (b),
(d) a nucleic acid that hybridizes under stringent conditions with a nucleic acid of (a) to (c),
(e) a nucleic acid that is complementary to a nucleic acid of (a) to (d).

In another embodiment, the nucleic acid comprises or consists of the tomaymycin biosynthetic gene cluster having the sequence of SEQ ID NO: 2 or a variant or fragmental sequence of SEQ ID NO: 2 harboring a variant or fragment of at least one of ORFs 1 to 19, whereby the variant or fragment encodes a functionally active variant or fragment of a protein of SEQ ID NOs: 4 to 22.

In a further embodiment an expression vector is provided comprising a nucleic acid of the embodiments mentioned above.

In yet another embodiment, a cell comprising a nucleic acid is provided according to the embodiments outlined above, or a cell transformed with the expression vector according to above embodiment. Preferably the cell is *Streptomyces* species FH6421.

Another embodiment is directed to the method for producing a cell wherein the cell harbors a tomaymycin biosynthetic gene cluster or a functionally active variant or fragment thereof.

In a further embodiment, the method produces a cell that harbors the tomaymycin biosynthetic gene cluster of SEQ ID NO: 1, SEQ ID NO: 2, or SEQ ID NO: 3, or a functionally active variant or fragment thereof.

In another embodiment, the method produces a cell that is a *Streptomyces* strain harboring the tomaymycin biosynthetic gene cluster of SEQ ID NO: 1, SEQ ID NO: 2, or SEQ ID NO: 3, or a functionally active variant or fragment thereof.

In yet another embodiment, the method produces a *Streptomyces* strain that is selected from *Streptomyces achromogenes* var. *tomaymyceticus, Streptomyces* species FH6421, and *Streptomyces albus.*

In yet a further embodiment, the method produces a cell that harbors at least one ORF of SEQ ID NO: 1, SEQ ID NO: 2, or SEQ ID NO: 3, or functionally active variants or fragments thereof, and is capable of producing 11-de-O-methyltomaymycin.

Thus, in sum, the present invention relates to a method for producing a cell, wherein the cell harbors a tomaymycin biosynthetic gene cluster or a functionally active variant or fragment thereof. Preferably the cell harbours the tomaymycin biosynthetic gene cluster of SEQ ID NO: 1, SEQ ID NO: 2, or SEQ ID NO: 3, or a functionally active variant or fragment thereof. Preferably, the cell is a *Streptomyces* strain harbouring the tomaymycin biosynthetic gene cluster of SEQ ID NO: 1, SEQ ID NO: 2, or SEQ ID NO: 3, or a functionally active variant or fragment thereof, in particular *Streptomyces achromogenes* var. *tomaymyceticus, Streptomyces* species FH6421.

Alternatively, the cell harbours at least one, at least two, at least three, at least four, or at least five ORFs as comprised by SEQ ID NO:1, SEQ ID NO: 2, or SEQ ID NO: 3, or functionally active variants or fragments thereof, and is capable of producing 11-de-O-methyltomaymycin.

The term "cell producing 11-de-O-methyltomaymycin" is, in principle, any cell that produces 11-de-O-methyltomaymycin. Herein, the terms "cell" and "cell producing 11-de-O-methyltomaymycin" are used interchangeably. 11-de-O-methyltomaymycin is a secondary metabolite of the class of pyrrolobenzodiazepines (PBD) and is naturally produced by the genus *Streptomyces* of the order Actinomycetales. In particular, 11-de-O-methyltomaymycin is naturally produced by microorganisms of the genus *Streptomyces achromogenes*, especially the strain *Streptomyces achromogenes* var. *tomaymyceticus.* All of these cells are comprised by the present invention.

Particularly included herein are cells that produce 11-de-O-methyltomaymycin and harbor a tomaymycin biosynthetic gene cluster, such as, e.g., the nucleic acid sequence of SEQ ID NO:1, SEQ ID NO: 2, or SEQ ID NO: 3, so that they effectively produce 11-de-O-methyltomaymycin. Included herein are cells that do not naturally produce 11-de-O-methyltomaymycin, but that have been transformed with a tomaymycin biosynthetic gene cluster, such as SEQ ID NO:1, SEQ ID NO: 2, or SEQ ID NO: 3. The above mentioned embodiments may also be combined. For example, the cell may be transformed with a tomaymycin biosynthetic gene cluster, such as, e. g., comprised by SEQ ID NO:1, SEQ ID NO: 2, or SEQ ID NO: 3, and the tomaymycin biosynthetic gene cluster is mutagenized, e.g., in order to enhance the productivity of 11-de-O-methyltomaymycin by the cell.

Figure 1:
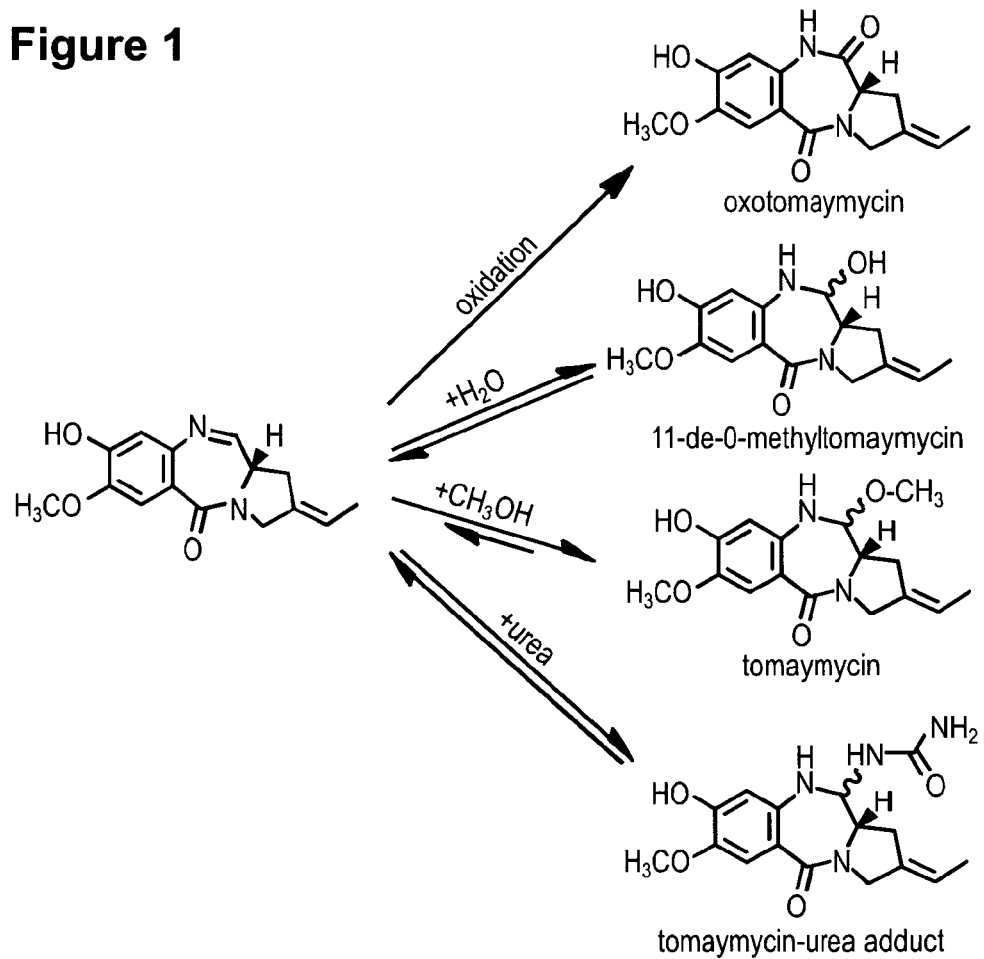
FIG. 1 is s schematic drawing of the chemical relationship between oxotomaymycin, 11-de-O-methyltomaymycin, tomaymycin, and the tomaymycin-urea adduct.
Figure 2:
FIG. 2 is a schematic drawing of the tomaymycin biosynthetic gene cluster of strain *Streptomyces* species FH6421. The designations "orfX0" and "orfX1" and "A" to "Q" denote ORFs or genes, as listed in Table 1, whereby "A" to "Q" stand for "tomA" to "tomQ".
Figure 3:
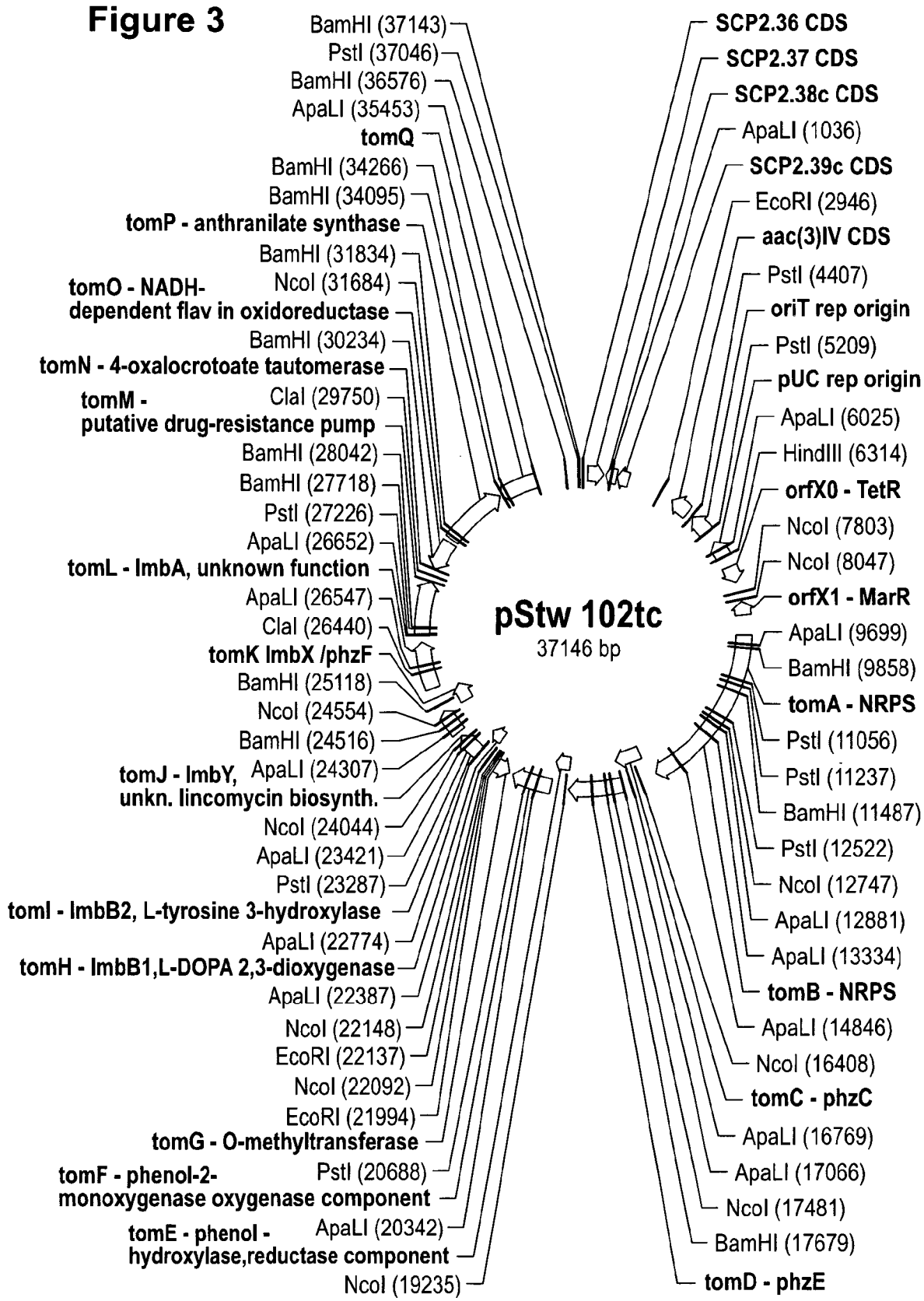
FIG. 3 is a presentation of pSTW102tc, which is the plasmid into which the tomaymycin biosynthetic gene cluster of strain *Streptomyces* species FH6421 is inserted. The ORFs or genes constituting the gene cluster as well as the respective putative proteins are indicated. Moreover, cleavage sites for restriction enzymes and their location are included.

Moreover, the present inventors succeeded in identifying the tomaymycin biosynthetic gene cluster of strain *Streptomyces* species FH6421 that is comprised herein by the nucleic acid sequences of SEQ ID NO: 2 (tomaymycin biosynthetic gene cluster of strain *Streptomyces* species FH6421) or SEQ ID NO: 3 (plasmid pSTW102tc into which the tomaymycin biosynthetic gene cluster of strain *Streptomyces* species FH6421 is inserted). FIG. 2 schematically shows the tomaymycin biosynthetic gene cluster of strain *Streptomyces* species FH6421. FIG. 3 shows the plasmid pSTW102tc, into which the tomaymycin biosynthetic gene cluster of strain *Streptomyces* species FH6421 is inserted.

In the context of the present invention, the term "gene cluster" is a nucleic acid and refers to a set of several genes or ORFs that are located on a contiguous stretch of the genome and that participate in the synthesis of 11-de-O-methyltomaymycin. The encoded proteins are either enzymes that catalyse reactions of substrates into products, or are involved in regulation of the synthesis of 11-de-O-methyltomaymycin or intermediate products or the transport of 11-de-O-methyltomaymycin or intermediate products. Li et al. (2009) have assigned, by homology to known genes, specific functions to the proteins encoded by the ORFs. Altogether, the genes as comprised by the gene cluster encode proteins involved in the biosynthesis of 11-de-O-methyltomaymycin.

The term "tomaymycin biosynthetic gene cluster" refers to the tomaymycin biosynthetic gene cluster as comprised by *Streptomyces* species FH6421, which has been cloned and sequenced by the present inventors. The sequence is shown in SEQ ID NO: 2. The sequence of the tomaymycin biosynthetic gene cluster has been cloned into the vector pStW102 (derived from pOJ446), resulting in pSTW102tc, which is presented herein as SEQ ID NO: 3. A schematic drawing of pSTW102tc is shown in FIG. 3. The following ORFs were identified within the gene cluster: orfX0, orfX1, tomA, tomb, tomC, tomD, tome, tomF, tomG, tomI, tomJ, tomK, tomL, tomM, tomN, tomo, tomP, and tomQ. These ORFs are assigned the ORF numbers ORF1, 2, 3, 4, 5, 6, 7, 8, 9, 10, 11, 12, 13, 14, 15, 16, 17, 18, and 19, respectively. The genes that participate in the synthesis of 11-de-O-methyltomaymycin are tomA, tomb, tomC, tomD, tome, tomF, tomG, tomI, tomJ, tomK, tomL, tomM, tomN, tomo, tomP, and tomQ. Table 1 shows a list of the specific putative ORFs, the designation of the corresponding genes, the start and stop nucleotides within SEQ ID NO: 2, the lengths of the genes in nucleotides (nt), and the strandedness.

TABLE 1

| ORF number | gene designation | start nt within SEQ ID NO: 2 | stop nt within SEQ ID NO: 2 | gene length (nt) | strandedness |
|---|---|---|---|---|---|
| 1 | orfX0 | 201 | 779 | 579 | forward |
| 2 | orfX1 | 1580 | 2068 | 489 | reverse |
| 3 | tomA | 2785 | 4617 | 1833 | forward |
| 4 | tomB | 4689 | 9296 | 4608 | forward |
| 5 | tomC | 9415 | 10635 | 1221 | forward |
| 6 | tomD | 10632 | 12614 | 1983 | forward |
| 7 | tomE | 12611 | 13210 | 600 | forward |
| 8 | tomF | 13215 | 14786 | 1572 | forward |
| 9 | tomG | 14867 | 15532 | 666 | reverse |
| 10 | tomH | 15785 | 16285 | 501 | forward |
| 11 | tomI | 16282 | 17085 | 804 | forward |
| 12 | tomJ | 17279 | 18178 | 900 | forward |
| 13 | tomK | 18175 | 19050 | 876 | forward |
| 14 | tomL | 19171 | 20961 | 1791 | forward |
| 15 | tomM | 21014 | 23323 | 2310 | forward |
| 16 | tomN | 23410 | 23613 | 204 | forward |
| 17 | tomO | 23648 | 24847 | 1200 | reverse |
| 18 | tomP | 24976 | 27390 | 2415 | forward |
| 19 | tomQ | 27422 | 28867 | 1446 | reverse |

Table 2 shows the ORF number, protein designation, the length in amino acids (aa) of the putative proteins, the SEQ ID numbers of the proteins as identified herein, and the putative function.

TABLE 2

| ORF number | Protein designation | Protein length (aa) | SEQ ID NO: of protein | Putative function |
|---|---|---|---|---|
| 1 | OrfX0 | 192 | 4 | TetR transcriptional regulator family |
| 2 | OrfX1 | 162 | 5 | MarR transcriptional regulator family |
| 3 | TomA | 610 | 6 | Nonribosomal peptide synthetase |
| 4 | TomB | 1532 | 7 | Nonribosomal peptide synthetase |
| 5 | TomC | 406 | 8 | Phenazine biosynthesis protein PhzC |
| 6 | TomD | 660 | 9 | Phenazine biosynthesis protein PhzE |
| 7 | TomE | 199 | 10 | Phenol hydroxylase, reductase component |
| 8 | TomF | 523 | 11 | Phenol-2-monoxygenase oxygenase component |
| 9 | TomG | 222 | 12 | O-Methyltransferase |
| 10 | TomH | 166 | 13 | ImbB1 protein, L-DOPA 2,3-dioxygenase |
| 11 | TomI | 268 | 14 | ImbB2 protein, L-tyrosine 3-hydroxylase |
| 12 | TomJ | 299 | 15 | ImbY protein, unknown, lincomycin biosynthesis |
| 13 | TomK | 291 | 16 | ImbX protein/PhzF protein |
| 14 | TomL | 597 | 17 | ImbA protein, unknown function |
| 15 | TomM | 769 | 18 | Putative drug resistance pump |
| 16 | TomN | 67 | 19 | 4-oxalocrotoate tautomerase |
| 17 | TomO | 400 | 20 | NADH-dependent flavin oxidoreductase |
| 18 | TomP | 804 | 21 | Anthranilate synthase |
| 19 | TomQ | 481 | 22 | Flavin-containing amine oxidase |

The present invention includes functionally active variants or functionally active fragments of a tomaymycin biosynthetic gene cluster. A functionally active variant of a tomaymycin biosynthetic gene cluster relates to a tomaymycin biosynthetic gene cluster having at least one variant ORF with respect to the ORFs as comprised by SEQ ID NO: 1, SEQ ID NO: 2, or SEQ ID NO: 3. The variant ORF encodes a functionally active variant of the respective protein. Such functionally active variants have a sequence identity with the proteins encoded by ORFs comprised by SEQ ID NO: 1, SEQ ID NO: 2, or SEQ ID NO: 3 of more than 50%, of more than 60%, preferably more than 70%, more preferably of more than 80%, still more preferably more than 85%, even more preferably more than 90%, even more preferably more than 95%, most preferably more than 97%, and/or have an activity of more than 50%, more than 60%, more than 70%, more than 80%, more than 90%, more than 95%, or more than 100%, e.g., more than 120%, 150%, 200%, 300%, 400%, or 500% of the activity of the respective proteins encoded by SEQ ID NO: 1, SEQ ID NO: 2, or SEQ ID NO: 3. Preferably, the activity is at least 100%, more preferably at least 120%, most preferably at least 150%. Consequently, the nucleic acid encoding such variants contains deletions, insertions, substitutions, and/or additions within and/or at the 5' and/or 3' termini of the ORFs as comprised by SEQ ID NO: 1, SEQ ID NO: 2, or SEQ ID NO: 3, and show an identity to the sequences of the ORFs as comprised by SEQ ID NO: 1, SEQ ID NO: 2, or SEQ ID NO: 3 of more than 50%, more than 60%, more than 70%, preferably more than 80%, more preferably more than 85%, even more preferably more than 90%, even more preferably more than 95%, most preferably more than 97%. In the context of the present invention, a functionally active variant nucleic acid sequence relative to a nucleic acid sequence as comprised by SEQ ID NO: 1, SEQ ID NO: 2, or SEQ ID NO: 3 encoding a functionally active variant protein with respect to a protein encoded by the tomaymycin biosynthetic gene cluster as comprised e.g. by SEQ ID NO: 1, SEQ ID NO: 2 or SEQ ID NO: 3 means a sequence encoding a variant protein that is capable of participating in the synthesis of 11-de-O-methyltomaymycin and/or that can be substituted for the respective sequence to participate in the synthesis of 11-de-O-methyltomaymycin.

A functionally active fragment of a tomaymycin biosynthetic gene cluster relates to a tomaymycin biosynthetic gene cluster that comprises fragments of at least one ORF as comprised by a tomaymycin biosynthetic gene cluster, such as comprised by SEQ ID NO: 1, SEQ ID NO: 2 or SEQ ID NO: 3. Such fragments of the ORFs encode fragments of the respective proteins. This may include fragment proteins with short internal and/or C- and/or N-terminal deletions whereby the activity of the resulting proteins as identified herein is maintained to an extent of more than 50%, more than 60%, more than 70%, more than 80%, more than 90%, more than 95%, or more than 100%, e.g., more than 120%, 150%, 200%, 300%, 400%, or 500%, of the activity of the proteins encoded by a tomaymycin biosynthetic gene cluster, such as, e. g., comprised by SEQ ID NO: 1, SEQ ID NO: 2, or SEQ ID NO: 3. Preferably, the activity is at least 100%, more preferably at least 120%, and most preferably at least 150%. Consequently, the respective nucleic acid encoding such fragments may contain deletions within and/or at the 5' and/or 3' termini of the ORFs, e. g., deletions of at the most 50%, 45%, 40%, 35%, 30%, 25%, 20%, 15%, 10%, 5%, or less. In the context of the present invention, a fragment of a nucleic acid sequence encoding a functionally active fragment of a protein as comprised herein means a sequence encoding a fragment that is capable of participating in the synthesis of 11-de-O-methyltomaymycin and/or that can be substituted for the respective sequence to participate in the synthesis of 11-de-O-methyltomaymycin. The term "fragment" may encompass full length ORFs in combination with fragment ORFs, as long as this combination results in the synthesis of 11-de-O-methyltomaymycin. Moreover, a fragment of a tomaymycin biosynthetic gene cluster also relates to a tomaymycin biosynthetic gene cluster with internal and/or 5'- and/or 3'-deletions, which may result in the deletion of parts of ORFs and/or in the deletion of whole ORFs, as long as the ability of the fragments of the tomaymycin biosynthetic gene cluster to produce 11-de-O-methyltomaymycin is maintained to an extent of more than 5%, more than 10%, more than 20%, more than 30%, more than 40%, more than 50%, more than 60%, more than 70%, more than 80%, more than 90%, more than 95%, more than 97% or more than 100%, e.g., more than 150%, 200%, 300%, 400%, or 500%, of the activity of the proteins encoded by a tomaymycin biosynthetic gene cluster, such as, e. g., comprised by SEQ ID NO: 1, SEQ ID NO: 2, or SEQ ID NO: 3. A functionally active fragment of a tomaymycin biosynthetic gene cluster as comprised herein encodes proteins that, in their entirety, are capable of effecting the synthesis of 11-de-O-methyltomaymycin and/or proteins that can be substituted for the respective sequence to participate in the synthesis of 11-de-O-methyltomaymycin.

Included within the term "cell producing 11-de-O-methyltomaymycin" are cells that harbor one or more ORFs of a tomaymycin biosynthetic gene cluster, which one or more ORFs are suitable to effect production of 11-de-O-methyltomaymycin. Based on the information of the cluster of Li et al. (2009) and the information provided herein, the skilled person will be able to select those ORFs that are sufficient to effect synthesis of 11-de-O-methyltomaymycin. The at least one ORF may comprise one nucleic acid, or different ORFs may comprise different nucleic acids. Thus, the term "cell producing 11-de-O-methyltomaymycin" includes nucleic acids that comprise all of the ORFs as comprised by a tomaymycin biosynthetic gene cluster, such as ORFs 1 to 19 as comprised by SEQ ID NO: 1, SEQ ID NO: 2, or SEQ ID NO: 3, or nucleic acids that comprise an individual ORF or a combination of individual ORFs such as at least one, at least two, at least three, at least four, at least five or more ORFs, which individual ORF or combination of ORFs encode proteins that are capable of synthesising 11-de-O-methyltomaymycin in a cell.

The terms "comprise", "comprises", and "comprising", as used herein mean to "include or encompass" the desired feature and further features that must not be specifically mentioned. The terms also meant to "consist of" the desired feature and not to include further features except the desired feature. Thus, the nucleic acid or protein referred to herein may be defined by additional features in addition to the definition as indicated, e.g., in addition to the definition by an ORF or SEQ ID number, or may consist of such indicated feature only.

The nucleic acid as comprised herein may be any macromolecule composed of chains of monomeric nucleotides carrying genetic information or form structures within cells. The most common (and therefore preferred) nucleic acids are deoxyribonucleic acid (DNA) and ribonucleic acid (RNA). The nucleic acid can be a DNA molecule, such as a genomic DNA molecule, and may comprise the whole sequence or a fragment of a tomaymycin biosynthetic gene cluster, such as SEQ ID NO: 1 or 2, or a cDNA molecule which can be single- or double-stranded, such as a nucleic acid representing an ORF and encoding a protein, as well as a synthetic DNA, such as a synthesized single-stranded polynucleotide. The nucleic acid may also be an RNA molecule. Preferably, the term also relates to non-coding regions of a gene, wherein these sections are of a relevant size in order to be specific for that gene. Examples of those regions are regulatory elements, such as a promoter. More preferably, the term "nucleic acid" relates to a gene, ORF, promoter, DNA, cDNA, or mRNA. The nucleic acid encoding the desired genetic information, preferably DNA, may comprise the gene(s) of interest, a promoter region, a start codon and a stop codon, and possibly further regions that may be used for regulation of expression of the gene. The regulatory regions may be heterologous to the respective gene or may be associated therewith in nature. The genetic information may be expressed permanently or under the control of a repressor and/or a promoter region in a cell into which the nucleic acid of the present invention is introduced. The obtained cells may be either used directly or used for tissue cultures.

Also comprised by the present invention are nucleic acids that comprise functionally active variants or fragments of the ORFs as comprised by SEQ ID NO: 1, SEQ ID NO: 2, or SEQ ID NO: 3. Functionally active variants or fragments are defined with respect to functionally active variants or fragments of the tomaymycin biosynthetic gene cluster.

It is noted that the above mentioned modifications may be combined. For example, a tomaymycin biosynthetic gene cluster or a nucleic acid as comprised by the present invention may be a fragment comprising one or more variations of the ORFs the invention. It should also be noted that fragments and/or variants include fragments and/or variants, as defined herein, of promoter or regulatory sequences with which the ORFs or fragments or variants thereof are associated in nature. The fragments and/or variants are functionally active in that they regulate the transcription or translation of the genes associated therewith. Moreover, the variant or fragment as referred to above may be an artificially produced nucleic acid.

The term "heterologous" as it relates to nucleic acid sequences, such as coding or control sequences denotes sequences that are normally not associated with a region of a recombinant construct and/or a particular cell. A "heterologous" region is an identifiable segment of a nucleic acid within or attached to another nucleic acid that is not found in association with the other molecule in nature. For example, a heterologous region of a construct could be a regulatory region not found to be associated with a gene as identified herein in nature. Similarly, a heterologous sequence could be a coding sequence that is itself not found in nature as it contains, e.g., synthetic sequences with codons different from the native gene. Moreover, a cell transformed with a construct that is not normally present in the cell would be considered heterologous for the purposes of the present invention. A homologous nucleic acid sequence is a variant sequence as defined herein. The term "homologous" may be used interchangeably with variant. The term "homologous" may also refer to an identical sequence.

An ORF is an open reading frame that is a DNA sequence that could potentially encode a protein. In the context of the present invention, the term "ORF" stands for open reading frame in the tomaymycin biosynthetic gene cluster as isolated from *Streptomyces achromogenes* var. *tomaymyceticus*, from *Streptomyces* species FH6421, or any other microorganism producing 11-de-O-methyltomaymycin. The tomaymycin biosynthetic gene cluster has been elucidated by Li et al. (2009) and the cluster and ORFs identified therein are comprised for the purposes of the present invention. Moreover, the present inventors succeeded in identifying the tomaymycin biosynthetic gene cluster of *Streptomyces* species FH6421 and identified 19 ORFs. Furthermore, any ORFs of tomaymycin biosynthetic gene clusters from strains other than *Streptomyces achromogenes* var. *tomaymyceticus* or *Streptomyces* species FH6421 that are known in the art or will be identified are included herein. Also functionally active variants or functionally active fragments of the ORFs of *Streptomyces achromogenes* var. *tomaymyceticus* or *Streptomyces* species FH6421 fall within the term ORFs as comprised herein, as long as such ORFs encode functionally active proteins.

The substitution of a variant or fragment nucleic acid for ORFs to participate in the synthesis of 11-de-O-methyltomaymycin means that this variant or fragment nucleic acid can be inserted into the genome of a microorganism harbouring a tomaymycin biosynthetic gene cluster instead of the ORF to which it is a variant or to which it is a fragment, thereby expressing a variant or fragment protein that takes over the function of the respective protein and participates in the synthesis of 11-de-O-methyltomaymycin. The extent to which the variant or fragment takes over the function is as defined herein.

In another embodiment, the nucleic acid may comprise the sequences of a tomaymycin biosynthetic gene cluster, such as, e. g., comprised by SEQ ID NO: 1, SEQ ID NO: 2, or SEQ ID NO: 3. The nucleic acid may also encode proteins with the same amino acids as the proteins encoded by a tomaymycin biosynthetic gene cluster, such as, e. g., comprised by SEQ ID NO: 1, SEQ ID NO: 2, or SEQ ID NO: 3, but differs in its nucleotide composition due to the degeneracy of the genetic code.

In a further embodiment, the tomaymycin biosynthetic gene cluster or the nucleic acid hybridizes under stringent conditions to a nucleic acid that comprises the tomaymycin biosynthetic gene cluster as comprised by SEQ ID NO: 1, SEQ ID NO: 2, or SEQ ID NO: 3. In the present invention, the term "hybridize(s)(ing) under stringent conditions" refers to the formation of a hybrid between two nucleic acid molecules under conditions that allow the formation of a so-called specific hybrid, while a non-specific hybrid is substantially not formed. An example of such conditions includes conditions under which a complementary strand of a highly identical nucleic acid, namely, a DNA composed of a nucleotide sequence having 70% or more, preferably 80% or more, more preferably 85% or more, still more preferably 90% or more and even more preferably 95% or more identity with the nucleotide sequence of SEQ ID NO: 1, SEQ ID NO: 2, or SEQ ID NO: 3 hybridizes, while a less complementary strand of a nucleic acid less identical than the above does not hybridize. More specifically, such conditions refer to conditions in which the sodium salt concentration is 15 to 750 mM, preferably 50 to 750 mM, and more preferably 300 to 750 mM; the temperature is 25 to 70° C., preferably 50 to 70° C., and more preferably 55 to 65° C.; and the formamide concentration is 0 to 50%, preferably 20 to 50%, and more preferably 35 to 45%. Furthermore, under stringent conditions, conditions for washing a filter after hybridization normally comprises the following: the sodium salt concentration is 15 to 600 mM, preferably 50 to 600 mM, and more preferably 300 to 600 mM; and the temperature is 50 to 70° C., preferably 55 to 70° C., and more preferably 60° C. Stringency, and thus specificity, can, e.g., be increased by increasing the reaction temperature and/or lowering the ion strength of the reaction buffer. For example, low stringent conditions comprise hybridization in 3×SSC at room temperature to 65° C., and highly stringent conditions comprise hybridization in 0.1×SSC at 68° C. Exemplary moderately stringent conditions (nucleic acids hybridize under moderately stringent conditions if they are maximally degenerate with respect to their codon composition) comprise 50% formamide, 5×SSC and 1% SDS at 42° C. and washing in 1×SSC at 45° C. Highly stringent conditions comprise incubation at 42° C., 50% formamide, 5×SSC and 1% SDS (e.g., 50% formamide, 5×SSC and 1% SDS, 50 mM sodium phosphate, 5×Denhardt's solution, 10×dextran sulphate, 20 mg/ml sheared salmon sperm DNA) or 5×SSC and 1% SDS at 65° C. and washing in 0.2×SSC and 0.1% SDS at about 65° C. (1×SSC stands for 0.15 M sodium chloride and 0.015 M trisodium citrate buffer). Preferred in the present invention are moderately or highly stringent conditions, more preferred are highly stringent conditions. In the context of the present invention, a "hybridizing" sequence means a sequence that encodes a protein that participates in the synthesis of 11-de-O-methyltomaymycin and/or that can be substituted for the ORF to which it specifically hybridizes to participate in the synthesis of 11-de-O-methyltomaymycin.

The tomaymycin biosynthetic gene cluster or nucleic acid as comprised or referred to herein may be provided by any methods known in the art. Using the sequence information provided herein or in the prior art, primers suitable for amplification/isolation of one or more ORFs can be determined according to standard methods well known to those of skill in the art. Primers suitable for amplification/isolation of any one or more of the ORFs as defined herein are designed according to the nucleotide sequence information provided in the sequence listing. The procedure is as follows: a primer is selected that may consist of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. Typically such amplifications will utilize the DNA or RNA of an organism containing the requisite genes (e. g., *Streptomyces achromogenes*, such as *Streptomyces achromogenes* var. *tomaymyceticus*, *Streptomyces* species FH6421, or any other strain producing 11-de-O-methyltomaymycin) as a template. A standard PCR reaction will be performed that typically contains 0.5 to 5 Units of Taq DNA polymerase per 100 µl, 20 to 200 µM deoxynucleotide each, preferably at equivalent concentrations, 0.5 to 2.5 mM magnesium over the total deoxynucleotide concentration, 105 to 106 target molecules, and about 20 pmol of each primer. About 25 to 50 PCR cycles are performed. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for denaturation of G+C-rich targets. The number of cycles performed depends on the starting concentration of target molecules, though typically more than 40 cycles are not recommended as non-specific background products tend to accumulate. An alternative method for retrieving polynucleotides encoding variant proteins defined herein is by hybridization screening of a DNA or RNA library using the primers and probes. A nucleotide probe has a sequence found in or derived by the degeneracy of the genetic code from a sequence within the tomaymycin biosynthetic gene cluster as comprised by SEQ ID NO: 1, SEQ ID NO: 2, or SEQ ID NO: 3, or a variant thereof or encoding any of SEQ ID NOs: 4 to 22 or functionally active variants thereof. The term "probe" refers to DNA, preferably single-stranded, or RNA molecules or modifications or combinations thereof, that hybridize under stringent conditions, as defined herein, to nucleic acid molecules comprised within the tomaymycin biosynthetic gene cluster identified by SEQ ID NO: 1, SEQ ID NO: 2, or SEQ ID NO: 3, or variants thereof or encoding any of the proteins of SEQ ID Nos: 4 to 22 or functionally active variants thereof, or their complementary or sense sequences. Generally, probes are significantly shorter than full-length sequences. They may contain from 5 to 100, preferably 10 to 80 nucleotides, more preferably 10 to 50 nucleotides, still more preferably 10 to 40 nucleotides and still more preferably 15 to 25 nucleotides. In particular, such probes may have sequences that are at least 70%, at least 75%, preferably at least 85%, more preferably at least 95%, and most preferably 100% homologous to a coding (ORFs 1 to 19) or non-coding sequence as comprised by SEQ ID NO: 1, SEQ ID NO: 2, or SEQ ID NO: 3, or that are, to the above extents, complementary thereto. They may contain modified bases, such as inosine, methyl-5-deoxycytidine, deoxyuridine, dimethylamino-5-deoxyuridine or diamino-2, 6-purine. Sugar or phosphate residues may also be modified or substituted as is known in the art. For example, a deoxyribose residue may be replaced by a polyamide, and a phosphate residue may be replaced by ester groups, such as diphosphate, alky, arylphosphonate or phosphorothioate esters. Alternatively or in addition, the 2'-hydroxyl group on ribonucleotides may be modified by including such groups as alkyl, O-alkyl or halogen groups. Probes of the invention are used in any conventional hybridization technique such as dot blot, Southern blot, northern blot, or sandwich technique, which is a technique using specific capture and/or detection probes with nucleotide sequences that at least differ partially from each other (Sambrook et al., Molecular cloning: A laboratory manual. Cold Spring Harbor, N.Y.: Cold Spring Harbor Laboratory Press, 2001). Hybridization procedures are well-known and are described in the art and herein.

Alternatively or additionally to the above, the nucleic acid may be provided by cloning and thereby introducing it into and amplifying it in a cell. The procedure of introducing a gene into a recipient cell is called transformation. The genes can be introduced into the cells by a variety of means known in the art and adapted to each cell type. The term "cell" refers to the cell in which the gene is expressed irrespective of whether it is a prokaryotic cell or a eukaryotic cell and of whether the cell naturally expresses the respective genes or not. Thereby the cell may be a cell that naturally harbors the gene expressing the protein as comprised by the present invention, e.g., *Streptomyces achromogenes*, such as *Streptomyces achromogenes* var. *tomaymyceticu*, or *Streptomyces* species FH6421, or any other strain producing 11-de-O-methyltomaymycin. Recombinant DNA cloning techniques well known in the art for introducing and expressing a nucleic acid molecule can be used to introduce and express the gene that is either endogenous if the cell harbours the respective gene or is heterologous if the gene is not endogenous to the cell. Cells can be transformed using any appropriate means, including viral or bacteriophage based vectors, chemical agents, electroporation, calcium phosphate co-precipitation or direct diffusion of DNA. Vectors are agents that transport an endogenous or heterologous gene into the cell and may include appropriate transcriptional and translational control signals, such as a promoter. Vectors can be a plasmid, a virus (e. g. bacteriophage) or others known in the art. Vectors are able to autonomously replicate in a cell or can be incorporated into chromosomal DNA. The term "vectors" includes those that function primarily for insertion of a nucleic acid into a cell, those that function primarily for replication of a nucleic acid (replication vector) in a cell or those that function primarily for transcription and/or translation of DNA or RNA in a cell. Examples of vectors include pBTrp2, pBTac1, pBTac2 (all of which are manufactured by Boehringer Mannheim), pKK263-2 (manufactured by Pharmacia), pGEX (manufactured by Pharmacia), pSE280 (manufactured by Invitrogen), pGEMEX-1 (manufactured by Promega), pQE-8 (manufactured by Qiagene), pET-3 (manufactured by Novagen), pBluescriptII SK+(manufactured by Stratagene), pBluescript II SK(−) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pSTV28 (manufactured by Takara Bio Inc.), pUC118 (manufactured by Takara Bio Inc.), pHW1520 (manufactured by MoBiTec), pSET152, pOJ436 and pOJ446 (Bierman M, et al., 1992), pSH19 (Herai S, et al., 2004), pUWL199, pUWL218 and pUWL219 (Wehmeier U. F., 1995) and pIJ6021 (Takano E. et al., 1995). A preferred vector is pOJ446 and derivatives thereof.

The promoter can be inducible or constitutive, general or cell specific, nuclear or cytoplasmic specific, heterologous or associated with the gene in nature. Any type of promoter can be used, as long as it functions in the cells producing 11-de-O-methyltomaymycin. Examples of the promoter include promoters derived from *Escherichia coli* or phage, such as a trp promoter (Ptrp), a lac promoter (Plac), a PL promoter, a PR promoter or a PSE promoter, a SPO1 promoter, a SPO2 promoter, and a penP promoter. In addition, artificially designed or modified promoters, such as a promoter formed by placing two Ptrp in series (Ptrp*2), a tac promoter, a lacT7 promoter or a let I promoter, can be used. Moreover, a xylA promoter for expression in the bacteria of the genus *Bacillus*, or a P54-6 promoter for expression in the bacteria of the genus *Corynebacterium* can be used. Additional useful promoters are PermE (Bibb et al., 1985, PermE* (Bibb et al., 1994), PtipA (Murakami et al., 1989), PnitA-NitR expression system (Herai et al., 2004) and actII-ORF4/PactI activator-promoter system (Fernández-Moreno et al., 1991). Selection of promoters, vectors, and other elements are a matter of routine design. Many such elements are described in literature and are available through commercial suppliers. A single gene can be introduced into a cell. Also, more than one gene can be introduced into a cell and expressed therein. Where large clusters are to be expressed, it is preferable that phagemids, cosmids, P1s, YACs, BACs, PACs, HACs, or similar cloning vectors are used. If more than one gene is introduced into a cell, then the genes may be under the regulation of the same promoter and/or regulatory elements. Alternatively, the genes may be under the regulation of different promoter and/or regulatory elements. Usually, the method of transfer includes transfer of a selectable marker to the cells. In general, a cell line is transformed by any of the means mentioned above wherein the transgene is operatively linked to a selectable marker. Following transformation, cells are grown for an adapted period of time. Transformed cells exhibit resistance to the selection and are able to grow, whereas non-transformed cells die in general. Examples for selective markers include puromycin, zeocin, neomycin and hygromycin B, which confer resistance to puromycin, zeocin, aminoglycoside G-418 and hygromycin B, respectively.

In principle, any cells capable of harboring and expressing a recombinant tomaymycin biosynthetic gene cluster or one or more genes of the tomaymycin biosynthetic gene cluster that are useful or sufficient to effect production of 11-de-O-methyltomaymycin can be used in the methods of the present invention. Examples include microorganisms such as bacteria, yeasts, filamentous fungi, animal cells, and plant cells, such as, without limitation, cells of *E. coli* strains, of the order Actinomycetales, such as a *Streptomyces* species, such as *Streptomyces albus*, of yeast strains such as *Saccharomyces cerevisiae*.

Preferred embodiments are bacterial cells, such as cells of the order Actinomycetales, such as *Streptomyces* species, such as *Streptomyces* species FH6421, or *Streptomyces albus*, such as *Streptomyces albus* pSTW102tc cells with a wildtype tomaymycin biosynthetic gene cluster that is mutagenized, such as *Streptomyces* species FH6421-1038, *Streptomyces* species FH6421-1069, or *Streptomyces* species FH6421-1334.

The object of the present invention is the provision of advantageous methods to enhance the production of 11-de-O-methyltomaymycin by cells that produce 11-de-O-methyltomaymycin. The cells may comprise a tomaymycin biosynthetic gene cluster that is identified by SEQ ID NO: 1, SEQ ID NO: 2, or SEQ ID NO: 3, or may comprise a tomaymycin biosynthetic gene cluster as identified by SEQ ID NO: 1, SEQ ID NO: 2, or SEQ ID NO: 3, which comprises functionally active variant or fragments of ORFs or promoter or regulatory regions, as long as such a cell is capable of producing 11-de-O-methyltomaymycin. Moreover, comprised herein are cells that comprise only part of the ORFs, possibly comprising functionally active variants and/or fragments of ORF(s) as comprised herein, as long as the cells are capable of producing 11-de-O-methyltomaymycin. Variant or fragment ORFs or promoter or regulatory regions may be natural or may be artificial. Variant or fragment ORFs or promoter or regulatory regions may serve to enhance the productivity of 11-de-O-methyltomaymycin by cells harboring such variant or fragment ORFs. The tomaymycin biosynthetic gene cluster or ORFs or promoter or regulatory regions may be artificially modified to result in a tomaymycin biosynthetic gene cluster or ORFs or promoter or regulatory regions that result in the production of a higher yield of 11-de-O-methyltomaymycin versus the production of 11-de-O-methyltomaymycin by a strain harboring the tomaymycin biosynthetic gene cluster identified by SEQ ID NO: 1, SEQ ID NO: 2, or SEQ ID NO: 3, or versus the parent strain. Such mutated strains are inter alia disclosed herein as *Streptomyces* species FH6421-1038, *Streptomyces* species FH6421-1069, *Streptomyces* species FH6421-1334.

Consequently, in a further embodiment of the present invention, cells naturally producing 11-de-O-methyltomaymycin and/or comprising the tomaymycin biosynthetic gene cluster or cells that have been transformed with an individual ORF or a combination of ORFs that may comprise variant or fragment ORFs, promoter or regulatory regions, as referred to above, and producing 11-de-O-methyltomaymycin, are mutagenized in order to enhance the production rate of 11-de-O-methyltomaymycin.

Preferably, the production rate is enhanced by a factor of at least 1.3, at least 1.5, at least 1.8, at least 2.0, at least 2.5, at least 5.0, or a least 10.0. More preferably, the production rate is enhanced by the factor of 1.5 to 2.0, and most preferably by a factor of 1.5 to 1.8.

For this invention, *Streptomyces albus* J1074 was transformed with the vector pSTW102tc (SEQ ID NO: 3) resulting in *Streptomyces albus* J1074/pSTW102tc with a yield of 338±18.8 mg/l in a coil fitted shake flask using production medium (20 g/l soy flour, 10 g/l corn steep solid, 20 g/l glycerol, 7.5 g/l NaCl, 2 g/l CaCO$_3$), and strain *Streptomyces* species FH6421 with a productivity of about 50±10 mg/l, and as compared to the standard strain with 20 mg/l under same conditions.

The proteins that are produced by a cell that produces 11-de-O-methyltomaymycin and participates in the synthesis of 11-de-O-methyltomaymycin encompasses proteins encoded by SEQ ID NO: 1, SEQ ID NO: 2, or SEQ ID NO: 3, such as, e.g., proteins identified by SEQ ID Nos: 4 to 22, and encompass proteins as they occur in other organisms that produce 11-de-O-methyltomaymycin that are orthologs or homologs whereby these orthologs or homologs have the same function as the proteins encoded by SEQ ID NO: 1, SEQ ID NO: 2, or SEQ ID NO: 3. Preferably, orthologs or homologs thereof differ from the sequences of the proteins encoded by SEQ ID NO: 1, SEQ ID NO: 2, or SEQ ID NO: 3, e.g., by addition, deletion, substitution, and/or insertion of amino acids, and have a sequence identity with the proteins encoded by SEQ ID NO: 1, SEQ ID NO: 2, or SEQ ID NO: 3 of more than 50%, of more than 60%, more than 70%, preferably of more than 80%, more preferably more than 85%, even more preferably more than 90%, even more preferably more than 95%, most preferably more than 97%, and/or have an activity of more than 5%, more than 10%, more than 20%, more than 30%, more than 40%, more than 50%, more than 60%, more than 70%, more than 80%, more than 90%, more than 95%, more than 97% or more than 100%, e.g. more than 150%, 200%, 300% 400% or 500% of the activity of the respective proteins of SEQ ID Nos: 4 to 22.

In the context of the present invention the naturally or non-naturally occurring variant of the proteins encoded by SEQ ID NO: 1, SEQ ID NO: 2, or SEQ ID NO: 3 is a functionally active protein in that it maintains the biological function of the reference protein, i.e. the involvement in a reaction in which the reference protein is involved under natural conditions (in case of a non-natural variant, the biological function of the reference protein).

Non-naturally occurring variants of the proteins of SEQ ID Nos: 4 to 22 or of naturally occurring variants thereof may be obtained by a limited number of amino acid deletions, insertions and/or substitutions, particularly deletions, insertions and/or substitutions of, e.g., at most 10, 9, 8, 7, 6, 5, 4, 3, 2 or 1 amino acid(s), thereby obtaining a sequence identity or activity of the respective wild-type proteins, e.g. with respect to SEQ ID Nos: 4 to 22, as mentioned above.

In another embodiment of the present invention, the variant of the proteins encoded by SEQ ID NO: 1, SEQ ID NO: 2, or SEQ ID NO: 3 could be a fragment, wherein the fragment is still functionally active. This may include proteins encoded by SEQ ID NO: 1, SEQ ID NO: 2, or SEQ ID NO: 3, or variants thereof as detailed above with short internal and/or C- and/or N-terminal deletions (e.g. deletions of at most 20, 19, 18, 17, 16, 15, 14, 13, 12, 11, 10, 9, 8, 7, 6 5, 4, 3, 2, or 1 amino acids within the variant and/or at the C- and/or N-termini or total deletions of 5%, 10%, 20%, 30%, 40%, 50%, 60%, 70% amino acids or any values in between these values). Additionally, the fragment may be further modified as detailed above with respect to variants.

Alternatively or additionally, the proteins encoded by SEQ ID NO: 1, SEQ ID NO: 2, or SEQ ID NO: 3 or variants thereof as described above may comprise one or more amino acid substitution(s). However, semi-conservative and especially conservative amino acid substitutions, wherein an amino acid is substituted with a chemically related amino acid, are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

TABLE 3

| Amino acid | Conservative substitution | Semi-conservative substitution |
| --- | --- | --- |
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein that have an alpha-helical or a beta-sheet structure.

It is noted that the above modifications of the proteins encoded by SEQ ID NO: 1, SEQ ID NO: 2, or SEQ ID NO: 3 may be combined. The variants of the present invention may be e.g. a fragment of a protein encoded by SEQ ID NO: 1, SEQ ID NO: 2, or SEQ ID NO: 3 comprising one or more amino acid substitutions. It is furthermore noted that any of the proteins encoded by SEQ ID NO: 1, SEQ ID NO: 2, or SEQ ID NO: 3 may be combined with any of a variant or fragment of the proteins encoded by SEQ ID NO: 1, SEQ ID NO: 2, or SEQ ID NO: 3.

In one aspect, the present invention provides a nucleic acid comprising at least one nucleic acid selected from:
(a) a nucleic acid comprising at least one of the Open Reading Frames (ORFs) 1 to 19 as comprised by SEQ ID NO: 2 encoding proteins of SEQ ID NOs: 4 to 22 or a variant or fragment thereof whereby the variant or fragment encodes a functionally active variant or fragment of a protein of SEQ ID NOs: 4 to 22,
(b) a nucleic acid encoding at least one of the proteins of SEQ ID NOs: 4 to 22 or a functionally active variant or fragment thereof,
(c) a nucleic acid encoding a protein that is at least 70%, 80%, 90%, 95% or 97% identical in amino acid sequence to a protein or fragment thereof encoded by the nucleic acid of (a) or (b),
(d) a nucleic acid that hybridizes under stringent conditions with a nucleic acid of (a) to (c),
(e) a nucleic acid that is complementary to a nucleic acid of (a) to (d).

In another aspect, the nucleic acid comprises or consists of the tomaymycin biosynthetic gene cluster having the sequence of SEQ ID NO: 2 or having a variant or fragment sequence of SEQ ID NO: 2 harboring a variant or fragment of at least one of ORFs 1 to 19, whereby the variant or fragment encodes a functionally active variant or fragment of a protein of SEQ ID NOs: 4 to 22.

In a further aspect, an expression vector comprising the nucleic acid as referred to above is provided.

In still a further aspect, a cell comprising the above nucleic acid, or a cell transformed with the above expression vector is provided. Preferably the cell is *Streptomyces* species FH6421.

With respect to the tomaymycin biosynthetic gene cluster, the ORFs or genes comprised therein, the proteins encoded thereby and variants and fragments of the tomaymycin biosynthetic gene cluster or of ORFs or proteins, these features are described above in the context of the method for producing 11-de-O-methyltomaymycin and it is referred to the definitions provided therein.

EXAMPLES

The invention is further exemplified by the following examples:

Example 1—Knock Out of Biosynthetic Genes from the Tomaymycin Biosynthetic Gene Cluster To enable mutasynthesis of tomaymycin analogous structures genes providing the precursors of the biosynthesis were deleted in the heterologous expression system. The anthranilic acid derivative incorporated in tomaymycin is derived from 3-deoxy-D-arabino-heptulosonate-7-phosphate partially utilizing the intrinsic shikimate pathway of the native producer strain or the heterologous host. For exchange of the A-Ring the genes tomC, tomD, tomE, tomF and tomG, were deleted. *S. albus* J1074 strains carrying the resulting plasmid pStW102tcΔC-G are not producing tomaymycin but did incorporate 2-amino-5-bromobenzoic acid. Deletion of tomH and tomI also eliminated tomaymycin production but allowed incorporation of (S)-4-methylenepyrrolidine-2-carboxylic acid.

Deletion of genes from pStW102tc involved in the supply of precursors for tomaymycin was performed by Red/ET as described by the supplier (GeneBridges). The zeocin resistance gene from pCK_T7A1_att was amplified by the primer pair pr130f, pr130r (for primers see below) and the PCR product used to delete the genes tomC, tomD, tomE, tomF and tomG—(without being bound to theory, which is believed to be involved in the supply of the anthranilic acid derived residue). The tetracycline resistance gene from pACYC184 was amplified by the primer pair pr156f, pr156r and the PCR product used to delete tomH and tomI—(without being bound to theory, which is believed to be involved in the supply of the ethylidene proline residue). The deletions were verified by restriction digest followed by gel electrophoresis. Resistance genes were removed via XmaJI, XbaI digest and religation yielding pStW102tcΔtomC-G and pStW102tcΔtomHI respectively. Plasmids were then transferred into *S. albus* J1074.

PCR-primers used for deletion of biosynthetic genes via Red/ET. Restriction sites are underlined and the corresponding restriction enzyme given in parentheses.

```
pr130f
                              (SEQ ID NO: 23)
5'-CCGACCATCCACCACACGGCAATCGCCGAAGCGGTCGCCGGACACCG
AAAGCCTAGGGCGAGGAAGCGGTGATCACAC-3' (XmaJI)

pr130r
                              (SEQ ID NO: 24)
5'-GCAACCATGGAACAAGAGCGATGGAACAGTGTCGACGTCTACTTCAG
CTCTCTAGATTGATAAGCTTGGCGTAATGGATCTG-3' (XbaI)

pr156f
                              (SEQ ID NO: 25)
5'-GAAAAAGCCTGTCCCGGATAGGAGTGTCATTTCATGCGAGAAGACTC
GGCCGTCCCTAGGCCTGAAGTCAGCCCCATACG-3' (XmaJI)

pr156r
                              (SEQ ID NO: 26)
5'-CCTCGGGCAGTGCGGCGTCCTCCTGCGCGGTCAGCCCGGGGTACAGC
CCGTTTCTAGACTTCCATTCAGGTCGAGGTG-3' (XbaI)
```

Example 2—Phenotypical Verification of *S. albus* J1074/pStW102tcΔtomC-G and *S. albus* J1074/pStW102tcΔtomHI Mutasynthesis was performed by cultivation of the mutagenized strains in 500 µl production medium (20 g/l soy flour, 10 g/l corn steep solid, 20 g/l glycerol, 7.5 g/l NaCl, 2 g/l CaCO₃) in a punctured 2 ml reaction tube at 30° C. and 1000 rpm. After 24 h *S. albus* J1074/pStW102tcΔtomC-G cultures were complemented with 2-amino-5-bromobenzoic acid. *S. albus* J1074/pStW102tcΔtomHI cultures were supplemented with (S)-4-methylenepyrrolidine-2-carboxylic acid (chemicals provided by Sanofi-Aventis) to a final concentration of 500 µM each. After 24 h samples were taken and analyzed by HPLC-MS.

Example 3—Production of 9-chloro-11-de-O-methyl-8-deshydroxy-7-hydroxytomaymycin (CDHT)

200 ml of production medium (20 g/l soy flour, 10 g/l corn steep solid, 20 g/l glycerol, 7.5 g/l NaCl, 2 g/l CaCO₃) complemented with 60 µg Apramycin/l in 2.5 l buffled flasks with tissue caps were inoculated with 10 ml from a densely grown overnight culture of *S. albus* J1074/pStW102tcΔC-G. The culture was incubated at 30° C. and 150 rpm overnight followed by feeding with 17.2 mg 2-amino-3-chlorobenzoic acid dissolved in 200 µl DMSO giving a final concentration of 0.5 mM. Incubation was repeated overnight under said conditions. Cells were pelleted by centrifugation and discarded. pH of the supernatant was adjusted to 7.0 and it was washed two times with 1 volume of hexane. Extraction was performed twice with 1 volume of ethyl acetate, organic layers were pooled and dried by rotary evaporation. Crude extract was solved in 1.5 ml H₂O/acetonitrile (1:1 v/v) and subjected to semipreprative HPLC for isolation of CDHT.

Figure 4:
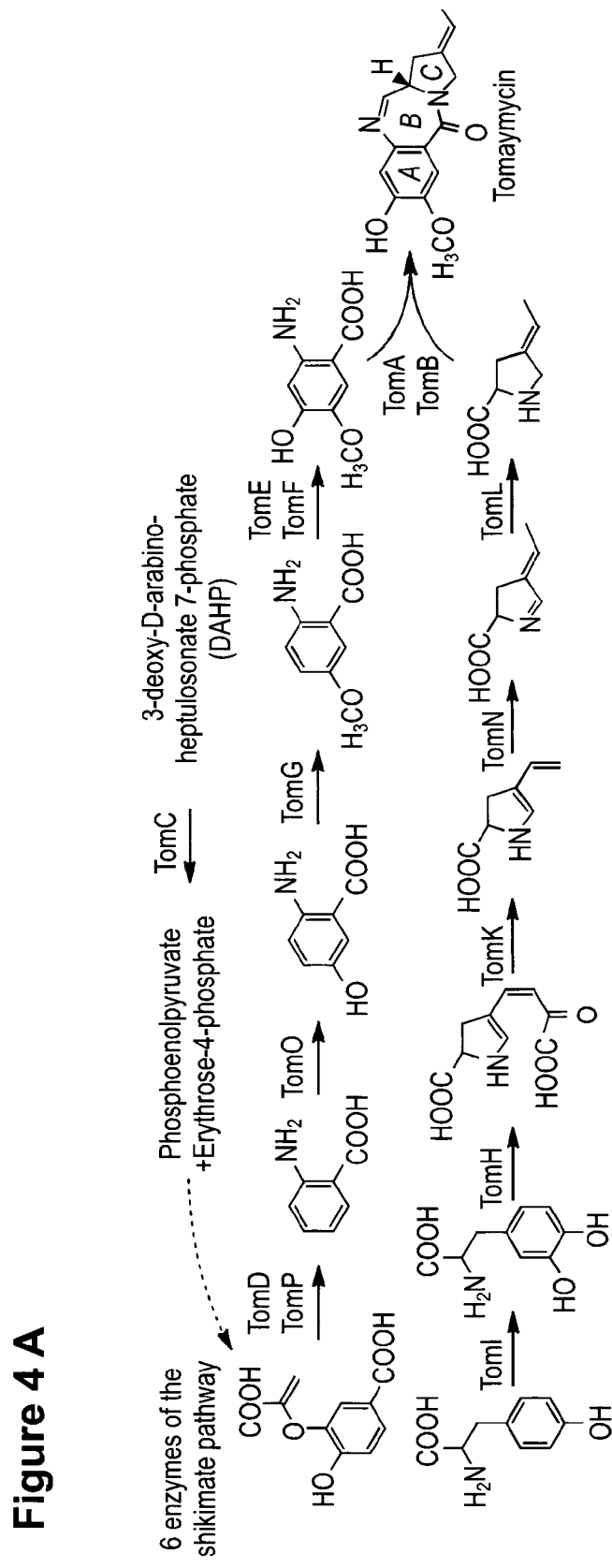
FIG. 4 is a presentation of A) Biosynthetic pathway of tomaymycin, B) Structure of fed 2-amino-5-bromobenzoic acid and proposed structures for resulting mutasynthesis products, C) Extracted ion chromatogram (C14H16BrN2O2+: 323.03897 Da±5 ppm; C14H14BrN2O2+: 321.02332 Da±5 ppm) of *Streptomyces*
Figure 4B:
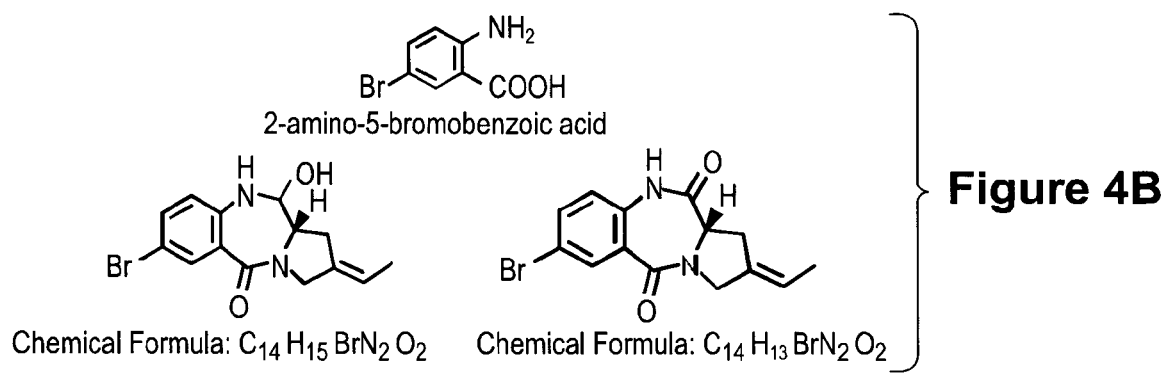
Figure 4C:
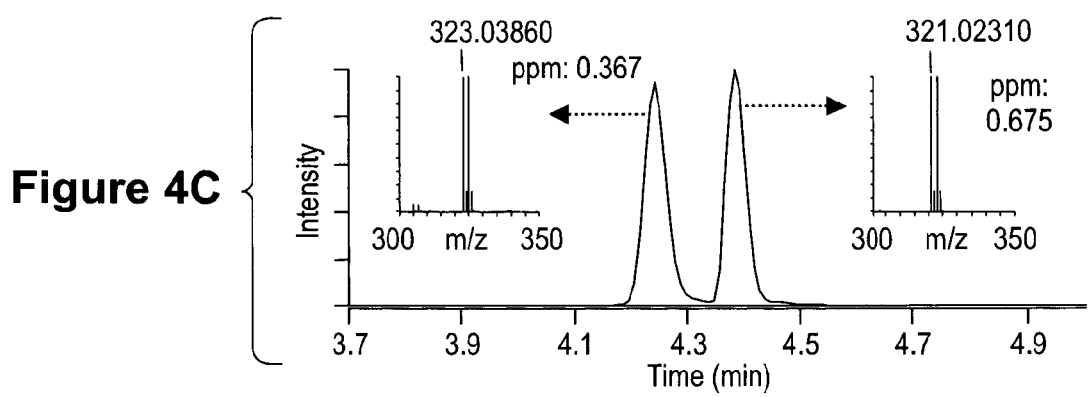
Figure 4D:
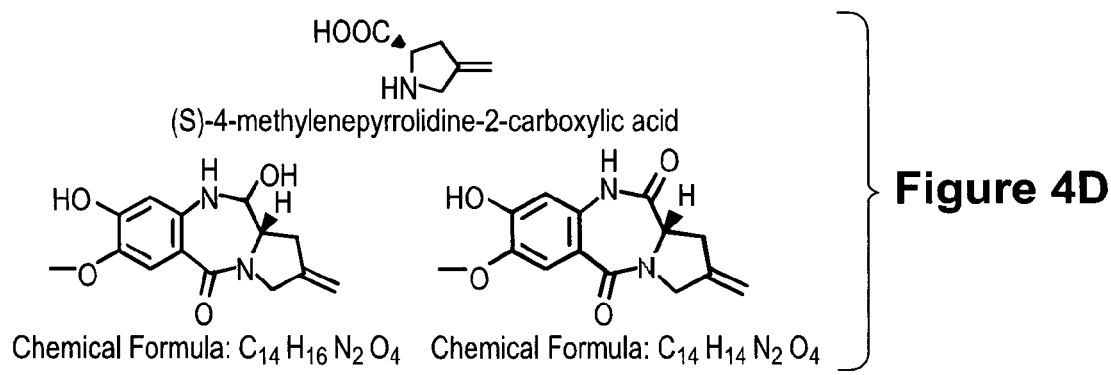
Figure 4E:
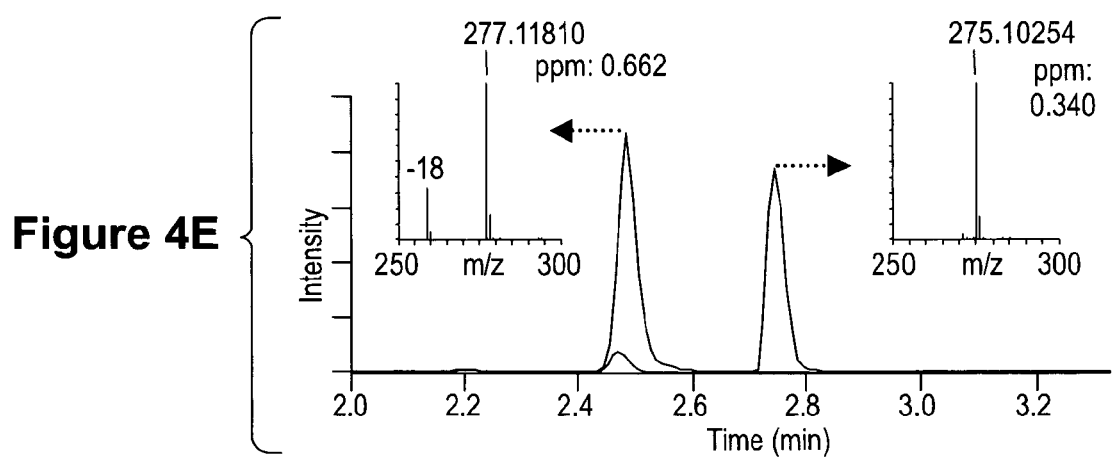

The biosynthetic pathway, fed amino acids, proposed structures and HPLC-MS measurements are shown in FIG. 4 (C and E).

Example 4—Purification of CDHT

Reversed phase chromatography was performed by a Dionex HPLC system (Famos autosampler, P680 pump, TCC100 thermostat, and PDA100 detector) equipped with a Phenomenex Luna C18, 250×4.6 mm, 5 µm dp column. Separation was achieved by a linear gradient using (A) H₂O+0.1% formic acid to (B) aceto nitrile+0.1% formic acid at a flow rate of 5 ml/min and 30° C. The gradient started at 10% B and increased to 56% B in 18 min (2.56% B/min). UV data was acquired at 254 nm. The sample was injected by µl-pick-up technology with a water/methanol (50:50 v/v) mixture as supporting solvent. Fractions were collected manually and analysed by LC-HRMS. Fractions containing a mass corresponding to CDHT were pooled, pH adjusted to 7.0, extracted two times with two volumes ethyl acetate, organic fractions pooled and dried by rotary evaporation. Obtained CDHT was analysed by LC-HRMS and NMR.

Obtained substances did match the mass for the proposed structures with deviations <1 ppm; showed the typical elimination of water for the hemiaminal form of the PBD; the mass reduction of 2 for the oxidized form characteristic for tomaymycin and in case of the 2-amino-5-bromobenzoic feeding the isotope distribution exhibited the M+: M+2 intensity ratio of 1:1 of brominated structures in MS.

Example 5—NMR-Spectroscopy

To further affirm the successful mutasynthesis 2-amino-3-chlorobenzoic acid was fed in larger scale, the product purified and its structure elucidated by NMR. Due to the remaining activity of tomo the obtained structure was hydroxylated at C-7 yielding 9-chloro-8-deshydroxy-7-hydroxytomaymycin. Structure data showed the presence of both diastereomeres of the hemiaminal as well as the imine at the N-10, C-11 position.

NMR spectra were recorded at 298 K on a 500 MHz Avance III spectrometer by Bruker BioSpin GmbH equipped with a cryoplatform. CD3CN was used as solvent. Chemical shift values of 1H and 13C NMR spectra are reported in ppm relative to the residual solvent signal given as an internal standard. Multiplicities are described using the following abbreviations: s=singlet, d=doublet, t=triplet, q=quartet, m=multiplet, b=broad; corrected coupling constants are reported in Hz (cf. Figure X).

1H-NMR Data relating to 9-chloro-8-deshydroxy-7-hydroxytomaymycin: (500 MHz, MeCN-d4): δ7.62 (bs, Ph-OH) 7.00 (m, 2H, 6-H, 8-H), 5.59 (m, 1H, 12H), 5.20 (d, J=8.9 Hz, 1H, H-11), 5.10 (bs, 1H, NH), 4.22 (m, 1H, 3-Ha), 4.07 (m, 1H, 3-Hb), 3.65 (t, J=9.0 Hz, 1H, 11a-H), 2.64 (m, 1H, 1-Ha), 2.51 (m, 1H, 1-Hb), 1.66 (m, 3H, 13-H) ppm; 13C-NMR (125 MHz, MeCN-d4): δ167.5 (5-C), 153.4 (7-C), 134.2 (9 C or 5a-C), 133.9 (2-C), 131.8 (9a-C), 128.3 (5a-C or 9-C), 119.6 (6-C), 119.0 (13-C), 115.6 (8-C), 87.5 (11-C), 60.6 (11a-C), 51.8 (3-C), 31.5 (1-C), 15.0 (13-C) ppm; HR-MS (ESI): calculated for C14H16ClN2O3 [M+H]+: 295.0849. found 295.0844.

1H-NMR relating to imine 9-chloro-8,11-dideshydroxy-7-hydroxytomaymycin: (500 MHz, MeCN-d4): δ7.75 (d, J=4.6 Hz, 1H, 11-H), 7.62 (bs, Ph-OH) 7.26 (d, J=2.8 Hz, 6-H), 7.16 (d, J=2.8 Hz, 8-H), 5.59 (m, 1H, 12H), 4.16 (m, 1H, 3-Ha), 4.10 (m, 1H, 3-Hb), 3.90 (m, 1H, 11a-H), 3.03 (m, 1H, 1-Ha), 2.94 (m, 1H, 1-Hb), 1.72 (m, 3H, 13-H) ppm; 13C-NMR (125 MHz, MeCN-d4): δ165.6 (11-C), 164.0 (5-C), 155.9 (7-C), 136.9 (9a C), 134.6 (2-C), 132.5 (9 C or 5a-C), 131.1 (5a-C or 9-C), 120.6 (8-C), 119.0 (13-C), 115.1 (6-C), 54.9 (11a-C), 52.1 (3-C), 31.3 (1-C), 14.6 (13-C) ppm; HR-MS (ESI): calculated for C14H14ClN2O2 [M+H]+: 277.0744. found 277.0741.

---

The invention claimed is:

1. An expression vector comprising the gene cluster of SEQ ID NO: 2 or a variant or fragment thereof wherein the variant or fragment encodes proteins with at least 90% amino acid sequence identity to SEQ ID NOs: 4 to 22.

2. A cell comprising the expression vector according to claim 1.

3. A method for producing a cell that harbors the expression vector of claim 1, the method comprising transforming a cell with the expression vector.

4. The method according to claim 3, wherein the cell harbors the tomaymycin biosynthetic gene cluster of SEQ ID NO: 2.

5. The method according to claim 4, wherein the cell is a *Streptomyces* strain.

6. The method according to claim 5, wherein the *Streptomyces* strain is selected from the group consisting of *Streptomyces achromogenes* var. *tomaymyceticus*, *Streptomyces* species FH6421, and *Streptomyces albus*/pStW102tc.

7. The method according to claim 3, wherein the cell is capable of producing 11-de-O-methyltomaymycin.

8. The expression vector according to claim 1, comprising the nucleic acid sequence of SEQ ID NO: 3.

9. The cell according to claim 2, wherein the cell is a *Streptomyces* cell.

10. The cell according to claim 2, wherein the cell is a *Streptomyces albus* cell.

* * * * *

SEQUENCE LISTING

```
<160> NUMBER OF SEQ ID NOS: 22

<210> SEQ ID NO 1
<211> LENGTH: 25954
<212> TYPE: DNA
<213> ORGANISM: Streptomyces achromogenes

<400> SEQUENCE: 1
atggaaagca attccccgtc attatcgacg gaagagtcga cggaaaagct ggaagccgca      60
ttgcgggcgg gaagtccacc gacccaggac ccccctctcg tcctgacgac cctcttcgca     120
cggacggtcc gcctgcacgg cggggccgtc gccctcgcg acgcgcgga acgcttcacg      180 tacgaccggc tcaaccggcg ggccaaccgc atggcccggc acctccaggg tcgcggcgtc     240
ggcagaggcg accgtgtcgg agtgcacatg caccgctctc ccgacctcta cgcggtcatt     300
ctcgcggtcc tcaaggccgg aggctgcgtg gtcccgctcg accccgccca tcccacgcag     360
tacctcgctc gcatcctccg cgaggcccgc ccgtcgccgt gatctgcga cgaccccgac      420 gacctgccct ccgaggcccg gcggcgcg ctctcccggg acgacctggt ccgaggcagc       480
gagggactcc ccgacggcga ccccgatccc ggcaccggcc cggaggacac cgcgttcctc     540
atgtacacct ccggctccac cggccggccc aagggcgtac ggatcgcgca ccgcgggctg     600
gcccggctcg gcccccacag cggcccccct gacatcggcc cccggacgg cctgacccag      660 tcggccgcgt tctcgttcgc cgcctcgacc atcgagatct ggctcgcgtt cctgcacggc     720
gccaccctgc tgccgatgcc cccgggactc ccctcgctgc cggtgctgcg cgaggccgtc     780
gaggagcgcg gcgcgaccgt gctcagcctc ccctgcggcc tgttcaacgc cctggtcgac     840
caggagccgg agtgtctgcg ctcggtgcgc atcgtgctgc tcagcggcga cttcccttcc     900
cccgaccact tgcgccgcgc cctcgcgcac accgacgcgg tcgtctacaa cggctacggg     960
tgcacggaga actcctccat caccgctctg caccccgctga cctcgcccga cgacgtggac    1020
gggacgggcg tcgtcccgat cggccgcccg ctgccgacgg tcaccctgga ggtctacgac    1080
ccgtcgatgc gcccctgcga cgccggcgag gtgggcgaac tctgcgtggg cggcgccggc   1140
gtcgccctcg gctacgccga ccagccggag ctgaccgccg agaagttcac ccgggacccg    1200
gacggcgacg gactgctcta ccgcaccggc gacctcgcgc ggcggaacga caacggcgac    1260
atcgtgctgg tggggcgggg cgacagcatg gtgaagatcc gcgggttccg ggtggagacc    1320
agcgccgtga cgctggccgt gcgcgccctc gacgggtcg cggacgccgc cgtcaaggcc     1380
ttcgaggacg aggacacaca cgagaagcga ctcgtcgcct tctacaccac cggcgacggc    1440 tgccggccg acccgcgga cctggtccgg cggctctccg cggacctgcc ctcccacatg      1500
gtcccctccg cgttccggca cctggagaaa atgccgacga acgtgaacgg gaagatcgac    1560
cgcaccgcgc tcaccgtgga atcccggaag aacaggaaaa tccggaacaa caggaacgag    1620
aaatccgaga aaggcgagaa gaccatgcag aaccccctcg aagctgtcgt cctccagtcc    1680
```

```
tggatcgaga tctccggaat ggacgacttc tcgaccaccg actccttcct gggacacggc   1740
ggtaattccc tccacttcgt gcagctggcc tcccgtctcc agaagatatt cgggatcgag   1800
atcaccaccg agtcggtctt ccggcacggc acggtcgagc agcttgcgcg tttcatcgag   1860
gagtcccgcg accaggcggc caccacctcg tcgtcgcacg gctgacggag acccgacagc   1920
gcccggcacg cgcgccgcgc cggtcgcccg acgtctccgg agggggcgga ccgtgaacaa   1980
ccctttgacc tcggctgttc tggacctggc caggagaaca ctcggttccc ccggtctcag   2040
gcccgacgag gccttctccg accactgcgg cgaccccgcg ctgctggagc agctgggcgc   2100
ggtgctgcgg gcggtgttcg ccgtcgaccc gccggccggg aacggctgg gcgcgcagag   2160
cgcggcggcc gtggccgagc ggctcgcgcg gggccgctcc ggctccggcg gacaggagct   2220
gacggccggg tccgcgccgc cgcacggcgc tacgacggag gcctcgttcg gccagagcgg   2280
catctggctc atcgaccagt acctgccgac cccgcaggcc tacaacgggc cgttcctgac   2340
gcggctgccg ttccggctcg acggggaacg gctgcgccgg gccgtcgccg gggtgctgcg   2400
gcgccaggaa gtcctgcgca ccacctacgc gttgcgcgac gcccggctcc tccaggtcgt   2460
ctccgacgac gacacggtct tccactacgg cgtcgagcac tacggcgacg acaaggaact   2520
cgacgcgctc gcccggcggg tggccaacac ccgcctcgac ctggagcacg gcccgtggt   2580
ctcggtgacc tgtgcgctcg gtccgggtgc ggagagcgcg atcgtctgca acatccacca   2640
catcgcctcc gatgccgcct cggccgggat cttcctgcgc gaactcctcg acgcctacga   2700
ccgcaccggg cggggcctgc cggtggaggc cgtgccggga cgcccgcagt acgccgactt   2760
cgcggagtgg caccgcaggc acctcacgcc cgagcggacc accggttgc tcgacgagtg   2820
ggccgaccgg ctcgccgggg acctgcccgt gctggccctg ccctccgacc ggccccggcc   2880
cgccgcgcag gaacaccggg gcggcaccgt cccgttacgt gtcccggccg gggtgaccga   2940
gaagctggaa cggctcgcgg agcgcgaggg cgtcacgctg ttcatggcac tcctcgcggt   3000
gtacggcacg ttcctcgcca agctgagccg tcaggagcgg gtgctgatcg gctcgcccgt   3060
ctccctgcgg gacgacccgc agaccaagga cctcgtcggc tacttcgtca acatggtcgt   3120
gctgcgtcag gacgtgacgg gcgcgatgac cgtgcgcgag gtgctggggc gggcgcgcga   3180
ggaggtggcc ggcgcactgc ggctgaagtg gccccccttc gacaaggtcg tggagcggct   3240
gcggcccgac cgcaccggcg ctcacacgcc ggtcgtgcag acgatgctcg tcctgaccga   3300
tcccggctcc gcccaagtca tgcacggagc aacgtcattg accatccggc gtgacatggc   3360
gcacggcgcg aagtacgacc tgtcggtggt gttcgcacgg gaggcggccg gctgctcgg   3420
gagcctggag tacgacgcgc acctcttcga cgaggcgacg gcgcggagca tgggcgaacg   3480
gctgggccgg ctgctgaccc ggttcgccga ggcggcgccg gacaccccgg tccgcgatct   3540
cggtctgctt gccgccgacg aggagcggga ggtgctggcc cacgacgacc gtgtggaccg   3600
ctcggcgcct ccggtgccgg tggccgagct gttcgagcgg caggcggcgg cgaccccgga   3660
cgccgtggcc gtgacggacg gcgcccacgg gtggacgtac cgcgaactgg acgagcgggc   3720
cgaacggctc gcgcgggttc tgcgcgagga ggggcggcg gcgggccgcc gggtggcgat   3780
cgccctgccc cgctcggtcg agatggtcgc gggactgctc gccgtcgtga agtccggggc   3840
gtcctacgtg ccgctggacc cgtcgcaccc gccggagcgg gtggcgtacg tcctggacga   3900
cgccgaggcc ctcctcgtcc tcaccgacag cgccacggcc gatcaacttc gcctggtaa   3960
aaggctgttg gagatcgacc gggaggcgga ccggatcgcc gccgccgacc ccgcgccgct   4020
cggcccgacc cggacgcccg acgacgagat ctacgtcatc cacacctccg ggtcgaccgg   4080
```

```
cgcccccaag ggcgtcgtca tccgggaccg caccgtcggc aacctggtcg ccgcccagca    4140
ccggatcagt ccctgcgggg cgacgggcac caccctccag tacatgacgc tctccttcga    4200
cgtctccgtc atggagatcc tggggacgct ctgcgtcggc gggacgctcg ccctgatccc    4260
cggtgaactg cagaaggacc tgcaccggct ggccgcgttc gtcgccgagc acgacgtcac    4320
ccgcctgtac ctgccgtaca tcgcgctcca gcggttcgcg gcgctcgccg tcgcggagga    4380
cctgcgctgc gacgcgctgc gcgaggtgac ctcggtgggc gaggcgctgg tcgtctcccc    4440
gcagatccgg gagttcttcg cccggcaccc ccgcgcccgg ctgctcaaca tgtacggccc    4500
gtccgagacc cacctcgcca cctggcacga gctgtcgggc gaccccgccg actggcccga    4560
ggccgcgccg atcgggcggg cggtcgacgg gatgcggctg cgcgtcctcg gcccggaccg    4620
cgaactcctc ccgccgggcg tcacgggcga gctgtacatc ggcggccgt acctgtcgcc    4680 gggctaccgg ggccggctcg aggagacggc acggcgcttc ctgcccgacc cgtacggcgg    4740
cgacggcgag gtgatctacc gtacgggcga cctcgtccgg tggaacgccc gcggcgacct    4800
ggagtacctg ggccgcgccg acgaccagat caagattcgc ggctaccgcg tggagcccag    4860
cgaggtcgag gccgccctcg acgccctcga cggggtgcgc gactcggcgg tggtcgcggt    4920
cgagttcggg cccggcgacc ggcggctggt ggccgccgtc acgggcgacg cgccgacga    4980 caccgtacgg ctgcgggccg cgctcgccga gcggctgccg gagtacctgg tgcccgcgca    5040
cctggtccgg ctggaccggc tgccgaccac gcccagcggg aagatcgacc ggggcgggct    5100
ggccggacgg ctggccgcag aggtgcgcga ccggggcgcc gacgcgggcg ccaagacggc    5160
acaaccgccg cggaccggga ccgagcgcgc gatcgccgat gcctgggcgg acatcctggg    5220
cggcggtgtc cccggacgcg acggcgactt cttcaccctc ggcggcaaca gcatcatcgc    5280
caccgaactc gtctaccggc tgcggacgtt gttcgaggtc gacatcccgc tgcgaaccct    5340
gttcgacaac ccgacggtcg ccgggatggc cgcgcggatc gacgagcggc gggcaggcga    5400
caccaccgcc ttcacggagc ccacggccga cctgcgcgcc gacgtgaccc tgccggacac    5460
cgtccacccc ggcgaccgga caccggtccc gccggacgcc gcgacccggt tcctgctgac    5520
cggcgcgacc ggcttcctcg gctgctggct gctgcgggag ctggcgaccg tccccgggca    5580
caccgtcacc tgtctggtgc gcgccgacga cgcggacgcc gccctggccc ggctgcacac    5640
cacggccgac cggtacggca tcaccggtgg gatcgactgg gaacgggtgc gcgccgtccc    5700
cggcgacctg gcccggcccc ggatgggcct gtccgacgcg gaccacgacg agctggccga    5760
gtcggtcgag gcggtccacc acgcggcagc gcacatcaac ttcgtgctgc cgtacgcctc    5820
ggtgaagccg ccaacgtcg acggcctgcg ctccgtactg gagttcgccg ccaccggacg    5880
gctcaagcac gtgcaccaca tgtcgaccgt cgcggtgttc gccccggcc gcgagggtgg    5940 gacgatcacc gaggaagcgg tgcccgacag gtgtgagggc ctcggcatcg gctacacgca    6000
gagcaagtgg gtcgccgagg gcatcgcccg gctggcgcgg gagcgcggga tgccggtgac    6060
cgtctaccgc atcggccgga tctccggcga cagcgttacc ggcgcctgcc aggccgacga    6120
cttcctgtgg cggcagatca agagcttcat cgaactcggc tcggcccgc cgccgagga    6180 actcaccacc gacctgctgc ccgtggactt cgtcggccgg gccgtcgccg ccctctcccg    6240
cgagccgtcc gccgacggcg ccacgtacca cctgttccac ccgcgcggct ccgacttcac    6300
ccccgtgcac gccgccgtcc gcgactgcgg gcacccgctg gacacggtgc ccgccgagga    6360
gtggctgaca cgcctggagg agtcggcccg ccggcccggg ggcaacgccc tcgccgcggc    6420
```

-continued

| | |
|---|---|
| agtcccctg ttccgggagg gcgcgctcga actcggcgag aacacctacg gcaacgagcg | 6480 |
| gacgacccgg ctcctcgacc gtctcgggct gcgctggccc gacatcgacc gccggtccct | 6540 |
| cgcccgcatg atccgctggt tcgaagcggc cggtgagctg gacgaccggg cccttgcgcg | 6600 |
| acagggcgcg tagaccgggc cgcccagcgg ctcccccacc cagacatccg caggcggtca | 6660 |
| ccctccctgg ccgctcataa cgaaggccga cagcatgtct cgatacccct ttccgggcgc | 6720 |
| cggacacgac ccgttgatcg cctctatggt ggccgctctc cccgcccgcc agcagcccca | 6780 |
| atggcccgag ccctcccgcc tggccccgt gcacgagcgg ctggcccgcg agtcgccgct | 6840 |
| ggtgtcgtac acgagcgtcc gcgagctgcg cgggctcctc gcgcgggccg ccagggcga | 6900 |
| gttctgcctc atccaggccg gtgactgcgt ggagctgacc accgagtgcg aaccctgcga | 6960 |
| cgtcgaacgc aaggtggaga tgctcgacgt cctcggcgac gtcatgcgca ccggctccgg | 7020 |
| tctgcccgtc gtgcgcgtcg gcggatggc cgggcagttc gccaagcccc gctccgacga | 7080 |
| ctgggagacc gtcccggcg gacgctcccc ggtgttccgg ggcccggtcg tcaacgcacc | 7140 |
| ggacgcctgc gaggaggccc gcacaccga cccgtcccgc gtcatcaccg gactggaggc | 7200 |
| cgcccgctgc gccgtcaccg ccctcgaccg gctcggccgc ggcgagggcg ccgctcccga | 7260 |
| ggagcgggtg tggaccagcc acgaggcgct cctgctcgac tacgaactcc ctcaagtccg | 7320 |
| gcggcacacg gacggcggca gctatctggc ctccacgcac tggccctgga tcggcgagcg | 7380 |
| cacccggcag gccgacttcg cacacgtgcg tctgatgacc gagctggaca cccggtggc | 7440 |
| gtgcaaagtc gggcccgagg cgaccgtcga cgaggtgctg gacctgtgcg cggtgctcga | 7500 |
| cccgcaccgc accccgggcc ggctcaccct catcgcccgg ttcggcgcgg accgggtcgc | 7560 |
| cgcactggcc ccgctggtac gggcggtgcg gcaggccggg cacccggtgc tgtggatgtg | 7620 |
| cgacccgatg cacggcaaca ccgtgaagac gcccgacggg ctgaagacgc gacgcctcga | 7680 |
| cacgatcatg tccgagatcc ggcagtgcgt ggacgtcctg gcggagaacg gggagcggtg | 7740 |
| cgcgggctg cacctggagg cctcccccga cgacatctgc gagtgcgagg gcgcgggtcg | 7800 |
| cgtccccgtc cgcgggccgg gctaccgcag cctgtgcgac cccggctca gcctcgtcca | 7860 |
| ggccgtcgcc gccgtcgcgc actggcggct gcccgtgggg gcggcggccg tatgaccgcg | 7920 |
| cccccgcca ccaccgccgc tccggcgcag gcccacgacg cgctgctgcc gccgccgggc | 7980 |
| cacccttcg cggtgctgca ccgctccggc gccggccgcg cggcaccggt ggagatcctc | 8040 |
| agcggcccgg tacggcgcga ggacgacctg gacgccctcg gcctggaccg gcccggcgga | 8100 |
| gcgaagcggt ccacggacgg cggcgcggac gccccggaca cctcgtcct cgcccctac | 8160 |
| cggcagatcc gggagcgcgg cttcgcgcac cccgacgacg gcgagccgct gctcgccatg | 8220 |
| gaggtgcgcg agcaccggag ggtccccctc gaccggctgc tggcctgcct gccggaccgg | 8280 |
| gcgccgcggg tggaggacac ccgcttcgac gtcgacgacg acggctacgc ggcggccgtg | 8340 |
| gacggcatcg tccaccgcga gatccaccgc ggcgagggct ccaacttcgt gctggcccgc | 8400 |
| agcctgcacg gccgcatccg cgccttcgac cgcacgccg ccctcgcggt gctgcggggg | 8460 |
| ctgatgacgg ccgagaccgg cgcctactgg acgttcctga tcttcaccgg cgaccggtac | 8520 |
| ctgatcggct cgaccccgga gcagcaggtg cgggtgcggg gcgacctggt cgagatgaac | 8580 |
| ccgatcagcg ggacctaccg ctaccgcgg accggcgcc acctgccggg gctgctgcgc | 8640 |
| ttcctgcgcg acccccaagga gaccgacgag ctgtacatgg tcgtcgacga ggaactcaag | 8700 |
| atgatgcgcg ccctgtgcgg cgacgaggtc cgggtcagcg ggccgtccct gaagtggatg | 8760 |
| tcccggctcg cgcacaccga gtactacctc tccgccgct cggaccgccc gctcaccgag | 8820 |

```
atcctccgca ccacgatgcc cgcgccgacc gtgacgggca gcccggtgga gaacgcctgc   8880
cgggtgatcg agcggtacga gccgcgcggc cggggctact acagcggggt catcgccctg   8940 ctggccgcg agggcgggca gcggcggttg gacgcggcgc tgatgctgcg catggcggac   9000 ctcggggcg acggcaccgt acggctgacg gcgggcgcca ccgtcgtacg ggagtcggta   9060
ccggcgcacg agacggcgga gaccaccgcc aagctgtcgg gtctgctgga cgcgctgtcc   9120
ggtcggcggt cggcgaaggc gccggtgccg gcgtccgccg cggggctggc cgaggccggt   9180
ccggtgcgcg gcgcgctggc cgcccgcaac gacgggctgg cggcgttctg gctgcgcggg   9240
accggcgacg tccgcgccgc ccgggccgtg gcgggcgccg acgtcacgat cgtcgacgcc   9300
gaggacgggt tcacgtcgat gctcgcctac caactgcggt cgctgggctg ctcggtgcgg   9360
gtggtgccct ggaccggac ggcgggcggg gtcgccgggg cgcgggcgt ggtcctgctc   9420 ggaccggggc cggcgatcc gcgggacacg gccgatcccc gggtgcgggc cctgcgggcc   9480
acggcccgcg aacggctcac ggccaggctg ccgttggcgg cggtctgcct gggacaccag   9540
gtggtgtgca cgctgctggg gctgcgggtg gcccggctgc ccgacccggc gcagggccga   9600
cggctgcggg tccgctgtg gggcaggcc gccggccg gcttctacaa cagctacgcc   9660
gcgcgggccg acggcgaccg gctgcacccg ccgctgggcg acgggccggt gcaggtgcag   9720
cgcgtcggcg acgaggtcat cgcgctgcgc ggcccgcc tgtccaccat ccagttccac   9780
gcggagtcgt tcctgaccga ggacggcccc ggcatcctgg ccgacctgct gaccggcgcc   9840
ctggcaccgg ccgcggcacc ccggccggc gtccacgaca cgacggggc cggtgtccac   9900 gacaccggac tccgggagtc caggggacc catgagcatg cctgagcgag ggggcgtgga   9960
caccgcgccc cgtccgatcg acccgcgcgc cctgcgcagt tgcatgggcc agttcgcgac  10020
gggggtcacg gtgatcacct gccgccgcgg cgacctcgtg cacggcacga cggtcaacgc  10080
gttcacctcg gtgtcactgg acccgccgct ggccctggtg gcgttggacc ggcgcagtcg  10140
ggcgggcgcg ctgctgcggg agaacggcga ctacgtcgtc aacatcctcg acgcctcgca  10200
gcgcgatctg gcgatgcact tcgcaggtcg gcccatggcg gagccggtgc cgtgggtgga  10260
cgaggacggg ccgcacccgc ggctggcggg cacggtggct catctggtct gccggccctg  10320
gcagatccac gacggcggcg accacacgct gcacatcggg agcgtcgagg agttcgagag  10380
ccgtccggga cggccgctgc tgttccacg cggcgccttc ccggagctgg cgccggacga  10440
ctccgccgtc gcctggtcgc tgtgcctgga cggcatgaac ccggtgacgc acctcccggt  10500
acccgaagag cccgacagag ccgacaggac agacaggaca gacaggacag gggactgacg  10560
tacatgacgg acacaaggca cagcacgggc gcgacgggcg cccccggcac cgggaccacc  10620
ggctccgcgg gcgccaccgg tgatgcgcg ccgccgca cgaccgccc gatgaccggt  10680 gacgagtacc tggagagcat ccgcgacggc cgggagatct gggcgtacgg ggagcgggtc  10740
gacgacgtca ccaagcaccc ggcgttccgc aacacgcgc ggatgacggc tcggctgtac  10800
gacgccctgc acgacccgga gcaccacgac acgctgacca cgccgaccga caccggcagc  10860
gacggctaca cgcacaagtt ctaccgggtg ccgcgcagtg tggaggacct ggtcggcgac  10920
cgggacgcga tcgcttgctg gcccggatg acgtacggct ggatgggccg cagccccgac  10980
tacaaggcga gcttcctcgt cactctcgga gcggacccgg actactacgg ggagttcgcg  11040
gacaacgccc gacgctggta cgcggaggcg caggagcggg tgctgttctg gaaccacgcg  11100
gtgatcaacc cgcccgtgga ccgcaaccgg gcgccggacg aggtcggcga cgtgttcgtg  11160
```

```
cacgtcgaga aggagtgcga cgacggcctg gtggtcagcg gcgcgaaggt ggtggcgacg   11220
gggtcggcgc tgacccactt caacttcgtt gcgcactacg gactgccggt gaagaagaag   11280
gagttcgcgc tcgtcgcgac gctgccgatg gacgcccggg gggtgaagct gatctgccgc   11340
cagtcgtacg agctggccgc gaaccggatg ggcagcccct tcgactaccc gctgtcgagc   11400
cgcctcgacg agaacgacac cgtcttcatc ctggacaagg tgaagatccc ctgggagaac   11460
gtcttcatct acgcgacac cgcgaaggcc gggaccttcc tgaacacgtc cgggttcacg   11520
caccggctca ccttccacgg cgtgacccgg ctcgccgtga agctggactt cctggccggt   11580
ctgctcctca aggggctgga cgtgaccggc acgaaggatt ccggggcat tcagaccagg   11640 gtcggcgagg tgctcgcctg gcggaacatg ttctggggtc tcagcgacgc catggcgcac   11700
aatccgaacg catggcacga cggcggactc ctgccgaacc tggattacgg catggcatac   11760
cgctggttca tgacgatcgg ctatccgcgg gtccgcgaga tcatcctcca ggacctcagc   11820
agcggcctca tctacttgaa ttcgcacgcc aaggatttcc agaaccccga acttcggccg   11880
catctcgacc gctacatgcg agggtcgaac ggatacgact cggtggagcg ggtcaagctg   11940
atgaagctga tctgggactc ggtgggcacg gagttcggcg gccggcacga gctgtacgag   12000
cgcaactact cgggcaacca cgagaacgtc cgtatcgaac tgctgatggc gcagaccgcg   12060
tccggcctgg tcgacggcta ccggggcttc gccgaggagt gcatgtccga gtacgacctg   12120
gacggctgga cggcgccgga cctcatcggg cccgaccagg catgagcggc ggggcggcac   12180
gacgacgggg gcggcggacg gccggtgtcc ggtccgccgc cgcccccggg gggccgccct   12240
cccgccgggc gtcagcgcgg ggcgggcgcc tcgggccggt cgtccggggc gggcaggatc   12300
acggcaaggg tgaagccgtc gtagcccttg gcgcccaccg tctggatcgt ggtggcgctg   12360
accctgggct ccgcggcgac cttctcgtgg aagcgccgca tcccgcggac gccgccgtcg   12420
gggtcgtccg agtcggcgac ggcgccgccg agcaccacgt tgtcgacgac gatgacgccg   12480
ccgggccggg acagttcgag cgcccagtcg aagtactccg gggtgtcggg cttgttggcg   12540
tcgatgaaga ccaggtcgaa cggctgctcc ccggtcttcg cgaggtcggg caggatgtcg   12600
agcgcccggc cgaccgctg gtcgacgcgg tcggcgacac cggcccgcgc cagatggccg   12660
gcggcggtct cggcgaacga gcgctcccac tcgatggtga ccagccgtcc gccgggcggc   12720
agggcgcggg cgagccagat ggtgctgtac ccgccgaagg tgcctatctc cagaatgcgc   12780
tcggcacgct ggacgagggc cagcaggtgc agcagctttc cctgggagcg ggagacccccg   12840 atatcgggga ggtcgaatcc gatgtgtgcc tgggcggcgg cggccagggc ggggtcctcg   12900
tcaccgagaa ccgtgtcgaa gtagccgtcc accgcgctcc actgatgctg tgtcatgact   12960
ccagtgttcc ccgtgaggag gaaattcggc accctgaagg aaggaattcc agaaaaacgg   13020
cggattcctg tcgtccactt atccgcgtcg gttagtggag cggattttcg ggaattcgcc   13080
tgcctgaacg agaaaaagaa cgtctttcgt ttcccaccag cgaccaccc ctcgatctct   13140 cctggcacga cttcaatgag aggagcgcag tatcttgcag cgaaccggga ccacgacaga   13200
gcgaccgccg aaccccccacc tcggccctga tcccgccccc gatctccacc tcgtaccgga   13260
gctgcaccac gtgggcgtgc agacggacga cctcgacaac tgcgccgcct ggtacgagga   13320
gttcttcggc tgccggacca actggacgct ggacaccttc tccgacctga cgctgagccg   13380
cctgcccgga atcacccggc tgaccgaggt gacggtggcc ggactgcgct tccacctctt   13440
cgagcgcacc gggcacgacg gcgccgtccc cggtgccaac acccgccagt tccagcacgt   13500
ctgcctcgcc accggctccc ccgaggagct gcgggcctgg cgcgagcgct ggttccggct   13560
```

```
gtacgagtcc ggccggttca cgttcgccgg tgacgaggag cccaccgaca tcgtcatcga   13620
cgacgacggc gtccagagct gctacgtcct ggacgtcaac ggcctggagt tcgagttcac   13680
ctacgtgccg ccaggaggag accgatgagc atgcgcgccc cccgcaccgt gaccgaactg   13740
ccggtgcccg acggctggga cttcggggac ttccccctacg gcctggaacc gctgacactg   13800
cccgagccgc cgacgccggg aacggagacc gcgatctcgg acgtgctccc cgccgacacc   13860
tcccgcgtgc ggagcgccag gccgtgcccg cgcacggggc cggcgctcgc cgccgaggag   13920
atctcccacc agctgttctg gttccgctgg atcacgggac accaagccac cttcgccatc   13980
tggcagttga cggcgcacgc cctgcaccag gcccgctccc gttccgaccc cgcgccgtcc   14040
cttcgggcga tgacggacct caccgacgcc tacaccgcga tgctgctgta caccagttcc   14100
tgccccaccg acgtctacgg cacggtgatc cggccgagca tgtacctcca gcaccgcagc   14160
ttcagcggca cctgggcccc ggacttcgtg cccgtgcgct cgctgctgcg gggcaagaag   14220
accgagtggg aggggacgcc ggaggccgaa cggctgaaga aggcggtgca gatgtatcac   14280
agggtgcacg cgggggtggc ggccaagctg gttccgggcg gccgttcgct gctccaggag   14340
tcggccgcgg aggtcgcacc gacccgcccc gagacccagg cgctcatcta cgaccactac   14400
ttcctgaccc tgcggggccc ggtcgacgcg acggagctgg tcggccagtt gcggagccgg   14460
ctgcgggcca tcacgcagga cgtggcgacc aacggcctct atcccggcct cagtccgcag   14520
gaggacgtcg ccttccccga ggaactgcgg ggcgacgagg tacgccaggg gtacgaggag   14580
ggcttcgcgt cggtcctggg ccggatcgac gccgccgccg ggcagctcag gccgcgggtg   14640
ctgcaccaca gcgcccctg acgggacggc gtccggcacg acgaggccgg acaacgtccg   14700
gcacgtcgga gcacgacggc atccggtacg acgaaggagg agtacgcgtg cggcacggag   14760
tggtgatcct tcccgagcgg cgctggtcgc gggcgcgcga gcagtgggtc ctggccgagc   14820
ggctgggctt cgaccacgcc tggacctacg accagttgat gtggcggtgg ctgcgggacg   14880
agccctggtt cgcctgcgtc cccaccttcg ccgccgccgc ggccgtcacc tcgcggatca   14940
cgctgggcac gatggtcgcc acgcccacct accgccatcc ggtgacgctg gccaaggagg   15000
tgatgtcgct ggaggacgtc gccggaggcc gcttcgtctg cggactgggc gcggggcgg    15060 gcggcctgga cgaccgggtg gtggacccca ccgagcggac cccgcgcgag cgcgccgacc   15120
ggttcgccga gttcgtcgag cgctggacc tcctgctcac cgagcggagc gcctcgtacg    15180
cgggcgagca ctacgccttc gacgacgtgc cggtgaaccc cggttgcctg acacggcccc   15240
gcgtgccgtt cgccgtcgcc gcgaccgggc cgcgcgggat cggctcgcg gcgcggcggg    15300 cggacacctg ggtgacggcc ggtccgcccg ccgtttcga cgccctgccc tacgagaagg    15360
cgctgcccga catcgcccgg cagctggacg agctggacgc cgcctgcgag cgaccggcc    15420 gcgacccggc cacgctggac cggctgctgc tgaccggcgc cctggtcggc ggggtgctcg   15480
actccgtcga gtcgttccgg gacgcggtgg gccgcttcgg cgagctgggc gtcaccgacc   15540
tggtcgtgca ctggccccgc gcgtcgttcc cgtacgaggg cgacccgcgt gtgctggagg   15600
ccgtcgcgga ggaggtgctg ctccccggac gggaggcggc cccgcagacc gggcccgtgt   15660 cacccccggcc gggcagcgcc cccagtggcg aaggagagcg acgttgatcg cgtacgagat   15720
cgtcgacatg ttcacggaca ccccgtacgg cggctgcgcc ctcggcgtcg tccccgacgc   15780
ggcggcgctc tccacggcgg acatgctggc cgtcgcgcgc gagaccgccc tgacggagac   15840
ggcgttcgtg gtgccgccgg ccctgccggg gtcgacgtac ggagtgcggg tgatgacccc   15900
```

```
ggacggggag tcgccgtacg gcgggcacag cgcggtgggc accgcgagcg cgctcgtgcg    15960
cgccgggcgg ctcgcggccg gggaggcggt gcaggagtgc ggcggccggc agctcgccgt    16020
gaccgccggg gccgacggct ccaccctgtc cgtcgcgggc gagccgctgc tgcggcccga    16080
gtgggacccc ggcccgctgc tcacggcgtg cggcctgacg gacaccgacc tgacgggcac    16140
tccgcgtctg accggcttcg gaccggcgtt ccacgtcctg ccggtgggcg cgaaggccct    16200
cacgcgcgcc gcggccgacc tgaccgaccc ggtctgggcg gactgcccgg acgcggtgct    16260
cgtcgcctgg gaccaggccg gccgcaccgc ccgcgtccgc gtgttcgctc ccggttacgg    16320
catgcccgag gacccggcct cgcgctccgc cgcgctgggt ctcggcgcct ggctcgccga    16380
ggagaaggcg ctccccggcg cggacggccg ccacgcctac caggtccgcc aaggcgaggg    16440
cctcggccgc ccggccaccc tctcctgcac cgtcgacctc accggggggcc gggccaccgc    16500 cgccacggtc cacggccggg tcaccctcac cgcctccggc cggatgacac cccccggacg    16560
cccctgaccc cccgctcccc ccctgcggtc cgaccgtacg accagaaagg atcttcccag    16620
gtgctcttcc gaccggaact gcacggcacc cgcggtgccg tcgcctccac ccactggctg    16680
gcctcccaga cgggcatgtc catgctggac cgcggcggca acgccttcga cgccgcgacc    16740
gccgccgcct tcgtcatcca ggtggtggaa ccgcatctca acgggccggg cggcgacgtc    16800
ccgatcctcg cccatcgctc agggaccggc tcggtcgacg tcgtctgcgg gcagggcccg    16860
atgccggccg cggcgacgcc ggaggccttc accgagcggg gcctggccgt cgtccccggt    16920
tccggacttc tgcccgccgt cgtccccggc gccttcggtg cctggctccg cctgctcaag    16980
gagtacggca cgctgcccct ggaggacgtg ctggaacccg ccatcggcta cgccgagcac    17040
ggctacccgg tgctgcccaa gtgcgccgcc atgatcggcg cgctcacgga gctgttccgc    17100
gacacctgga cggagtcggg ccgcacctac ctgcgcaacg gggtcgcccc gcgcgccggg    17160
gagcgggtca ccaacccggc gctcgcgcgc acctaccggc ggctggtcgc cgaggcgaag    17220
gcgtccgccc gggaccgcga gggacagatc gacgcggcga cggaggcgtt ctacaccggc    17280
ttcgtcgcgg aggccgtcga cacctatctc gccaaggccg aggagatgga ctccaccggc    17340
cgccgcaaca gcggcctgct caccggcgcg gacctcgcgg cgtggcgacc gcgtgtggag    17400
cgtcctctga gcctcgacca ccgggacctc accgtgcaca aggcgggccc ctggtcgcag    17460
ggtcccgtct tcctccagca gctcgccctg ctggccgacg ccgacctcgc gcgaccggc     17520 ccggagagct cggagtacgt ccacacggtg gtcgaggccg ccaagctcgc cttcgccgac    17580
cgggaggcct ggtacggcga cccggaccac gcagacgtcc ccgtcggcgc gctgctggac    17640
ccggcgtaca ccgccacgcg gcgggcgctg ctcggcgcgg aagcctccta cgagctgcgg    17700
ccggggcggc ccggcgggcg cgagccgctg ctgccgccgc tgcacgacga gagcgtcgcg    17760
cccgccgacc cggcctggct gggcgagctg gagcagggca tcccggcgat catgaagctg    17820
accgcggcga ccggcgacac ctgctgcgtg agcgtcaccg acgcggcggg caacatggtg    17880
gtggcgacgc ccagcggcgg ctggctgaag agttccccgg tggtgccggg gctgggcttc    17940
ccgctgggta cccgggggaca gatggcgacc ctcacccccg gccaccccaa cacggtggcg    18000
cccggcaagc gtccgcggaa ccacgctgag cccgaccttg gtcctgcggg acggccggcc    18060
gtacctggcg ttcgggacgc cggggcggcg accagcagga ccagtggacg ctcagcttct    18120
tcctgcacca caccgagcac gggaagggcc gcaggcggcc gggggggatc gaggcgcgca    18180
ccttccacac cgatcacgtg cccacctcct tcgccccgcg ccggttccgg ccgggcaccg    18240
tcgtcctgga gggcggctgg cccgcggcgg aggtcgaggc gctccggcgg cgcgggcacc    18300
```

```
aggtggacct ggtgcccgac tactcgctca gcaaggtgtg cgccaccggg ctgaccgccg    18360
acgggctggt tctcggcgcc gcgagtccac gcggcgcgca ggcgtacgcg gtcgcggggt    18420
aggagaggag gacaggaaat ggtttccatc aggaaaccac ccctccgagc gcggaaggtg    18480
ctgacaatgg cggctcaccg gaagaaccac agtggggact tcatcgtgct gagcgaggcc    18540
cggcagaaca atctcaaggg cgtcgacctg cgcatcccca aggggaagct gaccgtcttc    18600 accgggtct ccgggtcggg gaagtcctcg gtggtcttcg acacgctggc gatcgagtcg    18660
cagcggcagc tcaacgagac cctgccggcc ttcgtccgcc accggatgcc caagtacgaa    18720
cggccggacg cggggggtgat ggagaacctc tccacggcga tcgtcgtcga ccagcggcag    18780
gtcggcggca acgcccgctc cacggtcggc acgatgaccg agatcctgcc catgctgcgg    18840
gtgctgttct cccgcgcggg cacgcccagc gcgggcccct cgcacatgta ctcgccgaac    18900
gacccgcgcg gcatgtgcga ggagtgccag ggcctcggca cgacggtccg tctggagctc    18960
gacaagctgc tcgacgagga caagagcctc aacgagggg ccatccgctt cccgtccttc    19020
gccgtcggca ccttccagtg gcagctgtac ggcgagtccg ggctcttcga ccccgacaaa    19080
cggttacgcg acttctccgc caaggaccgc gaactgctgc tgcacggcaa ggggttcacc    19140
gtcgaccggg cgggtcgcaa cggtgtctac aagaacgagt acgagggcgt cgtcgagcgc    19200
ttcacccgcc ggtacatcac ccccggcctc gaccacgcca agagcaagga gcgcgcggag    19260
atcgagcggg tggtgaccca gggccctgc cccgtctgcc acggcggacg gctcaacaag    19320
gccgccctcg cctcccgcat cgacggcgac aacatcgcgg acttctcggc catggagatc    19380
accgacctga tcgaacggct ggcccggatc gacgcgcccg ccgtcaagcc ggtggtggcg    19440
ggcgcgcggg ccgcgctcga gcgcatccag gcggtcgggc tcggctatct gagcctcgga    19500
cggcagacca ggaccctgtc cggcggcgag gcccagcggc tcaagatggt gcgccacctg    19560
ggcagcagcc tgaccgggct gacgtacatc ttcgacgagc ccagcgtcgg cctgcacccg    19620
cgggacgtgc gacggatgaa cgacatcctg ctcgccctgc gcgacaaggg gaacaccgtg    19680
ctggtcgtcg agcacgaccg ggacgtcatc gcgatcgccg accacgtcgt cgacatgggc    19740
ccgggggccg gccgcgacgg cggcgaggtg accttcgagg gcaccccggc ggggctgcgc    19800
cgctccggca ctgtcaccgg caagcagctg cggagcgtga ccgggctcaa ggaggaggtc    19860
cgctccccca ccggcgaact gaccgtgcgg gcggcgaagc tgcacaacct gcgggacgtc    19920
acggtcggct tccccaccgg ggtgctcacc gcggtgaccg gagtcgccgg ctccggcaag    19980
agcaccctcg tgtcgaaggt gttcaccgcc cagtaccccg acgccgtcgt catcgaccag    20040
tcctcggtgg ggatctccgc gcggtccaac ccggcgacgt acaccgacat catgggcagt    20100
ctgcggcagc ggttcgcgcg cgcctcgggc gagaagccgg gactgttcag cttcaactcc    20160
gagggcgcct gcccgcagtg cggcggcaag ggcgtcatcg agaccgattt ggccttcatg    20220
gacccggtca ccacggtgtg cgaggcgtgc gacggccgcc ggttcaacga cgaggcgctg    20280
cggcacaccg tgggcggccg gacggtcgtc gacgtcctcg ccatgaccgc cgaggaggcg    20340
tcggacttct tcgacgacgc gcccgtacgc cgcaagctgg ccctcctcac cgaggtcggg    20400
ctgggctacc tcaccctggg ccagcccctg tccacgctct ccgagcgcga gcggcagcgg    20460
ctcaagctgg cgcaccgtct gaaggagacc ggcaccgtct acgtcttcga cgagccgacc    20520
accggtctgc acatgagcga cacgcgccgg ctgctggacc tgttcgaccg tctcgtggac    20580
ggcggcaaca cggtgctggt gatcgagcac gacctcgacg tcgtcaagca cgccgactgg    20640
```

```
gtcgtggacc tcggcccgga ggcgggcagc cagggcggcc gggtggtgtt cgagggcacc    20700
ccggccgagc tggcccgggc gaagggctcg cacaccggcc gcagcctcgc ggcggacctg    20760
cgcaccgccc gtgagcacag ctcgtcctga gacacggtcc cagagcgcaa cccacgacac    20820
agcccgaggg cacaacccag ggacacggta ccggcccacg gtcggacgc gtcccggggc     20880 gctgtcccgg tcaggaccca aggagtcgga gatgcccctc atccgcgtca ccttgctgga    20940
gggccgctcg ccgcaggagg tggccgccct cggagaggcg ctcaccgcgg cggcgcacga    21000
gaccctcggc accccggtgg aggccgtccg ggtgatcgtg gaggagacgc cgccggagcg    21060
ctggttcgtc ggcgggcggt cggtggccga gcggcgtgcc tccccctcgt gacccgctcc    21120
gtcaccgccg cgggccgccc cggagccgcc ggggcggccc gcacgtccgg gagcgccggt    21180 tcagcgacg gcgccccgc gcgggctgcg gtcggcgcgc gcgaagcgct cccgacccg      21240 ctcgacgcgg tccggggacc aggacgcgag gtcgtcgcgg gtgaggcggc cgctgcgggt    21300
gatcagatgg gcgttgaacg cctccggttc gaggtcggcg tactggtcca gttcctcgaa    21360
ccactcctgg ctggtgcgcg cggtgcgctg cacggccgcg acctccggca ggcgttcggc    21420
ctcgtaggcg gcgagcgcct ccggcaccga cccgtggtcg tccagggcca gggcgagcgc    21480
gagggcgtcc tccatggcga gccgggtgcc cgagccgacg gagaagtggg tggtgtgcgc    21540
gctgtcgccg aggagggcga tgcggccgtg gctccagcgc ccgttgcgga cggagacgaa    21600
gcggccccag cgcgaccggt tggtgcgcag gtcgtggccg tccaggacgt cggcgaagag    21660
gtccgcgagc cggtccgtgt cgctcctgcc ggaggcgtcc ggctcaccgg cgtcgccctc    21720
ggtgaagccg gccgcctccc cacccggtc gtcgacctcg gcgatgaagg tgctgaggcc     21780
gggggcgtag gggtaggcgt gcgcgtgcag caagccgtgg tcggtctcgg cgacggcgaa    21840
ggtcagggcg gtgaaggccc gctcggtgcc gagccacaga tagcgcgagc cgcgccgggt    21900
ggtctcggtg ccgaactcct cccgacgggc atcgcgggtc gcggagttga cgccgtcggc    21960
tgccaccacc aggtcgtacg tgcgggccaa ctcgtccgcg tcggggcgc gggtgccgtg     22020 gcggacggtg acgccgaggt cggcacagcg ggcgcgcagg agggcgagca gggcgcggcg    22080
gccgatcgcc gagaagcggt aaccgccgtt gcgcgaggtg cggccccggt ggtggacgtc    22140
gatcctcgac cagtgggcgc accgggcgcc gagcgcggcg aacagcgggg ggtcggccgc    22200
ctcgatgccg ccgagcgccc cctcggagaa gaccacgccg aagccgaagg tcacgtcggg    22260
ggcgttcgcc tcccagacgt cgatctcgct tccggggcgc agccgtttga cgagcgcggc    22320
cgtgtagagg ccgccgggtc cggctccgat gatcgcgatt cgcatgacac ctcacgggga    22380
ctcggtcgag tgacggggtg gcgcgcgcgg gggacggcaa gtggcccctc caacggacta    22440
cgtattgccc atgagagcaa aagtattatc cgcaggaaa ccaatcgcct cgggcggtcc     22500
gccgccgcgc ggccgaccgg gaggggcgc ggccgatgag gccgacgacg gacgcggagg     22560
tgctggagcg gctgtacggg gcggacgtgc cgcccttcgc gctgctgcgc agacagcgtc    22620
ccgacgcgcc cggaccagca ccggtggagc tgctgttcgg ggacgtggac accgggaagt    22680
cgatggggtc ttcggggtct ttggacaacg cggagaccgc cgggtcgctg acggggccg     22740 gtccgcccgg tgccgcgccg gggccgggcc tgctggccct gctgcccttc ggcacctgg     22800 ccgaacacgg cctgccctgc cgtgacgacg gcacgccggt gcgggtcctg cgggtgcgcg    22860
agcaccacgt cctgccggcg gacgcgttca ccgaccctcg ccttcccggc gcggggccgc    22920
tggagtggcg ggacgcgggg ttcacgacga ccgacaccca gtacgaggac ctggtgcgag    22980
ggttcgtcgc ctcggacgcg gcccgcggcg gactgaacgt cctgctgcgc cgcgactgga    23040
```

```
ccgcgcggct gccggacttc cggcccgcgg cggcggtgga cctgttccgg cggttgctga   23100
ccgccgagtc gggcgcgtac tggaccttcg tcctgcacac cggggggcgcg cggccgctca  23160 ccctggtggg ggccacgccg caggggcacg tgggcgtcga gggcggccgg gtggtgatga   23220
acccgctgtg cggcacgtac cggctcccgc cggaaggacc ggacgccggg gacctgctcg   23280
ccttcctcac cgaccgcaag gagtcggagg aactggcgac cacggtggac gccgaactgg   23340
cggtgctgtg cgggctgtcc gggccgggag tgcgggtgga gggccgttc ctgcgccgga    23400 tgtcgcatct gctgcacacg cagtgccgca tcagcgggcc cgcggcagcc ggggcccggg   23460
agaccctcgc gcgcgccctg ttcgcgtcga cggtcgtggg cagcccgtac gccgacgcct   23520
gccgggcgat ccaccgccac gagacgacgg ggcgcggcta ctacggcggc gtcctcgcgc   23580
tgatcggccg cgacgccgcg ggggcggagg agctggactc ggcggcggtg atccggaccc   23640
tggtcgtgga ccaccggggt gaagcgcggc tgtcggtggg ggcgaccgtg ggcggccggt   23700
cctcgccgga ggcggaggcg gccgagaccc gcaccaaggc gcggaccgtg ctgaccgccc   23760
tcaccgcgca accgcccgca gccgcgcaga cgcccgcgcc ccgcgcgccg gtcctcgacg   23820
cggccgtacg ggacgcgctg gaccggcgcc acgcggcgct gtcgtcgttc tggacggagg   23880
gcaccgtcgc cccgccagtg ggcgccgccc cggtgctggt gctggacccg ggcggcgacc   23940
cggtcgccgc actggcggcc ctgctgcacc tggtcaccgc cgtgcacggc cccgccgtgg   24000
tggtccggta cgacgccccc ggcgccgccg agaccctggt ccggcacgcg ggcccgtac   24060 tgctggcgtc cgggccgggc cgcccggacg accccgggtg cgtacggatg gcggcgctgc   24120
gccggacggc cgcgtccctg gtacgggaac ggccgcccgg cgggcccccg gtggccgggg   24180
tgggcctcgg cttccagttg ctggcgctgg ccgccctgcc ggaggccgg gtcgtgccca    24240 ggaccggcgg cacaggactg gcgcgggagg tcgaggtctt cggcaggccg gtcaccgccg   24300
cgttccgcaa cgcccacgcg atcgtgtccg gtccggacgg gcacgaggtg gtcgcgctcg   24360
gcgaacagac cgtgcggggc gtgcagttcc gcccggagtc ggtgctgacg accgacgggg   24420
ccggggtgct gcgccgactc ctcggctgac tccccccggcc cgtcgtcgtc cggtgccgtc   24480
gtctcccggc cccgccgacg caggctcagg acgcgtcggc cgccgcgccg agttccacga   24540
gggtgcgggc cgcggactcc agggcgaagg tcatcgagcc gccgttgggc tcgaacccgg   24600
cgtggtcacc ggcgaagtgg atacgcccct cgggcctgcg gatcaccggc atcagggcgc   24660
tgtgcccacg ctcgggaagg atgtacgccc cttccgcgta cgggcgttgg tcccagcaga   24720
cggacgtgct ggtctcgtag tgctcgcggg cgcccgggag catccgttcg acctcgtcga   24780
gcacgaagtc caggcgctcc tcctcggtca tgaccgacac cgcccgcgcc cgccaccccg   24840
tcatcaggca ctccaggatc ttgcgcgggc ccggagccgg ggggtggcg tcgcgtatcc    24900 accgtatggg caggtcggtg gagaagctgg cgttgcgctg cggccagaac tggcggcgca   24960
tctgagggta gacgcggacg acggacgagt acttcacccg cgcatcacgg tcgtgcttgg   25020
cgtcggtcag gcccgcgtcg gtgaagtcga tgtgccggat cgcgctgaac gggacggtga   25080
cgacgactcg ttcggcctcc agggtctgca tgcgaccgtg ggcgaggacg gtgacccggg   25140
cccgctccgc gtcctgttcg acgcggacca ccggacggcg gtagtggata cggctcttga   25200
ggcgctcggc gaacgcctgc gggaagcggt cggtgccgtg cttgaccttc gcccagcggg   25260
gatcggcgtt gccgagcgag tgcgggctcg cctcgtggcg cagccaggac agcgcggacg   25320
ccgtcttcag gtcgccgccg cgcatctcca ggaagagggg ttccatgagg tcgatggccg   25380
```

```
cctgggaggc gccccgttcg gtgaggacct cgtgcacgga caggtggtcg taggggggcga    25440 ggcgctgggt gaccgcccag tcggggggcgt tcaggtcggg ctggaggccg tcggcgaccg    25500
ccgagacgta ccgctcgatc atcccgccga cgccgagatc cttctcgtgc gggtgcaggc    25560
cgagcccggc ctcggcgacc gactccgggt cggggggtgaa gaaacggccg cgcgcgaagt    25620
aggagaacgt ggtgtcgaag aggtcggcgg tctccgtctc gacgccgagt tcgcgcaggt    25680
agtgcatggc gtagtggcag tgcggggtga gcgtcatcgc gccggcctcg gcatgcaggc    25740
cgtcggcgaa cggctcccct taaggtgtacg cgcgcccgcc ggcccggtcg acgcctcca    25800 ggacggtcac ctcgcagtcc ctcgcggcga gttcgtgggc gacggccagc ccggcgagtc    25860
cggctccgac gacgatgacg gatcgcgggg gccgcagccc cggcagtccg ctgtcgaagg    25920
cacgtcgtac ctcggtctga gtggcttccc gcat                                25954

<210> SEQ ID NO 2
<211> LENGTH: 29067
<212> TYPE: DNA
<213> ORGANISM: Streptomyces species  FH6421

<400> SEQUENCE: 2
ggagcgcgca agatccgacg ggaaccgagc ccccggcccc ctcgtcggcg ttgtcattcg      60
aaagaaatac gtaatgaccg ctcaagtgtg gccaattccg ctccgggcgt acgctggcgc     120
actaaattca gggtcggcgt aagaatcgag cgagggcgga cggagcgttg caggaacggg     180
cgaaagcaac ccgtagatca ctgctggaag cggctgccca gctcttcgcc gaacagggat     240
acgcggccac cagcgtcaac gacatgagcg cccggtcggg ccggaccagc ggcgccgtct     300
acttccacta cgccggcaag gaggccgtcg ccgtcgccgt cgtccaggac cggttcgcca     360
cctggccaca gctcgccgca cgctacgcgg acgaggcggt ccccccggtc gaccggctcg     420
tcgccctcag ctacgacatc gcccacgctc tcgccgagga cccggtgacg cgtgccggcg     480
cccgcctgtg ggccgaacgc gccaccatca acgttcccct tccccacccc ttcgcgctgt     540
ggaccaccgc cgccacacga ctgctcgcga aggcccggct cgccggccac ctccacccgc     600
atgtccgccc cgctcgcgcg gcccggaccc tggtccctgc cttcttcggc ctgtgcgcgc     660
tcaccgagga actcgaaggc acggccgccc tcaccgaccg cctgaccgac tggtggcagc     720
tgacgctgcc ctgcctccgc ccgcaccccgg tgcgcgagga cctgccgcgc gggcggtgac     780
gcgcggcagg tcccgtagct ccggccgctg tcggagcacg ggcggcgcgt tacggggacc     840
gcgccgggta ggccccgtgg ctcaccgctc gcggacaccc tgaacgggga gatgaggggc     900
gcggcttccg ccgtgacgcc gcggtccggg aagccgtggt gttcgaggaa gcccgcgatt     960
gtcgagcccg cgcggcagcg ccggcccctc ggccggacag cgcgtcgcac cgcccgtaca    1020
gcggccacca gcaggtccgg tgggtgcgga taccgggtgg tgcggccgcg cacgcggtgg    1080
gtgcggacgt cgggtggtgc ggcggcgtac gccgtgggga cgggacgggg ggcgtcgcgc    1140
atgcggtggc tgcggatgcc gggcggtgcc gccgtgcatg ccgcgggtac ggacgctggg    1200
tggtgcggcg gcgcacgccg tgggggtggg gcgggggtgc catgggtgcg gacgccgggc    1260
gctgcggcgc cgtacgccgt gggccgggc ggaggtgccg tcacgcatgc cgtggctgcg    1320
gacgtcgggt ggtgccgccg tgcatgccgt gggtgcggac gtcggcggcg gcgtacgccg    1380
tgggccggga ccgggggctg tcacgcatgc cgtggctgcg gacgtccggt ggtgccgccc    1440
tgcatgccgt gaccgcggac gccgggcagt gccgtcgcgc accccatggg gccggggcgg    1500
gtggggcctg ccggtatccg ggtgggggcg gtaccgccca cgccgaccgc gccgcccgcc    1560
```

```
cggcacccccc gcccgcggct cagggacgcg cctccaccgg ttcgaggtgc ggttccaggg   1620
cgccggcgac cttgtggcac agctccacga acatcgcgcg ctcacccggg ctcagtgcgg   1680
cctccacgat gcgggcgttc tcccgccgtt gctcggcgac gcgggtgagg aaggcctcgc   1740
cggccggtgt gagcgaggtg gtgagttcac gccggtcctc gccgagcgtc cgctggtcga   1800
cgagctccag gtccttgagg acgcgcagtg ctttggacgt ggtcgcccgc gacacaccga   1860
gcgaggcact gagcaccgag ggagtcatgg ggccgcggat gcgcagcagc tccaggacgt   1920
cgtactgctg ccaggtgacg ccttccggat tcgagcgagt gcggcgggcg acgaggatgc   1980
actgcaagtg ggaaagcgcg tcctcgagtt cgcctggcac agccgaggtc tcggaggcgc   2040
ttcgtgggct gtcggttcgg gtcatcaacg ccctcaggtg atcaggtcgg ggacgaggcg   2100
ccacggccgg ctcggggcgg gagcgggccg acggcgacct ccgattggtt acccattatc   2160
aacgatcctg gggcggcaac gtatacctct ccacacggtc atgtgatcca tcgcccaaca   2220
gttgttttcca tcgggaaaat ttctacgcga tgatctctga tgagtggccc tccaggccgg   2280
acacgcgccg cgcctcgctc cggcttttcc cggcccgcga gcgggaggcg ccctcgggc    2340
gggcccccgt ggacgcagg gcgccgtcgg ccgggcgctc tggtttgctc cggtcgaaca   2400
atggctgatg catcgtcagt gactcggttg ctttcctggc ggtaaacaag tggctgaaaa   2460
cgcgccctgc gacgctgcgc tccaccgtgt cggcctgggg ttgtccgtgg cggcgaaggg   2520
gcctccggtc ggggcccgac agcccaggca tgggagcgaa gagcgggggt agtggcagct   2580
ccagcgtggg tggcgcagcg gtctcggcgc ctcaagatcg gggttgacac gtcgaagagc   2640
gccgacctaa cgtgatttcc gaacagcaac catcacccttt cggttgatttt gtgcgtattc   2700
cttgagaagc cggtcactgg acgtcggatg tgctcgtcgc tgtgggcgcc ccgtggccat   2760
ccgccagcga ggcaaggagc acgtgtgctc acggagaatg catcaggcga ggcgcgttcc   2820
gctgttcccc tgaccctcac cgagggtttc gaccgcgtgg tgcggccgc cggccaccag   2880
gtcgccctcg tctccggcac ggagaccgtg acctaccggc aactgaacga acgagccgag   2940
cgcgtggccc gcgggctggg cgcccgcaag gtggcgcccg gtgaccgggt cggcgtgtat   3000
ctgcgccggt ctcccgacct ctacgcggtc atgctcggcc tcctcaaggc gggcgcctgt   3060
gtggtgccgg tcaacccgga ccaccctgcg ccgttcgtct cccgcgtggt ggccgaatca   3120
gcgccgcggg ccgtcgtgca cgacgcggga acaccggccg tcgcgcccgc tgctccgggc   3180
gcaccgctgt gggtaccggt cgaggagctc accacggccg cggaaccgga cgacggcgtc   3240
gcgctgcccg ccgtgaacga tccggacagc accgcgttcc tgatgttcac ctccggatcc   3300
accggccggc cgaagggcgt ccgcatcgcc caccgcgggc tggcacgact cggcccgtac   3360
agcggggaac tgcgcatggg cccgcaggac tgcctggtcc agtccgcggc gttctccttc   3420
gccgcgtcca ccatcgagat ctggctcgcc ctcctgcacg gcgcacgact cgtcgtgatg   3480
ccccagggc tgcccagtct cccggccctc aaggacgccg tcgtccggca ggcgtcacc   3540
gcgctgtccc tgccctgcgg tctgttcaac ctcctggtgg acgaggagcc ggaatgcctg   3600
cggggcctga gggtgatcct cctcagcggc gacttcccgt cgccggagca cctcagccgt   3660
gcggcacggg cgacgcgcgc ggtcatctac aacggctacg gctgcaccga gaactcctcc   3720
atcaccgccc tgtaccccat ccgcgatgcc ggggacgtca cccgcgagaa ccgggtgccg   3780
gtgggccgcc ccctgcccgg ggtcaccctg gaggtactcg acgactcgct gcggccctgc   3840
ccgcccggaa cgcccggaca gctcgtcgtc ggcgggctcg gactcgccca gggctatctg   3900
```

```
aacgacccgg aactcacgaa ccgcaagttc gtcaccgggc cggacggacg gccgcgctac   3960
ctgaccggcg atctgcccg cgccaccgag gacggtgaca tcgtcctcat aggccgcgcc   4020
gacagcatgg tcaagatccg cggctaccgc gtcgaactga ccgcggtgac cctcgccctg   4080
cgcgccctcg acgggatcgg cgacgccgtc gtcaaggcgt tcccggaggg cgccggggag   4140
aagtcgctca ccgccttcta caccaccgtc gacggacgac cgctggacgg tgccgacctg   4200
gcacgccgca tggagacca actgccctcc tacatggtcc cctccacgtt ccaccacctc   4260
ggcgacctgc cgagaaacgc caacggaaag atcgaccggt ccgccctcac ggacccgtcg   4320
gacaccaacc gcgatccgaa gaaaggtcac acagccgtgc agaacccgct cgagaccgtc   4380
gtactccagg cgtggaagga catctccggc gccgacgact tcaccaccac cgactccttc   4440
ctcggccacg gcgggaactc cctgcacttc gtccagctcg cctccaggct gcagaagatc   4500
ttcggtgtgg aggtcagcac cgaggacgtc ttccggcacg gcacggtgga gcagctggcg   4560
cgcttcgtcg agcagtcgcg ggacaccgga cgcaaccccg ccgcacagac ccagtaggcg   4620
tcacccggcc gtggccgtgc ggcgcccgtc gccggcggcc ggggcatctc tgcagaggac   4680
tacgaccggt gaactccccc ctccgaacca ccgtgctcga ccttgcacgg accaccctcg   4740
gcagcgccga cctcaccgcg cacgaaccgt tggccgaccg gtgcgaacac ccggccctgc   4800
tcgacgacct cgccaccacg ctgaccgccg tcttcgcggt cgagatcacc ggcgcggacc   4860
tggcggccgg tgccaccgtc gccgacgtgg ccgcgcgaat ggacgaccgg cgcgacgccc   4920
cccggatccc ggaactgcgc gccgggctcg ctccccgcga cggccgggcg gtggaggcgt   4980
ccttcgggca gagcggcatc tggctgatcg accagtacct gcccaacccg gccgcctaca   5040
acggccccct cttcgtccgg ctgccgttct cagccgatcc cgaccgcctg cacgcggccg   5100
tgcgcggagt gctgcgccgc caggaggtcc tgcgcaccac ctacgccctg agcgacggca   5160
cgctccggca gaacgtctcg cgggacgatg acgcggtcgt cttcgaggta gcccgctacg   5220
gcgacgacaa ggaactcgac gccctcgtcc accgggtggc caatctccgc ctcgacctgg   5280
cccgcgggcc ggtcatcgcc gtgacctgcg cgctcggccc cgcgaaccgg tccgccgtca   5340
tctgcaacat ccaccacatc gcctccgacg ccgcctccgc cggtgtcttc ctgcgggaac   5400
tcctcgacgc ctacgaccgc ctcggccgcg gtctgcccgt cgaggccgac ccgctgcggc   5460
ccacctacgg ggacttcagc cagtggtacc gggaactgat gaaccccgag gccctcaccc   5520
gctccctcga ccacttcgcc gcccggctcg ccggggaact cccggtgctc gacctgccca   5580
ccgaccggcc ccgcccgccg gtgaagcaac accggggcgg caccctcccg ttgcacctgc   5640
cggccgccgc ggccgacgac ttcgaggcgc tcgcccggac cgagggggtg accctgttca   5700
tggccctcgt cgccgcgtac gcggtcttcc tctcccgcca caccggtcag cggcgcgtgc   5760
tgatcggcag cccgtctcg ctccgcgacg acccggccac ccacgaactg atcggctact   5820
tcgtcaacct ggtcgtcctt cagcaggaga tcgacgaccg gatgaccgtc cgggacgtgc   5880
tccgccgggc gcgggaggag gtgagcgagg cgctgcggca caagtgggcg cccttcgaca   5940
aggttgtcga gcgtctgcag ccaccgcgca gcagcggcta caccccgctc gtgcagacca   6000
tgctcgtgct cacccagggc gacgccgac ggatatccca cgacgacacg gaactgcgca   6060
tcgagcgcgg ggccgcgcac ggcgccaagt acgacctgtc cctcgttttc gagcgggact   6120
ccgaaggcct gcacggtctg atcgagtacg acgcggacct cttcgacgag ccgacggtac   6180
gggccatggg cgaccggctg cggcacctga tggagcagtt cgcccgacgt cccgacgcac   6240
ccctgcacga actggaggcg ctcggtgcgc aggagcggcg gtcggtgctg gtccgcgggg   6300
```

```
accggaccgc gcacgccgtg cacgacgcac ccgtcatgga actgttcgag gcccaggccc   6360
gggcgacccc cgacgcggtg gcgctggagg acggcgacac caccctgtcc taccgcgaac   6420
tcgacgagcg cgccaaccgg ctcgcccacg tgctgcgcgc ctccggcgct gcggccggca   6480
cccgggtcgg gatctgcctg ccccgctccc acgacatggt cgtcgccctg ttcgccatcc   6540
tgaagaccgg ggcggcgtac gtaccgctcg acccgtccta ccccaggcag cggatcaccc   6600
acacgctgcg cgacgccggg gtcttcctga ccgtgacgga cagctcactg gccgacgaac   6660
tcccccgag ggagccgctg ttcgtgctgg accggcacga cggaccgatc gccgcggccc   6720
ccgccaccgg cctcggccgg gtgaagacac ccgacgacga gatctacgtc gtgcacacct   6780
cgggctccac cggcctgccc aaggggtgg tcatcgccga ccggaccgtc gccaacctcg   6840
tccgggccca gcaccgttgc tcgccggccg gagcgaccgg gcggacgctc cagtacatgt   6900
cgctgtcgtt cgacgtgtcc gtgatggaga tcctcggcac cctgtgcgtc ggcggcaccc   6960
tcgtgctggt ctccgaggaa ctgcgcaagg atctgcacgc gctcgccgga ttcctcgccg   7020
aacgccgcgt cacccgggtg tacctgccct acatcgcgct ccagcagctg gcctccctgg   7080
ccaccgacgc cggtgtgcgc ctggacgacc tgcgcgagat cacctccgtc ggcgaggccc   7140
tcgtggtctc cccgcagatc cgggagttcg ccacccgtca cccggcggtc cggctggtga   7200
acatgtacgg gccgtcggaa acgcacctgg ccagctggta cccgctcacc ggctcgcccg   7260
cgacctggcc cgacaggccg ccgatcggcc gccggtgga cggcgtgcgg ctggtggtcc   7320
tggacgccca catgcggctc gtcccccggg tgtccccgg cgagctgtac atcggagggc   7380
ccgtgctgtc ccccggatac cgcaaccgtc cggacgagac ggcccgccgg ttcctcccgg   7440
accccttcgg cggccccgcc gaccggctct accgcaccgg cgacctggtg cgctggaaca   7500
gcgagggcga cctggagtac ctgggccgga ccgacgacca gatcaagatc cgtggctatc   7560
ggatcgagcc cgccgagatc gaggccgcac tcgacgacct ggacggcgtc gcctcctccg   7620
cggtcgccgc cgtggacgtc gccccccgcg accgcagact cgtggccgtc ctggagacct   7680
cccgcacctg ggagaccgcg gagctgcgcc gcgccctgtc cggcacgctg cccgactaca   7740
tggtgcccgc gctggtggtc gcggtggagc acatgccgac gaccccgagc gggaagatcg   7800
accgccgggc cgtcgccggc ctggccgcgg cacaggcgac cgcggcacgg accgcgcccg   7860
cgccaccccgg ccggccgccc aggccgggcc tggagcagcg gatcgcgcgg gagtgggcgg   7920
atgtgctgaa ggtgcccgcg gtgggcaggg acgaggactt cttctccgtc ggagggaact   7980
cgatcatcgc cacggaactg gtctatcggc tgcgccgggc gttcgaccag gacctctcgc   8040
tgcgcgccct gctggagaat ccgacggtcg cgggcatggc cgcccggctg cgttccggcc   8100
ccggcgctcc caccaccgcc cccgccgcgc tgcgggagga cgcgacgctt cccgacgacc   8160
tgcccgccgt caccggcacc ccggtaccgg tcgcccgggc ccgtgaggtc ctgctcaccg   8220
gcgcgaccgg gttcctcggc agctacctgc tgcgggagct gaccggaacc accgcggcc   8280
gggtgcactg tctggtgcgg gcggcggacg aacgggccgg catggagcgg ctgcgggcca   8340
ccgccgagcg ctaccggctg gacgggcgga tcgactggaa ccgggtgcgc gccgtgcccg   8400
gcgacctgag ccgccccggg ttcggtctgc cggtgcggta gtacgacgcg ctggccggca   8460
ccgtcgacgt cgtctaccac gcggccgcgc acatcaactt cgtgctgccg tacgcctcgg   8520
tgaaaccgac gaacgtggac ggcttccgcc acgtggtccg tttcgccgcg acggaccgcc   8580
ccaagcacgt gcagtacatg tccaccatcg ccgtgttccc tccgggcgag gcgcccgacg   8640
```

-continued

```
gcacggtcct caccgaggac gacgtgcccg aggcgtgcga acgactgggc atcggctaca    8700
cccagagcaa gtgggtcgcc gagcgcatcg cactcgcggc ccgcgcgcac ggcgtgccgg    8760
tcaccatcca ccgcatcggg cgcatctcgg gcgacagcgt cacaggcgcc tgccagagcg    8820
acgacttcct gtggcggcag atcaagagct tcatcgaact cggctcggcc ccgccggccg    8880
aggacctcac caccgatctg ctgcccgtcg atttcgtcgc ccgcgccgtc gtcgccctct    8940
cccgccaccc cgccacccac aaccgcaccc tgcacgtctt ccacccgagc ggatcggact    9000
tcaccccggt ccacgcggcc ctgcgcgcgg acggccaccg cctggagatc gtcccggccg    9060
acacctggct tgcccggctg gaggagtccg cacggcggcc cggcggcaac gccctggcgg    9120
cagccgtgcc cctcttccgc gagggcgccc tggaactggg cgacaacacc tacggcaaca    9180
ccgccaccac ccgcctgctg atggacctcg gactgccctg gccgccatc gacgagcagg    9240 cgatcacgcg gatgctccgc tacttccgct ccgtcggaga actggccgac gactgagggg    9300
acttccctgt cccgggccct cccggcagcg cggcgcagcc gccggcgccg atccgaccat    9360
ccaccacacg gcaatcgccg aagcggtcgc cggacaccga aagcaccagc agccatgcca    9420
acgagctcct gccccgacac cgcatacgac accctcatac cctccgtcgt cgcggctctc    9480
ccggccgcac agcagccgga gtggccggac cccgggcgac tcgccctcgt ccacaccgaa    9540
ctggcccgcg cggacccgct ggtgacgtac gacagcgtgc gtgccctgcg ccggctgctg    9600
tcccgtgccg ccgaaggcga actgtgcgtc ctccaggccg cgactgcgc ggaggacccc    9660 gccgagtgcg gcccggcccc gctggcccgc aaggccgaga tgctggacgt cctcagcgac    9720
atcgtgcgaa cggcgccgg acggccgtc gtccgggtgg ccgtgtcgc cgggcagtac    9780 gccaaacccc gctcccaccc ggaggagctg cacgacggcg tccggctgcc ggtctaccgc    9840
ggtcccatgg tgaacgcccc ccaccccgac gccgacgcgc gccggccga tcccgcccg    9900 atcctgagct gctaccgggc cgcccgccgg gccgtggagt ccctggaccg gctgggccgc    9960
ggcgagggtt cgcccgccga gacccgggtg tggaccagcc acgaggcact gctgctcgac   10020
tacgagctgc ccctcgtgcg ccggcaccgc tcgggccgca gttacctcgc cagcacccac   10080
tggccgtggg tcggcgaacg gacccggcaa ccggacggtg cccacgtacg gctgctggcg   10140
gaagtggaca acccggtggc gtgcaaggtc ggcccgacca cgaccgtgga gcaggtgctc   10200
gccctgtgca ccgcgctgga cccggagcgc tcaccgggcc ggctgtcgct ggtcgcccgg   10260
ttcggcgcct cccgcatcga cggcctggcc cccctggtcc gcgcggtacg gcgggccggt   10320
cacccggtgc tgtggctgtg cgacccgatg cacggcaacg gtgaacgcac cgcgcacgga   10380
ctgaagacgc gccggctcag cgccgtgatg gcggagatca gccggttcgt ggacatcgtc   10440
tccgccgagg gcggccgcag cgccggcctg cacctggagg cctcaccgga cgacatcgcc   10500
gagtgcaccg gcgccggatt cacccggcc cccgggccgg cctaccgcac cctgtgcgat   10560
ccccgcctga acctggtgca agccgtcgcg gcgaccgcct actggcggct gccggccctg   10620
gaggccgtcg catgagcgag tctgcgcgga acgcgcgcgg cctggcggcc ctgctgcccc   10680
cgccgggcac cccttcgcc gtcctgcacc ggccgggtgc cggcaccct ggcaccgtgg   10740 acgtcgtcag cggccccctc cgcaccgccg ccacccgc cgagctgagc ctcgacgacg   10800
agtccgcgcc ggcctccag ggccccggac cggcgcacag ggtcctcgcc ctggtgcccc   10860
accggcagat cgccgaacga ggcttcgcg ctcccgacga cggcacccg ttgctggcca   10920 tggacatcgg cacccagcac accgtgcccc tggagcggat gctggcactc ctgcccgacc   10980
gcgaactgca cgtcgaggaa accgggttcg acctcgacga cgaccggtac gcggccggcg   11040
```

```
tcgacgcgct cacccgccag gagatccagc gagggcaggg cgcgaacttc gtcctcgccc   11100
gcagcctgca cggccggatc cgcgacttcg accggacccg ggccctggcc gcgctgcggc   11160
ggctgctgat cgcggagagc ggcgcctact ggacctacct ggtctgcacc ggcgaccggt   11220
acctcatcgg cagttccccc gagcagcacg tacgggtggc cggctcgcgg gtgtcgatga   11280
acccgatcag cggcacctac cgctaccccg aggggggccg cccggaccgc gaaagcctcc   11340
tccggttcct cgccgacccc aaggagatcc acgagctgta catggtcgtg gacgaggaac   11400
tgaagatgat gaccgaactg tgcggttccc gcgtgcgcgt gtcgggcccc acgctcgcgt   11460
ggatgtcgcg tctcgcccac acgcagtacc acctgcacgg cgagtccccg ctgcccctga   11520
ccgacatcct gcgcgggaca ctgcccgcgc ccacggtgac gggcagcccg gtggagaacg   11580
cctgccgggt catcgcccgc cacgaaccgg caggccgggg ctactacagc ggcgtgctgg   11640
cgctggccgg ccaggagggg ggacggcgcg ccctggacgc ggtcatcgtg ctgcgcaccg   11700
ccgacatcac cgcggacgga tccgtgcggc tgaccaccgg cgcgaccgtg gtgcgtgact   11760
cggtgccccg cgaggaggcg gcggagacca cggcgaaggc cgcggggctc ctcaccgcgc   11820
tgacccgcgg cccggccggc cggtccgcgg cccggcgca cgcggcaccc gacgtctccc   11880
tgggagccga tccggcggtg cgcgcggcgc tgcgctcccg caacgacggc atcgccgcct   11940
tctggctcgg cggcggggcg cgcctgccgg cgccctcgcc acacggacca cgggtggcgg   12000
tgatcgacgc ggaggaccgg ttcaccagca tgctcgcgca gcagctccgc gcggtgggct   12060
gccacgtcac cctgcacccc tggtggtcgg ttccggaggc agccgacgac cccggcaccg   12120
tgctgctgct ggggccggga cccggggacc cccgggacgt cggcgacccg cgggtggcgc   12180
ggctgcgctc cctggccggc cgccggctcg cccggcggtt gccgctggcc gcggtgtgcc   12240
tcggtcacca ggccgtctgc ggggtgctgg gccttcccct ggtccggctc gcgcggcccc   12300
gccagggcgc ccggatgcgg gtcggcctgt ggggacgcga ccggcacgtc ggcttctaca   12360
acagcttcac cgcgcgctcc gacaccgatc gctgtccgct gccggccgg dacgccacgg   12420 cccgggtgtg gcgccgggac gggggagacg tggtcgcgct ggacggcccg ggctggcca   12480 ccgtccagtt ccacgccgag tcgctgctca ccgaggacgg cccggacatc ctgcgcgagc   12540
tggtggaccg gcggccgt accgagcggc gcaccgaggc cctgatgtcc cgccgagcca   12600
aggagcacgc gtgaacccgc ccggaaccgt cgtcgccaac gccgcctgg accccgggga   12660 gctgcgccgg accatggggc acttcgcgac cggcgtcacc gtgctgacct gccggcgcgg   12720
cgcccggctc acggggcgga cggtgaactc cttcacctcg gtgtcgctcg atccgccgct   12780
cgccctggtc gccctggacc gtcgcacccg cgccgccgcc ctcctggacg acggcccctt   12840
cgtcgtcaat ctgctcggcg agcaccagca ggacctggcc ctgcactttg ccggcggctc   12900
gccggccgat tccgtgccgt gggtggacgg cgacggcgac cggccccggc tgcgggaac   12960 cctcgggcac ctggtgtgcc gaccctggcg cacctacgac ggaggcgacc acacgctgca   13020
tgtcggccgt gtcgaggagt cgccgccgg aggggacgg ccgctgctct tctaccgagg   13080
cgtcttcccc cgcctcatgc cggacggagg aggagacccg gagggacccg aggaggtgtg   13140
gtcgctctgt ctgacggcc caggaccggc cacggatcag ttcgtcaccg atcatgagac   13200
acggaagtag ggacatggca cccgacaacg gacagtccgc agcacccggc acctccgggg   13260
cgtccaccgg caaggcccgg gtcacccggc cgctgaccgg ggacgagtac atcgagagca   13320
tccgcgacgg acgggagatc tgggcgtacg gcgagaaggt cgacgacgtc accaagcacc   13380
```

```
cggcgttccg caacaccgtg cggatgacgg cccgcttgta cgacgccctg cacgatcccg    13440
agcaccacga caccctgacc gcgcccaccg acaccggcag cgacggcttc acccacaagt    13500
tctaccgggt gccgcgcagc gtgcaggacc tcgtggggga cagggacgcc atcgccgact    13560
gggccaggct gacctacggc tggatgggac gcagccccga ctacaaggcc agcttcctgg    13620
tgaccctcgg cgcgaacccc gactactacg gcgacttcgc ggacaacgcc cgccggtggt    13680
acgccaccgc ccaggagaac gtgctgttct ggaaccacgc ggtgatcaac cctccggtcg    13740
accggcaccg gcccgccgac gaggtggacg acgtcttcgt gcacgtggag aaggagtgcg    13800
acgacgggct ggtggtgagc ggggcgaagg tggtggcgac cgggtccgcg ctcacccact    13860
tcaacttcgt ggcgcactac ggactgcccg tgaagaagaa ggagttcgcc ctcgtcgcca    13920
ccctgcccct ggcggcaccc ggcgtgaagc tcatctgccg ccagtcatac gaactggccg    13980
cgagccgcac gggcagcccg ttcgactacc gctgtcgag ccggctcgac gagaacgaca    14040
```

```
cgagccgcac gggcagcccg ttcgactacc gctgtcgag ccggctcgac gagaacgaca    14040
ccatcttcat cctggacaag gtgaagatcc cctgggagaa cgtcctcatc tacggggaca    14100
ccgccagggc cggcaccttc ctgcagacct ccggcttcac ccaccggctc accttccacg    14160
gggtgacccg gctggccgtg aaactggact tcctggcggg cctgctgctg aagggcgtgg    14220
aggtcaccgg caccaaggac ttccggggca tccagacccg ggtcggcgag gtcctcgcct    14280
ggcgcaacat gttctgggca ctgagcgacg cgatggcgca aaccccgat ccgtggcacg    14340 acggagccct gctgcccaac ctcgactacg gcatggccta ccggtggttc atgaccgtcg    14400
gctacccgag ggtccgggag atcatcatgc aggacctcag cagcgggctg atctacctca    14460
cgtcgcacgc caaggacttc aacgaacctg aactccgtcc ccatctcgac cgcttcatgc    14520
ggggttccaa cggttacgag gcggtggagc gcgccaagct gatgaagctc atctgggact    14580
cggtgggcac cgagttcgcg ggccggcacg agctgtacga gcggaactac tccggcaacc    14640
acgagagcgt gcggatcgaa ctgctgcacg cccagacggc ttccggtctc gtcgaccagt    14700
accgggcttt cgccgaacag tgcatggcgg aatacgacct ggacggctgg acggcaccgg    14760
acctggtgcc gcccgacgtc gactgagcgc cgcggccatc cggccggacg ggcccgccgg    14820
gcggtacggg aggggcggga ggagcccccc ccgcccctgc cgctcagccg gtgaccaggg    14880
cgagcgtgaa accgtcgtac cccttggtgc cgacggtctg gatcgaggtg cggtgacgt    14940 ccgagcggcc ggccagcatc tcgtggaacc ggcgcacgcc ctggacgccg cgtcgggat    15000 ggtccgggtc ggtcaccgcg ccgcccagga cgacgttgtc gacgaccacc accgcgcccg    15060
gccgggacag tttcagcgcc caggtgaagt actcggggat gtcgggcttg ttggcgtcga    15120
cgaacaccat gtcgaagggg gcggtaccgg gccggtcgag ggtcggcagg atgtccagcg    15180 cccgccgac gtgctgttcg acgaggtggg cgacccccgc ctcggcgagg cgcgacgcgg    15240
ccgactcggc gaaggaccgc tcccactcga tggtgacgag gcggccgtcc ggcggcagcg    15300
cgcgggccag ccagatgctg ctgtaccgcg cgaacgtgcc gatctccagg atgcgccgcg    15360
cctgccgcag acgcgccagc agatgaagga gtttgccctg gggggcgctg acggcgaggt    15420
ccggcaggtc gaattcccta tgggcctgag cggccttcga aagtgcttcg tcctccttca    15480
cgagaaggga gctgaagtag acgtcgacac tgttccatcg ctcttgttcc atggttgcaa    15540
taattcacga taaaccctcg gatggcaaga gcagaattcg atatccatgg tgccgtgaac    15600
ctgagaatgc ccaggtcagc ggcctattca aggctgtcca gtcaccttcg ccaaagaaat    15660
taacgggcgg tcgataatgt tcggaaattc cttcggtgcg gcgttgactg tcgtccttgc    15720
ggtcacctag cctcccttc tggaaccttg tgaaaaagcc tgtcccggat aggagtgtca    15780
```

```
tttcatgcga gaagactcgg ccgtcacaac ggccgcaccc ccggtgcacc tggtgccggc    15840
gatgcaccac ctgggcgtcc aaacccgcga cctggacaac tccctggcgt ggtacaagga    15900
cttcttcggc tgcgccgaga cctggacgct caccacgttc tcggacctga cccgcagcag    15960 gctcccggc atcacccggc tcaccgagat cagcgtcgcc gacgtccgct ccacctctt    16020 cgaacgcgcc gggcacgacc cggccctgcc cggcggcaac aaggcccagt tccagcacgt    16080
ctgcctcgcc accggttccc cggaggaact gcgcgcctgg cgcgatcgct ggatcgagct    16140
ctaccgctcg ggccgctacg acttcgcgac cgatgagcag cccacggaca tcgtggtcga    16200
cgccgacgga gtgcacagct gctacctgtt cgacccaaac ggcctcgagt tcgagttcac    16260
ctacgttccg ggcggtgcgg catgagcgcg ggcccgcacc ggaccgtcac cgaactgccg    16320
gtcgccgaag gctgggactt cggggacttc ccctacggcc tggagccgct gaccctgccc    16380 gagccccgc acgagcccgc ggccgacgtt ccggacgtgc tgtgcgccga gcccgccccc    16440
ggcggtgcgc ggacgtcctg cccgcgcacc ggaccggcgc ccggcctccc ggagctggcc    16500
caccagctct tctggttccg ctggatcacc ggacaccagc tgaccttcgc catctggcag    16560
ttactcggcc acgcgctgca ccaggcgcac gcccggcccg accccggccc gtcgctgcga    16620
gccatgacgg acctgacacg gcgtacacc gcgatgctgc tctacaccgg ctcctgtccc    16680
aaggacgtct acagcgacgt gatccggccc agcatgttcc tgcagcaccg cggcttcagc    16740
gggacctggg cgccggactt cgtccccgtc cgccggctgc tgcggggcag gaagacgccg    16800
tggcacgaga ccccggaggg cggccggctg gccgacgagg tccgtctcta ccacctggtg    16860
cactcggggg tcgccgcgaa actcgtaccc ggcggcaggt ccctgctcca ggacaccgcc    16920
cccacggccc ggccgcacga cccccggatg caggcgctgg tctacgacaa ctacttcctc    16980
accctgcgcg ccgacgtccc gaccgccgag gtcgtcgagc agctccggcg ccgactggcc    17040
gcggtgcgcc tggacgtctc ggtcaacggg ctgtaccccg ggctgaccgc gcaggaggac    17100
gccgcactgc ccgaggagtt gcgcagcgag gacacacagg cctgcgagcg ggacttcgac    17160
gccgtcctgc ggcgcgtcga cggccttgcc gccgcactcg accggcggtt gctcgacggc    17220
acgatcgccc gctgagcctg agccacccga tcacgcgaca ggaaaggagc ggtggaccgt    17280
gcggtacgga gtcgtcgtcc tgcccgaacg ccggtgggcg caggcccgcg aacagtgggt    17340
ccgtgccgag gagttcggat tcgaccacgc ctggacctat gaccagctga tgtggcgttg    17400
gctgcgcgac gagccctggt tcggcgccgt gcccacccty gcggcggcgg ccgaggccac    17460
ctcgaccctg accgtgggca ccatggtggc cacacccacc tatcggcacc cggtgacgct    17520
ggccaaggag gtgatgaccc tcgaggacat cgcgggcggc cggttcgtct gcgggctggg    17580
agccggggcc ggcggcctcg acgaccgcgt cgtcgatccg gccgcctact ccccacggca    17640
acgcgccgac cgcttcacgg agttcgtcga cctgctcgac aagctgctga ccgccgcag    17700 caccacacac accggcacct actacgacgt ccggagggtg cccgtgcacc cgggctgcct    17760
ggccacgccc cgggtgccgt tcgccatcgc ggcgaccggg ccgcgcggca tgcggctggc    17820
ggcccgccac gccgacatgt ggatcaccgc ggggcggccc ggcgacttcg acgcccttcc    17880
gtacgaggag accctgccgg tgatcaagga gcagctggcg cgcctcgacg aggcgtgcga    17940
gcggaccggg cgggatcccg ccacccctgcg ccggctgctg ctgaccggcg ccatggtggg    18000
cggcaccctg gactccgtcg aggcgtaccg cgacgccgcc ggccgcttcg gcgaactcgg    18060
catcaccgac ttcgtcgtcc actggccccg gccctccttc cctaccagg gcagggtgga    18120
```

```
agtgctggag cagatcgcgc gggacgtgct gaccgtccgg ggcggggagc ggccgtgatc    18180
gcctacgaga tcgtcgacat gttcaccggc acgcccttcc agggctgcgc gctcggggtg    18240
gtcccggacg cgaccgcact cgacgacgac ggcatgcggg cggtggcccg cgagatcggc    18300
ctcaccgaga cggcgttcgt cctgccaccc gagtcgcccg acgccaccca ccgggtacgg    18360
gtcttcaccc cggagcggga gtcaccgtac ggcgggcact ccgccatcgg cacggccacc    18420
accctggtgc ggctgggccg tctgcgcgcg ggggagctgg tgcaggagtg cgggggccgc    18480
ctgatgaccg tgcgcgccag tgcccgacgg gccacgctcg gcgtccgggg ggagcccgtg    18540
ccacccggcg cctgggatcc cgtgccgttg ctggaggcgt gcggcctcac cgaggacgac    18600
ctggtcgccg ggccccgcgt gaccgggttc ggaccggcct tccacgtgct gccggtcgga    18660
cccgaggcgg tcgcccgtgc cgcacacgac ccggcgcacc ccgtgtggtc cacctgcccg    18720
gacgcggtgg tggtcgccta cgacaggcgc ggacacctgg ccgacgtcag ggtcttcgcc    18780
cccggctacg gcatgccgga ggacccggcg tgcgcctccg ccgccctggc actgggcgcc    18840
tggctcaccg gcgcgggcct ggtgccggcg acggacggta cccgccttta ccgggtccgg    18900
caggggcacg ggctgggccg cccccgcccg ctcgactgcg ccgtgaccgt acgcgacggc    18960
cgagcggtcg cagccgaggt gaccggggag gtggcggcca ccgccgccgg ccggatgcac    19020
ctgccccgca cggcggccgt cgcgcgctga gccggggccc gggccgtgta ccaggccgag    19080
ccgcggaagg caccccggtcc ggtcgacgca cacccagagc acacgacgcg aatccctgta    19140
tcgcagaacg aagaggagag gaacccgact gtgttgttcc gtccagagct gcgcggcacc    19200
cggggcgcgg tcgcctcgac ccactggctg gcctcggccg cgggcttccg catgtacgac    19260
aagggcggca acgcgttcga cgcggccgtc gccgccgcgt tcgtcatcca ggtcgtggag    19320
ccccacctca acgggcccgg gggagacgtg cccgtcctcg tccaccgggc cgggagcggc    19380
cgggtcgacg tcgtctgcgg ccagggcccc atgccccggg ccgcgaccat cgagaggttc    19440
gaacagctcg gcctgtccgt ggtccccggc tccggcctgc tgcccgcggt ggtgcccggc    19500
gccttcggcg cgtggctgcg ggtcctcgcc gagtacggca ccctgcgtct ggaggacgtc    19560
ctggagccgc cgatcggcta cgccgaacgc ggctatccgc tgcttcccaa ggcggcggcg    19620
atgatcgagg cgctccagga actcttccgc gacgagtgga ccgagtccgc ccgcacgtac    19680
ctggtgggcg gggccgcgcc gcggcccggt cagcgcatga ccaaccccga cctgcccgg    19740 acctaccggc gcgtcctcga cgaggccagg gcggcgggcg ccgatcgcga caagcagatc    19800
gacgcggccc tgcgcgcctt ctacgagggc ttcgtggccg aggccatcga cggctatctc    19860
gccaaggcgg aggagatcga tgccaccggc cgccgccacc gcggcctgct gaccggcgcc    19920
gacctggcag gctggcgggc gacggtggag ccctcgctct ccttcgacca ccgcggcctc    19980
accgtgcaca aggcgggacc ctggtcccag ggcccggtct tcctgcaaca gctcgcgctg    20040
ctgcgggagt tcgacctcgc cggtatggga ccgcacagcg cggagttcgt gcacaccgtc    20100
accgaggcgg cgaaactggc gttcgcggac cgcgaggcct ggtacggcga tcccgcgcac    20160
gcggaggtgc cggtcggcga cctgctggac ccggcctaca ccgcggcccg ccgcgagctg    20220
atcggcagca aggcgtccac ggagctgcgg ccgggctcac cggaggccg acaccggtg    20280 ctgccgcccg tccacgacga gtccgccggt ccggccggtc cctcctggct cggcgagctc    20340
gaggagggca tccggcggt ggtgcgctcc acggccgccc ggggcgacac ctgctgcgtc    20400
accgccaccg acgcccacgg gaacatggtg gtcgcgacgc cgagcggcgg ctggctgaag    20460
agttcgccgg tggtgcccgg tctgggcttc ccgctcggta cccgtgggca gatggccacg    20520
```

```
ctcacccggg ggcacgccaa cgcgctggct cccggcaagc gcccccgcac caccctcagc    20580
ccgaccctgg tgctccggga gggcaggccc gccctggcgt tcggcacacc gggcggcgac    20640
cagcaggacc agtggacgct gcagttcttc ctgaggcaca ccgaacacgg catgggctt     20700 caggaggccg tcgaggcacg gaccttccac accgaccacg tcccgacgtc cttcaccccc    20760
cggcgtttcg ctcccgggac ggtgaccgtc gaaagcggca tgccggagga accatccag    20820 gagctcaggc ggcgcggcca ccaggtccgc acggtcgccg actacagcct gagcaaggtg    20880
tgtgtcaccg gcctggccag cgacgacatg gtcatcgcgg cggccagtcc gcgcggcgcg    20940
caggcgtacg ccgtcgcgga ttgaggatgc cgaccggatg cgataagttt ccaaacggaa    21000
atcgtctcgg cgaatggaag gggaacgcat ggtgccccac ccgtcactgg acccgggtga    21060
ccacatcgtt ctgggagaag cacggcagaa caacctcaag ggcgtcagcc tgcgcatccc    21120
caagggacgg ttgaccgtct tcaccggcgt ttcgggatcc ggcaagtcct ccctggtctt    21180
cgggacgatc gccgtcgagt cgcagcggca gatgaacgag acctaccccg cgttcatccg    21240
caaccgcctc cccaagttcg agcggcccga cgcggaggtc atcgagaacc tctccaccgc    21300
catcgtgatc gaccagcgcc cggtcggcgg caacgcgcgc tccacggtcg gcaccatgac    21360
cgagatccac gccatgctgc gggtgctgtt ctcccggcac ggcaggccca gcgcgggtcc    21420
ctcacacatg tactccttca cgatccgcg cggcatgtgc ccggagtgcg agggactcgg    21480
atccagggtg cggctggatt tgaaccgcct tctggacgag gacaagagcc tcaacgaggg    21540
cgccatccgc ttccagccct tcgcggtggg caccttcccg tggcagctgt acgcggagtc    21600
cgggctgttc gatcccgacc tgccgctgcg ggagttctcc gcggacgacc gcgaactgct    21660
gctgcacggt tccgggttca aggtcgaccg ggccggccgg cacggcgtct acaagaacga    21720
gtacgagggc atcgtgctgc gcttcacccg gcgctacctc aaggcgggcc tcgacaccct    21780
caagccgaag gaacgggcgg cggtgcagga ggtcgtgacg gaggggccct gcgaggcctg    21840
cggaggcgcc cggctgggac cggccgcgct cgcgtcgcgg atcgccgggg agaacatcgc    21900
cgactactcc gccctggagg tcaccgatct gatcggccgc ctggagcgca acgacgcccc    21960
accggtcaag ccggtggtcc aggcggcgct ggccgcactg cgcaggatcg aggccgtcgg    22020
actcggctac ctcagcctcg accgccagac cgccacgctc tccggcggcg aggcgcagcg    22080
gctgaagacg gtacgccacc tgggcagcag cctgaccggg ctgacgtaca tcttcgacga    22140
gccgagcgtg ggcctgcacc cgcgtgacgt gcgccgtctg aacgagctgt tgctcgccct    22200
gcgcgacaag ggcaacaccg tgctcgtggt ggagcacgac cgggacgtga tcgccatcgc    22260
cgaccacgtc gtcgacatgg gcccgggcgc gggcagccag gcggcgagg tggtctacga    22320 gggatcgccg accgggttac ggggctcgga cagcccgacc ggacgcggcc tgcgttcggt    22380
gccgggactg aagcgccgac tgcgcgcccc cgacggcagg ctgacggtcc gcggcgcgcg    22440
gctgcacaac ctcaaggacg tcacggtcga cgtgcccacc ggtgtgctgg tggcgctgag    22500
cggtgtcgcc ggctcgggca agagctccct cgcccgggag ctggcagcgc ggcacccgga    22560
ggaaacggtc gtggtcgacc agtcctccat cgggatctcc tcccgatcca ccccgcgac    22620 gtacaccgac atcatggaca ccgtccgccg gctgttcgcc cgcgcatccg gaaccgaccc    22680
cggcctgttc agcttcaact ccgcgggcgc ctgcccggag tgccagggcc gcggtgtgat    22740
cgagaccgac ctcgcgttca tggacccggt caccaccgtc tgcgagcgct gcgaggggcg    22800
ccgcttcaac gacgaggcgc tgagccacac cctgtccggc cggaacatcg ccgacgtcct    22860
```

```
cgccatgacg gccgaggagg cgatcgggtt cttcgcggag gactccgtcc gccgcaaact   22920
ggccctgctg acggaggtcg gcctcggcta cctgacgctt ggccgctccc tgtccaccct   22980
gtccggcggc gaacgccaac ggctgaagct ggcgcaccgg ctgcacgcct ccggcagcgt   23040
ctacatcttc gacgaaccgt ccaccggcct gcacatgacg gacgtgggca agctgctcac   23100
cctgttcgac cgcctcgtcg acggcggcaa cacggtggtg gtcatcgaac acgacctcga   23160
cgtgctcaag tacgcggact ggatcatcga tctcggcccg gaggccggcc ggcacggcgg   23220
ccgggtggtc ttcgagggca ccccggcgga cctggcgcgg gtgcgggaat cgcacaccgg   23280
ccggtgtctg gccgaggacc tcgccgcaca cggtcacctc tgacggcccg gagcaccggc   23340
tcgccgccgg gtccgggccg gggtcgcacc ccgtcctccc gcacacctcc cgtccgacaa   23400
ggagtccgta tgcccctcat ccacgtcacc ctgctgagcg gtcgcggcga ggaggagatc   23460
gccgccctcg gccgggccgt cacggaggcc gtacacacca cgctgggcac cccccgggag   23520
gcgatccggg tgacggtgga cgcatgcccg cccgagcact ggttcgtggg cggcgtctcg   23580
atggcggaga agaaggcggc ccggggcggc tgagcggtgc tccgttcgcc ccgggcgccg   23640
cggttcaggc cgcgtccgcg aaccgccggc ggatccgccc gacgtgctcc gggtccacgg   23700
ccgggaggtc gtcgcgggtg agccggccgc tgcgcgtcag caggtgcgcg ttgaaggcct   23760
ccggcgccag ccccacgcag cggtcgatgt tctcgaacca ctccaggctg gtcagcgcgg   23820
tccgctgcat ccgctccacg gcgggccgcc gctcggcctc gtaggccgcc agagcctcgg   23880
ggaccgtccc gtggtcgtgc agggccgtgg cgagggacag accgtcctcc atcgccagtt   23940
tggtacccga accgatcgag aagtgcgtcg tgtgggcgct gtcaccgagg agaacgaggt   24000
tgccgtggct ccagtcgcgg ttgcgtacgg cagcgaagcg accccagtac gaccggttgc   24060
cccacagccc gtgtccgtcc agcagaccgg tgaagtactc cctcaccctc ccgatgctct   24120
cccggtcgcc caccgggtca tcggaccggc gctccgcggc gcggaaaccg gccgcccgcc   24180
acaccgcgtc accgatctcc acgatgaacg tgctgcgacc gggggcgtac gggtaggcgt   24240
gggcctgcac cgggccgtgg tcggtctcga ccacggcgaa ggtgagcgcg tcgaacggcc   24300
ggtccgtgcc gagccacatg taacgcgacc cggcctgttc ccgctccgtg ccgaacgcgg   24360
cctcgtaccg cgcgcgggtg cgcgatccca cgccgtccgc ggcgacgacg aggtcgtggg   24420
acgcgcgcaa ccgggacacc tcgggcgccg gggagccgaa gtgcagacgc accccgaggt   24480
cggcgcagcg ctcctgaagg agccgcagca gggtgtggcg gccgatcgcg gcgaacccgt   24540 accctcgtt gcgctggacc cggccccggt agcagacgtc gatccgcgtc accgggcga    24600 actcggcctc gacagcctcg aacagagccg ggtcggcggc ctcgatgccg ccgagggcgc   24660
cgtcggagaa gacgacgccg aacccgaacg tgtcgtgggc cgcgttggcc tcccacacct   24720
ccacgacgtc gtggggccgc aggcgcttga ccaggcaggc cgtgtacagc ccgccgggac   24780
cggctccgat caccgctatc cgcatgacac ctcgctgggg ctccgagaga gatggatgga   24840
cgtgcagaga ccagtaaatg ctatccgaag agaaatgatc tggtggtcaa tctcctttcc   24900
agctccgcga gttccgggac tgaccggagc agatcgttgc ccacacgtaa tcaagtctga   24960
cggaaggatg cccacatgcc ggacgtcctc accccacccc cgctgccggc ggccgacctg   25020
gcgggcctct tccgcgccct ggaccgccg ccgttcgccc tggtgcgtcg tgccgcaccg    25080
gacgggacca gcaccggccc gttcgacgtg ttcatcggca ccatggacac cgtgcgacgg   25140
gtgacggacc tgccgtcggg cccggccgtg ccggcgggg gaccccacac actgccccta    25200
ctgccgtacc ggtgcctggc cgaaagaggg ctggactgcc acgacgacgg cacaccactg   25260
```

```
agggtcctgc ggatccgccg gcggcacacg gccgaccacg ccgcgctcac cgcggccctc    25320
gccgcggtgc ggcccgcggg agacctcctc ggggaaggcg ccggcttcga cggctccgac    25380
gaggactacg ccgacctggt ccgcgacctc atggccgacg aggtggcacg caccggtctg    25440
cacgtcctga tccgcaggga cttcaccgcc cggttgccag acacggacc cgtggtggtg     25500 ggcgaactgt tccgccggct gctggccgtg gagcacggcg cgtactggac gttcgcggtg    25560
tacaccggag gccccgacgg tgccgcactg gccggagcct caccgcaggg tcacgtcaca    25620
ctgcggaacg gccgggtcgt gatgcgcccg atgtgcggca cgctccgcct tccacccggt    25680
ggccggccga gcgccgccga cctggtggcc ttcctgcgtg acggcaagga gtccgaagaa    25740
ctgggggccg tggtcgacgc ggaactcgcc atgctgtgcc ggatcagcga ggggacgta    25800 cgcctggaag gaccgcgcct gcgaccgatg gcccgcgtac tgcacaccga gtgccgcatc    25860
agcgccaccg ccgcgctgcc ggcccggcac acgctcgccg gctccctgtt cgcggcgacc    25920
gccgtgggcc gcccttcgc ggacgcgtgc gcgtcatca cccgccgcga accaaccggg      25980
cgcggttact acggcggcct gatcgcgctg ctgggccacg acgacgcggg aaacgaggaa    26040
ctggacaccg ccgtgctcat ccgcaccttc gaggtgtccg gcagggccg gctgaagctg     26100 tcggtcggag ccaccctcgg gccccgctcc gtggccgccg acgagacggc cgagacgcgc    26160
gccaaggcct cggccctggt gtcggcgctc gcaagcggag gaccgactgc ggagggcggt    26220
gccgggcgcc acgcgcgggc tggtcttggt cgcggcccgg aggcggccgg cggcccggcc    26280
accggtgagc gaagcggagt gccgggtgac cggacgcggc accagcaggc cgccggccgg    26340
cagcccacgt ccccgccga cccggcgtgg cgcccgtcgg tgaccgcgga gggcggtgcc     26400
ggggaccacg cgcgggctgg tcttggtcgc ggcccggagg cggccggcgg cccgccacc     26460 ggtgagggag gcggagtgcc gggtgaccgg acgcggcacc agcaggccgc cggccggcag    26520
cccacgtccc ccgccgaccc ggcgtggcgc cgtcggtga ccgcggaggg cggtgccggg     26580
ggccacgcgc gggctggtct tggtcgcggc ccggaggcgg ccggcggccc ggccaccggt    26640
gagggaggcg gagtgccggg tgaccggacg cggcaccagc aggccgccgg ccggcggccc    26700
acgtcctccg ccgaccggc gtggtgcccg tcggtgaccg cggaactgga ccggcgccgc    26760
gcacgtctgt ccgcctactg gcaacgcccc cgtcggccgg gcagccgccc cgctccgcgg    26820
ccaccggtgc tgctcgtcga cacgggtggc gaggagacgg cgccgctggc cgccatgctg    26880
cgcggactgg gccgcaccgt cgacgtgcgt cccgcgtacc ccgcggcggc cgcgccacgg    26940
accgtcgcgc ccggaaccac ggtcgtcctc ggccccggcc cgggtgaccc gttggcccac    27000
ggcgacgacc gcatcaccgc gctgcgggcc atgacgtccg ccctcctgtc cagcggagca    27060
cccacgttcg gggtcgggct cggcttccac ctcctgctcg ccgtgctggg tctggccggg    27120
gccgcgcgag cgtgggacgg ggccaccggc cagcgggaga tcgaggtctt cggcagacgc    27180
gcgacggtgg ggtacggtgg cacgcacacc gtggtggccg gcccgcacac ggacaccctc    27240
gcgcggcggc tgtccctgac gctctgctac ggcccggccc acggcgagct ggtggccatg    27300
cgaggccctc gaaccggcgg cgtcgccttc ctcccggcat cggtgctgag cgtcgagggg    27360
gcggagctgc tggatctcct gctgccctga gcgagcgggt gacgggccgg gccccggccg    27420
ctcacccgtt cgccgtgccc ccgagctcga gcacggtccg cgcggccgac tccagcgcga    27480
gtgtcatcga gccgccgttg ggctcgaacg aggtgtggtc accggcgaag tggatccggc    27540
cctccggccg gcgcatggcc ggcatcaggg aactgtgccc catctcggga aggatgtagg    27600
```
cgccttcgat gtacggctgc tggtcccaga ccaccgaggt gccggtctcg aagtgctcgc    27660
gggcaccggg cagcatcgac tcgacgtgtt ccagggcgaa gcggatccgc tcctcggggc    27720
tcagcacggc aagcgcccgg gcccgccagc cggttatcag gcactccagt atcttgcggg    27780
gcccgggcaa ccggggagtg gcgtcccgga cccaccgcac cggcaggtcc gtggagaaac    27840
tcgcgttgtc ctgggcccag aaccgccggc gcatctggag gtagacgcgc acgatcgacg    27900
agtacttcac ccggcgcatc acggcctgtt tggcgtcgga cagcccggcg tccgtgaagt    27960
cgatgtgccg gatcgcgctg aacggcaccg tcaccaccac gcggtccgcg tccacggagc    28020
gcatgcgggt gccgtccagg aaggtgacac gagcgccctc gtcgtcctgg gcgacccgca    28080
ccaccggagc gcggtagcgg atgcggtcct tcagccgctc ggcgaacgcc cggggggaagc   28140 ggtcggttcc gcccttcacc ttcgaccacc ggggtcggc gttggccagc gagtgcgggc     28200
tggactcgtg ccgcagccag gacagggcgg aggccgtctt gaggtccccg ccgcgcatct    28260
ccaggaagtg cggttccacc aggtcgatcg ccgccggcga agcgcccgc ccggacagca     28320 cctcgtacac cgagcgccgg tcgtacggtt cgagcagggg ggtcggcgcc cagtccgcag    28380
ccgtgatgtc gggttccagc gcctcgtagg cgccggcgcac atagcggtcg atcatgtcgg    28440
tgacgctcag ccccttctcg tgcggggcga gcgggagccc ggcgcggtcc agcgagtcgg    28500
cgtcgggacc gaagaaccgg ttgccgacga agtacgagaa ctggctgccg accaggtcgg    28560
ccgtctccag ttccacccc agttcgcgca ggtagtgcat ggcgtagtgg cagtgcgggg     28620
tcagcgtcat cgcgccggcc tcggcgtaca gaccgtccgt gaacggctcg cgcagtgtgt    28680
acgcacgccc gcccggacgg ttcgacgcct ccaggaccgt cacgtcagtg ccgcgccggg    28740
ccagttcgta ggccacggcg aggcccgaca ggcccgcacc tatgacgacg accctgccgg    28800
gcacccggag tccggcatt cccctgtcga actcgcgacg cacgtcggtc tgcgtgacct     28860
cggccatcgg ctctccctcc cccgtgactg tgcacggttg ccgttcatat gattgacgtc    28920
aggaaatcat attcggatgc tctcaacggt aaagccttgc atctcaggtg tgttgagccc    28980 cgcccgact tggtagctgc tgaccagcaa tcgttgccct cgtcggagcc gtttccttcg     29040
cacccggccg tcgttcggca gggcatg                                        29067

<210> SEQ ID NO 3
<211> LENGTH: 37146
<212> TYPE: DNA
<213> ORGANISM: Artificial Sequence
<220> FEATURE:
<223> OTHER INFORMATION: Description of Artificial Sequence: Tomaymycin
      biosynthetic gene cluster of Streptomyces species FH6421 in
      plasmid

<400> SEQUENCE: 3
ctttattgct agcgcccggg ccgccgccgc gtcgctcaag ccaggccagg cgtaggccgg      60
ccccgcccgg acacgagacc gcccccctc cgcagccacc ggaacggggg cggtcctatg     120
ccgcaccaga gccaacacac ccttggagga tcaccccgtg acccaatccc ggaagccctc    180
ggaagtcgtc tatctcttag gagccgaggg cctagacctg gtgaagatcg gcaccacgac    240
agacgtggag aggagagtcc gcacgatgca gaccggtctg ccgctgacgc tgtcggtgct    300
gtggacgtgc gagggcggcc gcgcccttga ggggcgctc caccaggagt tccgtgagca    360
caaccggcgg ggcgagtggt tcgacctgac cagccttggt gacccggtgg ccgtcgtgag    420
tgagacggtc cggaggcttg cgccaggtct tgggctcccg atcccgccgc gcgcgtctc     480 gccggacctg gctctaacgc ctgtggcccc cacgattccg gggtgcgtcc ggctggagcg    540

```
caccctgacc gctcggatgc tcgcctggtt cgagtgcgaa gacttcggcc ttccgccctc    600
cgcgagcaag cctgtgatgc tgtaccggac cgtccagtac gacgcgaagg gcgacgtcct    660
ggccgtgacg cagacgctcg ttggcgatgg acacgagcag cctgaaggct tcgagcttcc    720
tcccgtacag ggcggcaact gaccgtctgg cacatagatc agcgccccg ctccgtggga     780 gatcggagcg ggggcgctgt gttgtgcggt caagagacgg ggcggatcgt ccggcggcgg    840
cgagcgtcgg tgttgctgac cttgcgggc gcgcgggcac ggtcgtccgg ggtgaccggg     900
gggtccgtga gggcggcggt gatcatctcg cgcagctcgg ggtgcagcgt gaagtagtac    960
cgggcgttga tccggtagag gccggcgag gtccgcacga ggaggttcag ggcctccagg    1020
cgggcgagag cctcgtgcac cgtggagacg gagttgccgc agtcctcggc gacggtttcg    1080
accggtacgg ggatgacgtc aaacaggccg ccgtggtcct ccacccacgc gagcgtgcag    1140
tgctgagcgg cggacaggtt cagcgagtac agcgacgggg cggtcaggtc gcgctccggg    1200
ttgaagcctt ctacgggcat ggtcgtcatc gcgtctctca tgcggcgcgg cggcgggtag    1260
ccgggatggt cttgggcttg ctggcggacc tggtcatggc cttgtcgtcc ggggccacac    1320
gcggcggcgc catgcggcgg caggcgttga cctgcgtgct cccggctccc tcccagtatc    1380 ggaggggtt cagctggtaa gagccggatc gcgggcccgg cttgaccaca agcccgagct     1440
tgaccagccg gttaagggcc ttccggcagg tgtccttgct ggcgccgacg tcctcgccca    1500
gctcctcggg cgtgaccggg acgtatccgg ccgcgcctcc gtgttcgcgg agccattcga    1560
gcgtcgccca ctccgctgcg gccagcccga gggagtacag ggggacgtcg ctgcctacgg    1620
cctgcaaggt gtaccccttc ccgtcgaact ggtgcggagt ccgcggcctg gcggacaccg    1680
cctctccggt gtccatgttg accagggcca tgttcggccc gcgcttcctc gtcggcactc    1740
gcgcctctcc catcctcgcg ctaaggggcg gttttttgacc ccttagctcc gatgaaccgc    1800
cgcttacgag aggaaactaa caggtcacca ctccgaaaaa cagccgctta gtccgcgtgt    1860
cacacgcata ggtgacgcga cttcctggcg accgggcgcg acgagggacg cacggtgggt    1920
agctaagcgg cgattttga cccagtaacc ggcggttttt agccgcttag ccgcgcgttt      1980
taccaggtca agagcatgcg cccccttcttc actagaaggc gcgcgccgtc actcacgcac    2040
cacggcgcac accgtggtga ccgccctgga ctcctacccg cccggcatac cgggccgctc    2100
ttagcttcta cggggaaggc cggcggtcct gcgcacctgg tcctcgtcgg cgcctacggt    2160
cggcgagtcc tcagccctgg cgggcttgcg ggtcccgact gatgccacct gatcacgcct    2220
ggcgaccgca cgctgtcctc ggccggccac aagcaggaag gaagcgtcgt cctgccggtg    2280
ggcggctgag gtacctccgt accgccgccg ttgtcgcccc cgccgcaggg gttgcctttc    2340
tgtggctgag gtcgattccc ccgccattga tcacccgcac cagggagggc ccagccgacg    2400
aggtggcgcg cgtgcgcacg tcgctgggtg ggggtgcggt aggtaccggg cagcagctcg    2460
gggaccaggc cccggcggc gggggtccgg aggagcccgc cggggtgtg cgcaagggcg       2520 tagcccgtag ccccggagcg cagcggaggg gtcgctagta ggaggccgct atggcgcgta    2580
ccaccagccc acagggtccg gcctccggag gcgacgcact gccggaccgg accgcaaggt    2640
ccggtgagcc cacaacggcg gatcaaccga taagacggcc accgggcagg aagagggtgt    2700
acgcgcccct tggtggcccc tctcgcgcgc gatcacctca cggcgcgtct cccaggtagt    2760
cagatccgtg cggggttctc tacgggccgc acacggcctt cgtcctaaga ggctcttttc    2820
cgccgcttag ctccgaggaa ccgcccctta tctcaatgaa agcgcaggtc accactccag    2880
```

-continued

```
gaaacggccg ggcgagcgac cagccaggag gggagccgcg gatgcgccgg tcctcgacga    2940
tgtagaattc cccaatgtca agcacttccg gaatcgggag cgcggccgat gcaaagtgcc    3000
gataaacata acgatctttg tagaaaccat cggcgcagct atttacccgc aggacatatc    3060
cacgccctcc tacatcgaag ctgaaagcac gagattcttc gccctccgag agctgcatca    3120
ggtcggagac gctgtcgaac ttttcgatca gaaacttctc gacagacgtc gcggtgagtt    3180
caggcttttt catatctcat gccccggga cgagcgtctg ctccgccatt cgccgtccgc    3240
cgtgccaatc ggatcagccg tccaaatgcg ggattttcgt tagtcggagg ccaaacggca    3300
ttgagcgtca gcatatcatc agcgagctga agaaagacaa tccccgatcc gctccacgtg    3360
ttgccccagc aatcagcgcg accttgcccc tccaacgtca tctcgttctc cgctcatgag    3420
ctcagccaat cgactggcga gcggcatcgc attcttcgca tcccgcctct ggcggatgca    3480
ggaagatcaa cggatctcgg cccagttgac ccagggctgt cgccacaatg tcgcgggagc    3540
ggatcaaccg agcaaaggca tgaccgactg gaccttcctt ctgaaggctc ttctccttga    3600
gccacctgtc cgccaaggca aagcgctcac agcagtggtc attctcgaga taatcgacgc    3660
gtaccaactt gccatcctga gaatggtgc agtgtctcgg caccccatag gaacctttg     3720 ccatcaactc ggcaagatgc agcgtcgtgt tggcatcgtg tcccacgccg aggagaagta    3780
cctgcccatc gagttcatgg acacgggcga ccgggcttgc aggcgagtga ggtggcaggg    3840
gcaatggatc agagatgatc tgctctgcct gtggccccgc tgccgcaaag gcaaatggat    3900
gggcgctgcg ctttacattt ggcaggcgcc agaatgtgtc agagacaact ccaaggtccg    3960
gtgtaacggg cgacgtggca ggatcgaacg gctcgtcgtc cagacctgac cacgagggca    4020
tgacgagcgt ccctcccgga cccagcgcag cacgcagggc ctcgatcagt ccaagtggcc    4080
catcttcgag gggccggacg ctacggaagg agctgtggac cagcagcaca ccgccggggg    4140 taacccccaag gttgagaagc tgaccgatga gctcggcttt tcgccattcg tattgcacga    4200
cattgcactc caccgctgat gacatcagtg gatcatagca cgatcaacgg cactgttgca    4260
aatagtcggt ggtgataaac ttatcatccc cttttgctga tggagctgca catgaaccca    4320
ttcaaaggcc ggcattttca gcgtgacatc attctgtggg ccgtacgctg gtactgcaaa    4380
tacggcatca gttaccgtga gctgcaggtc gacggatctt ttccgctgca taaccctgct    4440
tcggggtcat tatagcgatt ttttcggtat atccatcctt tttcgcacga tatacaggat    4500
tttgccaaag ggttcgtgta gactttcctt ggtgtatcca acggcgtcag ccgggcagga    4560
taggtgaagt aggcccaccc gcgagcgggt gttccttctt cactgtccct tattcgcacc    4620
tggcggtgct caacgggaat cctgctctgc gaggctggcc ggctaccgcc ggcgtaacag    4680
atgagggcaa gcggatggct gatgaaacca agccaaccag gaagggcagc ccacctatca    4740
aggtgtactg ccttccagac gaacgaagag cgattgagga aaaggcggcg gcggccggca    4800
tgagcctgtc ggcctacctg ctggccgtcg gccagggcta caaaatcacg ggcgtcgtgg    4860
actatgagca cgtccgcgag ctggcccgca tcaatggcga cctgggccgc ctgggcggcc    4920
tgctgaaact ctggctcacc gacgacccgc gcacggcgcg gttcggtgat gccacgatcc    4980
tcgccctgct ggcgaagatc gaagagaagc aggacgagct tggcaaggtc atgatgggcg    5040
tggtccgccc gagggcagag ccatgacttt tttagccgct aaaacggccg ggggtgcgc     5100 gtgattgcca agcacgtccc catgcgctcc atcaagaaga gcgacttcgc ggagctggtg    5160
aagtacatca ccgacgagca aggcaagacc gatccccggg gacctgcagc aatggcaaca    5220
acgttgcgca aactattaac tggcgaacta cttactctag cttcccggca acaattaata    5280
```

```
gactggatgg aggcggataa agttgcagga ccacttctgc gctcggccct tccggctggc    5340
tggtttattg ctgataaatc tggagccggt gagcgtgggt ctcgcggtat cattgcagca    5400
ctggggccag atggtaagcc ctcccgtatc gtagttatct acacgacggg gagtcaggca    5460
actatggatg aacgaaatag acagatcgct gagataggtg cctcactgat taagcattgg    5520
taactgtcag accaagttta ctcatatata ctttagattg atttaaaact tcattttttaa   5580 tttaaaagga tctaggtgaa gatccttttt gataatctca tgaccaaaat cccttaacgt    5640
gagttttcgt tccactgagc gtcagacccc gtagaaaaga tcaaaggatc ttcttgagat    5700
cctttttttc tgcgcgtaat ctgctgcttg caaacaaaaa aaccaccgct accagcggtg    5760
gtttgtttgc cggatcaaga gctaccaact cttttccga aggtaactgg cttcagcaga     5820
gcgcagatac caaatactgt ccttctagtg tagccgtagt taggccacca cttcaagaac    5880
tctgtagcac cgcctacata cctcgctctg ctaatcctgt taccagtggc tgctgccagt    5940
ggcgataagt cgtgtcttac cgggttggac tcaagacgat agttaccgga taaggcgcag    6000
cggtcgggct gaacggggggg ttcgtgcaca gcccagct tggagcgaac gacctacacc     6060
gaactgagat acctacagcg tgagctatga aaagcgcca cgcttcccga agggagaaag     6120
gcggacaggt atccggtaag cggcagggtc ggaacaggag agcgcacgag ggagcttcca    6180
gggggaaacg cctggtatct ttatagtcct gtcgggttc gccacctctg acttgagcgt     6240 cgattttgt gatgctcgtc aggggggcgg agcctatgga aaaacgccag caacgcggcc    6300
caattgaggc ctaagcttca tatgttaatt aaactaggtg tccgcacgca tgagcgtgcg    6360
acatttccga ctatcaaccg gaaacggaaa gatagtgacg gctacgttat ttccgtcccg    6420
gcaaatcggg caataactct attcagtgac tcgactgcgc cctgatcgtg gcgtatggcc    6480
gtgcgacggc ggcgagaggc cgtcggccga ccgtggcccg caacacagcg gcgggaagaa    6540
ccagttgggg cccaagcgcg agggagcgcg caagatccga cgggaaccga gccccggcc     6600 ccctcgtcgg cgttgtcatt cgaaagaaat acgtaatgac cgctcaagtg tggccaattc    6660
cgctccgggc gtacgctggc gcactaaatt cagggtcggc gtaagaatcg agcgagggcg    6720
gacggagcgt tgcaggaacg ggcgaaagca acccgtagat cactgctgga agcggctgcc    6780
cagctcttcg ccgaacaggg atacgcggcc accagcgtca acgacatgag cgcccggtcg    6840
ggccggacca gcggcgccgt ctacttccac tacgccggca aggaggccgt cgccgtcgcc    6900
gtcgtccagg accggttcgc cacctggcca cagctcgccg cacgctacgc ggacgaggcg    6960
gtcccccccg tcgaccggct cgtcgccctc agctacgaca tcgcccacgc tctcgccgag    7020
gacccggtga cgcgtgccgg cgcccgcctg tgggccgaac gcgccaccat caacgttccc    7080
cttccccacc ccttcgcgct gtggaccacc gccgccacac gactgctcgc gaaggcccgg    7140
ctcgccggcc acctccaccc gcatgtccgc cccgctcgcg cggcccggac cctggtccct    7200
gccttcttcg gcctgtgcgc gctcaccgag gaactcgaag gcacggccgc cctcaccgac    7260
cgcctgaccg actggtggca gctgacgctg ccctgcctcc gcccgcaccc ggtgcgcgag    7320
gacctgccgc gcgggcggtg acgcgcggca ggtcccgtag ctccggccgc tgtcggagca    7380
cgggcggcgc gttacgggga ccgcgccggg taggcccgt ggctcaccgc tcgcggacac     7440
cctgaacggg gagatgaggg gcgcggcttc cgccgtgacg ccgcggtccg ggaagccgtg    7500
gtgttcgagg aagcccgcga ttgtcgagcc cgcgcggcag cgccgccc tcggccggac      7560 agcgcgtcgc accgcccgta cagcggccac cagcaggtcc ggtgggtgcg gataccgggt    7620
```

```
ggtgcggccg cgcacgcggt gggtgcggac gtcgggtggt gcggcggcgt acgccgtggg    7680
gacgggacgg ggggcgtcgc gcatgcggtg gctgcggatg ccgggcggtg ccgccgtgca    7740
tgccgcgggt acggacgctg ggtggtgcgg cggcgcacgc cgtggggtg gggcgggggt     7800 gccatgggtg cggacgccgg gcgctgcggc ggcgtacgcc gtgggccggg gcggaggtgc    7860
cgtcacgcat gccgtggctg cggacgtcgg gtggtgccgc cgtgcatgcc gtgggtgcgg    7920
acgtcggcgg cggcgtacgc cgtgggccgg gaccggggggc tgtcacgcat gccgtggctg   7980
cggacgtccg gtggtgccgc cctgcatgcc gtgaccgcgg acgccgggca gtgccgtcgc    8040 gcacccatg gggccggggc gggtggggcc tgccggtatc cgggtggggg cggtaccgcc     8100
cacgccgacc gcgccgcccg cccggcaccc ccgcccgcgg ctcagggacg cgcctccacc    8160
ggttcgaggt gcggttccag ggcgccgcg accttgtggc acagctccac gaacatcgcg     8220
cgctcacccg ggctcagtgc ggcctccacg atgcgggcgt tctcccgccg ttgctcggcg    8280
acgcgggtga ggaaggcctc gccggccggt gtgagcgagg tggtgagttc acgccggtcc    8340
tcgccgagcg tccgctggtc gacgagctcc aggtccttga ggacgcgcag tgctttggac    8400
gtggtcgccc gcgacacacc gagcgaggca ctgagcaccg agggagtcat ggggccgcgg    8460
atgcgcagca gctccaggac gtcgtactgc tgccaggtga cgccttccgg attcgagcga    8520
gtgcggcggg cgacgaggat gcactgcaag tgggaaagcg cgtcctcgag ttcgcctggc    8580
acagccgagg tctcggaggc gcttcgtggg ctgtcggttc gggtcatcaa cgccctcagg    8640
tgatcaggtc ggggacgagg cgccacggcc ggctcggggc gggagcgggc cgacggcgac    8700
ctccgattgg ttacccatta tcaacgatcc tggggcggca acgtataccc ctccacacgg    8760
tcatgtgatc catcgcccaa cagttgtttc catcgggaaa atttctacgc gatgatctct    8820
gatgagtggc cctccaggcc ggacacgcgc gcgcctcgc tccggctttt cccggcccgc     8880
gagcgggagg cgcccctcgg gcgggccccc gtggacggca gggcgccgtc ggccgggcgc    8940
tctggtttgc tccggtcgaa caatggctga tgcatcgtca gtgactcggt tgctttcctg    9000
gcggtaaaca agtggctgaa aacgcgccct gcgacgctgc gctccaccgt gtcggcctgg    9060
ggttgtccgt ggcggcgaag gggcctccgg tcggggcccg acagcccagg catgggagcg    9120
aagagcgggg gtagtggcag ctccagcgtg ggtggcgcag cggtctcggc gcctcaagat    9180
cggggttgac acgtcgaaga gcgccgacct aacgtgattt ccgaacagca accatcacct    9240
ttcggttgat ttgtgcgtat tccttgagaa gccggtcact ggacgtcgga tgtgctcgtc    9300
gctgtgggcg ccccgtggcc atccgccagc gaggcaagga gcacgtgtgc tcacggagaa    9360
tgcatcaggc gaggcgcgtt ccgctgttcc cctgaccctc accgagggtt tcgaccgcgt    9420
ggtgcgggcc gccggccacc aggtcgccct cgtctccggc acggagaccg tgacctaccg    9480
gcaactgaac gaacgagccg agcgcgtggc ccgcgggctg ggcgcccgca aggtggcgcc    9540
cggtgaccgg gtcggcgtgt atctgcgccg gtctcccgac ctctacgcgg tcatgctcgg    9600
cgtcctcaag gcgggcgcct gtgtggtgcc ggtcaacccg gaccaccctg cgccgttcgt    9660
ctcccgcgtg gtggccgaat cagcgccgcg ggccgtcgtg cacgacgcgg gaacaccggc    9720
cgtcgcgccc gctgctccgg gcgcaccgct gtgggtaccg gtcgaggagc tcaccacggc    9780
cgcggaaccg gacgacggcg tcgcgctgcc cgccgtgaac gatccggaca gcaccgcgtt    9840
cctgatgttc acctccggat ccaccggccg gccgaagggc gtccgcatcg cccaccgcgg    9900
gctggcacga ctcggcccgt acagcgggga actgcgcatg ggcccgcagg actgcctggt    9960
ccagtccgcg gcgttctcct tcgccgcgtc caccatcgag atctggctcg ccctcctgca    10020
```

```
cggcgcacga ctcgtcgtga tgccccaggg gctgcccagt ctcccggccc tcaaggacgc   10080
cgtcgtccgg cacggcgtca ccgcgctgtc cctgccctgc ggtctgttca acctcctggt   10140
ggacgaggag ccggaatgcc tgcggggcct gagggtgatc ctcctcagcg gcgacttccc   10200
gtcgccggag cacctcagcc gtgcggcacg ggcgacgcgc gcggtcatct acaacggcta   10260
cggctgcacc gagaactcct ccatcaccgc cctgtacccc atccgcgatg ccggggacgt   10320
cacccgcgag aaccgggtgc cggtgggccg ccccctgccc ggggtcaccc tggaggtact   10380
cgacgactcg ctgcggccct gcccgcccgg aacgcccgga cagctcgtcg tcggcgggct   10440
cggactcgcc cagggctatc tgaacgaccc ggaactcacg aaccgcaagt tcgtcaccgg   10500
gccggacgga cggccgcgct acctgaccgg cgatctggcc cgcgccaccg aggacggtga   10560
catcgtcctc ataggccgcg ccgacagcat ggtcaagatc cgcggctacc gcgtcgaact   10620
gaccgcggtg accctcgccc tgcgcgccct cgacgggatc ggcgacgccg tcgtcaaggc   10680
gttcccggag ggcgccgggg agaagtcgct caccgccttc tacaccaccg tcgacggacg   10740
accgctggac ggtgccgacc tggcacgccg catgggagac caactgccct cctacatggt   10800
cccctccacg ttccaccacc tcggcgacct gccgagaaac gccaacggaa agatcgaccg   10860
gtccgccctc acggacccgt cggacaccaa ccgcgatccg aagaaaggtc acacagccgt   10920
gcagaacccg ctcgagaccg tcgtactcca ggcgtggaag gacatctccg gcgccgacga   10980
cttcaccacc accgactcct tcctcggcca cggcgggaac tccctgcact tcgtccagct   11040
cgcctccagg ctgcagaaga tcttcggtgt ggaggtcagc accgaggacg tcttccggca   11100
cggcacggtg gagcagctgg cgcgcttcgt cgagcagtcg cgggacaccg gacgcaaccc   11160
cgccgcacag acccagtagg cgtcacccgg ccgtggccgt gcggcgcccg tcgcggcgg   11220 ccggggcatc tctgcagagg actacgaccg gtgaactccc ccctccgaac caccgtgctc   11280
gaccttgcac ggaccaccct cggcagcgcc gacctcaccg cgcacgaacc gttggccgac   11340
cggtgcgaac accggcccct gctcgacgac ctcgccacca cgctgaccgc cgtcttcgcg   11400
gtcgagatca ccggcgcgga cctgcgcgcc ggtgccaccg tcgccgacgt ggccgcgcga   11460
atggacgacc ggcgcgacgc cccccggatc ccggaactgc gcgccgggct cgctccccgc   11520
gacggccggg cggtggaggc gtccttcggg cagagcggca tctggctgat cgaccagtac   11580
ctgcccaacc cggccgccta caacggcccc ttcttcgtcc ggctgccgtt ctcagccgat   11640
cccgaccgcc tgcacgcggc cgtgcgcgga gtgctgcgcc gccaggaggt cctgcgcacc   11700
acctacgccc tgagcgacgg cacgctccgg cagaacgtct cgcgggacga tgacgcggtc   11760
gtcttcgagg tagcccgcta cggcgacgac aaggaactcg acgccctcgt ccaccgggtg   11820
gccaatctcc gcctcgacct ggcccgcggg ccggtcatcg ccgtgacctg cgcgctcggc   11880
cccgcgaacc ggtccgccgt catctgcaac atccaccaca tcgcctccga cgccgcctcc   11940
gccggtgtct tcctgcggga actcctcgac gcctacgacc gcctcggccg cggtctgccc   12000
gtcgaggccg acccgctgcg gcccacctac ggggacttca gccagtggta ccgggaactg   12060
atgaaccccg aggccctcac ccgctccctc gaccacttcg ccgccggct cgccggggaa   12120 ctcccggtgc tcgacctgcc caccgaccgg ccccgcccgc cggtgaagca acaccggggc   12180
ggcaccctcc cgttgcacct gccggccgcc gcggccgacg acttcgaggc gctcgcccgg   12240
accgaggggg tgaccctgtt catggccctc gtcgccgcgt acgcggtctt cctctcccgc   12300
cacaccggtc agcggcgcgt gctgatcggc agccccgtct cgctccgcga cgacccgcc   12360
```

-continued

```
acccacgaac tgatcggcta cttcgtcaac ctggtcgtcc ttcagcagga gatcgacgac    12420
cggatgaccg tccgggacgt gctccgccgg gcgcgggagg aggtgagcga ggcgctgcgg    12480
cacaagtggg cgcccttcga caaggttgtc gagcgtctgc agccaccgcg cagcagcggc    12540
tacaccccgc tcgtgcagac catgctcgtg ctcacccagg gcgacgccgg acggatatcc    12600
cacgacgaca cggaactgcg catcgagcgc ggggccgcgc acggcgccaa gtacgacctg    12660
tccctcgttt tcgagcggga ctccgaaggc ctgcacggtc tgatcgagta cgacgcggac    12720
ctcttcgacg agccgacggt acgggccatg gcgaccggc tgcggcacct gatggagcag    12780
ttcgcccgac gtcccgacgc acccctgcac gaactggagg cgctcggtgc gcaggagcgg    12840
cggtcggtgc tggtccgcgg ggaccggacc gcgcacgccg tgcacgacgc acccgtcatg    12900
gaactgttcg aggcccaggc ccgggcgacc cccgacgcgg tggcgctgga ggacggcgac    12960
accaccctgt cctaccgcga actcgacgag cgcgccaacc ggctcgccca cgtgctgcgc    13020
gcctccggcg ctgcggccgg cacccgggtc gggatctgcc tgccccgctc ccacgacatg    13080
gtcgtcgccc tgttcgccat cctgaagacc ggggcggcgt acgtaccgct cgacccgtcc    13140
taccccaggc agcggatcac ccacacgctg cgcgacgccg gggtcttcct gaccgtgacg    13200
gacagctcac tggccgacga actcccccg agggagccgc tgttcgtgct ggaccggcac    13260
gacggaccga tcgccgcggc cccgccacc ggcctcggcc gggtgaagac acccgacgac    13320
gagatctacg tcgtgcacac ctcgggctcc accggcctgc caaggggggt ggtcatcgcc    13380
gaccggaccg tcgccaacct cgtccgggcc cagcaccgtt gctcgccggc cggagcgacc    13440
gggcggacgc tccagtacat gtcgctgtcg ttcgacgtgt ccgtgatgga gatcctcggc    13500
accctgtgcg tcggcggcac cctcgtgctg gtctccgagg aactgcgcaa ggatctgcac    13560
gcgctcgccg gattcctcgc cgaacgccgc gtcaccccgg gtgtacctgcc ctacatcgcg    13620 ctccagcagc tggcctccct ggccaccgac gccggtgtgc gcctggacga cctgcgcgag    13680
atcacctccg tcggcgaggc cctcgtggtc tccccgcaga tccgggagtt cgccacccgt    13740
cacccggcgg tccggctggt gaacatgtac gggccgtcgg aaacgcacct ggccagctgg    13800
tacccgctca ccggctcgcc cgcgacctgg cccgacaggc cgccgatcgg ccgcccggtg    13860
gacggcgtgc ggctggtggt cctggacgcc cacatgcggc tcgtccccc gggtgtcccc    13920 ggcgagctgt acatcggagg gcccgtgctg tcccccggat accgcaaccg tccggacgag    13980
acggcccgcc ggttcctccc ggacccttc ggcggccccg ccgaccggct ctaccgcacc    14040
ggcgacctgg tgcgctggaa cagcgagggc gacctggagt acctgggccg gaccgacgac    14100
cagatcaaga tccgtggcta tcggatcgag cccgccgaga tcgaggccgc actcgacgac    14160
ctggacggcg tcgcctcctc cgcggtcgcc gccgtggacg tcgccccgg cgaccgcaga    14220 ctcgtggccg tcctggagac ctcccgcacc tgggagaccg cggagctgcg ccgcgccctg    14280
tccggcacgc tgcccgacta catggtgccc gcgctggtgg tcgcggtgga gcacatgccg    14340
acgaccccga gcgggaagat cgaccgccgg gccgtcgccg gcctggccgc ggcacaggcg    14400
accgcggcac ggaccgcgcc cgcgccaccc ggccggccgc ccaggccggg cctggagcag    14460
cggatcgcgc gggagtgggc ggatgtgctg aaggtgcccg cggtgggcag ggacgaggac    14520
ttcttctccg tcggagggaa ctcgatcatc gccacggaac tggtctatcg gctgcgccgg    14580
gcgttcgacc aggacctctc gctgcgcgcc ctgctggaga tccgacggt cgcgggcatg    14640 gccgcccggc tgcgttccgg ccccggcgct cccaccaccg ccccgccgc gctgcgggag    14700 gacgcgacgc ttcccgacga cctgcccgcc gtcaccggca ccccggtacc ggtcgcccgg    14760
```

```
gcccgtgagg tcctgctcac cggcgcgacc gggttcctcg gcagctacct gctgcgggag   14820
ctgaccggaa ccaccggcgg ccgggtgcac tgtctggtgc gggcggcgga cgaacgggcc   14880
ggcatggagc ggctgcgggc caccgccgag cgctaccggc tggacgggcg gatcgactgg   14940
aaccgggtgc gcgccgtgcc cggcgacctg agccggcccg ggttcggtct gcccggtgcg   15000
gagtacgacg cgctggccgg caccgtcgac gtcgtctacc acgcggccgc gcacatcaac   15060
ttcgtgctgc cgtacgcctc ggtgaaaccg acgaacgtgg acggcttccg ccacgtggtc   15120
cgtttcgccg cgacggaccg ccccaagcac gtgcagtaca tgtccaccat cgccgtgttc   15180
cctccgggcg aggcgcccga cggcacggtc ctcaccgagg acgacgtgcc cgaggcgtgc   15240
gaacgactgg gcatcggcta cacccagagc aagtgggtcg ccgagcgcat cgcactcgcg   15300
gcccgcgcgc acggcgtgcc ggtcaccatc caccgcatcg gcgcatctc gggcgacagc   15360 gtcacaggcg cctgccagag cgacgacttc ctgtgcggc agatcaagag cttcatcgaa   15420
ctcggctcgg ccccgccggc cgaggacctc accaccgatc tgctgcccgt cgatttcgtc   15480
gcccgcgccg tcgtcgccct ctcccgccac cccgccaccc acaaccgcac cctgcacgtc   15540
ttccacccga gcggatcgga cttcaccccg gtccacgcgg ccctgcgcgc ggacggccac   15600
cgcctggaga tcgtcccggc cgacacctgg cttgcccggc tggaggagtc cgcacggcgg   15660
cccggcggca acgccctggc ggcagccgtg cccctcttcc gcgagggcgc cctgaactg    15720 ggcgacaaca cctacggcaa caccgccacc acccgcctgc tgatggacct cggactgccc   15780
tggcccgcca tcgacgagca ggcgatcacg cggatgctcc gctacttccg ctccgtcgga   15840
gaactggccg acgactgagg ggacttccct gtcccgggcc ctcccggcag cgcggcgcag   15900
ccgccggcgc cgatccgacc atccaccaca cggcaatcgc cgaagcggtc gccggacacc   15960
gaaagcacca gcagccatgc caacgagctc ctgccccgac accgcatacg acaccctcat   16020
accctccgtc gtcgcggctc tcccggccgc acagcagccg gagtggccgg accccgggcg   16080
actcgccctc gtccacaccg aactggcccg cgcggacccg ctggtgacgt acgacagcgt   16140
gcgtgccctg cgccggctgc tgtcccgtgc cgccgaaggc gaactgtgcg tcctccaggc   16200
cggcgactgc gcggaggacc ccgccgagtg cggcccggcc ccgctggccc gcaaggccga   16260
gatgctggac gtcctcagcg acatcgtgcg aacgggcgcc ggacggccgg tcgtccgggt   16320
gggccgtgtc gccgggcagt acgccaaacc ccgctcccac ccggaggagc tgcacgacgg   16380
cgtccggctg ccggtctacc gcggtcccat ggtgaacgcc cccacccccg acgccgacgc   16440
gcgccggccc gatcccgccc gcatcctgag ctgctaccgg gccgcccgcc gggccgtgga   16500
gtccctggac cggctgggcc gcggcgaggg ttcgcccgcc gagacccggg tgtggaccag   16560
ccacgaggca ctgctgctcg actacgagct gccctcgtg cgccggcacc gctcgggccg   16620
cagttacctc gccagcaccc actggccgtg gtcggcgaa cggacccggc aaccggacgg   16680
tgcccacgta cggctgctgg cggaagtgga caacccggtg gcgtgcaagg tcggcccgac   16740
cacgaccgtg gagcaggtgc tcgccctgtg caccgcgctg acccggagc gctcaccggg   16800 ccggctgtcg ctggtcgccc ggttcggcgc ctcccgcatc gacggcctgg ccccctggt    16860 ccgcgcggta cggcgggccg gtcacccggt gctgtggctg tgcgacccga tgcacggcaa   16920
cggtgaacgc accgcgcacg gactgaagac gcgccggctc agcgccgtga tggcggagat   16980
cagccggttc gtggacatcg tctccgccga gggcggccgc agcgccggcc tgcacctgga   17040
ggcctcaccg gacgacatcg ccgagtgcac cggcgccgga ttcaccccgg ccccgggcc    17100
```

```
ggcctaccgc accctgtgcg atccccgcct gaacctggtg caagccgtcg cggcgaccgc    17160
ctactggcgg ctgccggccc tggaggccgt cgcatgagcg agtctgcgcg gaacgcgcgc    17220
ggcctggcgg ccctgctgcc cccgccgggc accccttcg ccgtcctgca ccggccgggt    17280
gccgggcacc ctggcaccgt ggacgtcgtc agcgggcccc tccgcaccgc cgccaccctc    17340
gccgagctga gcctcgacga cgagtccgcg ccggcctccc agggcccgg accggcgcac    17400 agggtcctcg ccctggtgcc ccaccggcag atcgccgaac gaggcttcgc ggctcccgac    17460
gacggcaccc cgttgctggc catggacatc ggcacccagc acaccgtgcc cctggagcgg    17520
atgctggcac tcctgcccga ccgcgaactg cacgtcgagg aaaccgggtt cgacctcgac    17580
gacgaccggt acgcggccgg cgtcgacgcg ctcacccgcc aggagatcca gcgagggcag    17640
ggcgcgaact tcgtcctcgc ccgcagcctg cacggccgga tccgcgactt cgaccggacc    17700
cgggccctgg ccgcgctgcg gcggctgctg atcgcggaga gcggcgccta ctggacctac    17760
ctggtctgca ccggcgaccg gtacctcatc ggcagttccc ccgagcagca cgtacgggtg    17820
gccggctcgc gggtgtcgat gaacccgatc agcggcacct accgctaccc cgaggggggc    17880
cgcccggacc gcgaaagcct cctccggttc ctcgccgacc ccaaggagat ccacgagctg    17940
tacatggtcg tggacgagga actgaagatg atgaccgaac tgtgcggttc ccgcgtgcgc    18000
gtgtcgggcc ccacgctcgc gtggatgtcg cgtctcgccc acacgcagta ccacctgcac    18060
ggcgagtccc cgctgcccct gaccgacatc ctgcgcggga cactgccgc gcccacggtg    18120 acgggcagcc cggtggagaa cgcctgccgg gtcatcgccc gccacgaacc ggcaggccgg    18180
ggctactaca gcggcgtgct ggcgctggcc ggccaggagg ggggacggcg cgccctggac    18240
gcggtcatcg tgctgcgcac cgccgacatc accgcggacg gatccgtgcg gctgaccacc    18300
ggcgcgaccg tggtgcgtga ctcggtgccc gcgcaggagg cggcggagac cacggcgaag    18360
gccgcggggc tcctcaccgc gctgacccgc ggcccggccg gccggtccgc ggccccggcg    18420
cacgcggcac ccgacgtctc cctgggagcc gatccggcgg tgcgcgcggc gctgcgctcc    18480
cgcaacgacg gcatcgccgc cttctggctc ggcggcgggg cgcgcctgcc ggcgccctcg    18540
ccacacggac cacgggtggc ggtgatcgac gcggaggacc ggttcaccag catgctcgcg    18600
cagcagctcc gcgcggtggg ctgccacgtc accctgcacc cctggtggtc ggttccggag    18660
gcagccgacg accccggcac cgtgctgctg ctggggccgg gacccgggga ccccggggac    18720
gtcggcgacc cgcgggtggc gcggctgcgc tccctggccg gccgccggct cgcccggcgg    18780
ttgccgctgg ccgcggtgtg cctcggtcac caggccgtct gcggggtgct gggccttccc    18840
ctggtccggc tcgcgcggcc ccgccagggc gcccggatgc gggtcggcct gtggggacgc    18900
gaccggcacg tcggcttcta caacagcttc accgcgcgct ccgacaccga tcgctgtccg    18960
ctgcccggcc gggacgccac ggcccgggtg tggcgccggg acggggaga cgtggtcgcg    19020 ctggacggcc cggggctggc caccgtccag ttccacgccg agtcgctgct caccgaggac    19080
ggcccggaca tcctgcgcga gctggtggac cgggcggccc gtaccgagcg gcgcaccgag    19140
gccctgatgt cccgccgagc caaggagcac gcgtgaaccc gcccggaacc gtcgtcgcca    19200
acgccgccct ggacccccgg gagctgcgcc ggaccatggg gcacttcgcg accggcgtca    19260
ccgtgctgac ctgccggcgc ggcgcccggc tgcacggggc gacggtgaac tccttcacct    19320
cggtgtcgct cgatccgccg ctcgccctgg tcgccctgga ccgtcgcacc cgcgccgccg    19380
ccctcctgga cgacggcccc ttcgtcgtca atctgctcgg cgagcaccag caggacctgg    19440
ccctgcactt tgccggcggc tcgccggccg attccgtgcc gtgggtggac ggcgacggcg    19500
```

```
accggccccg gctggcggga accctcgggc acctggtgtg ccgaccctgg cgcacctacg   19560
acggaggcga ccacacgctg catgtcggcc gtgtcgagga gttcgccgcc ggaggggggac  19620 ggccgctgct cttctaccga ggcgtcttcc cccgcctcat gccggacgga ggaggagacc   19680
cggagggacc cgaggaggtg tggtcgctct gtctggacgg cccaggaccg ccacggatc    19740 agttcgtcac cgatcatgag acacggaagt agggacatgg caccgacaa cggacagtcc    19800 gcagcacccg gcacctccgg ggcgtccacc ggcaaggccc gggtcacccg ccgctgacc    19860 ggggacgagt acatcgagag catccgcgac ggacgggaga tctgggcgta cggcgagaag   19920
gtcgacgacg tcaccaagca cccggcgttc cgcaacaccg tgcggatgac ggcccgcttg   19980
tacgacgccc tgcacgatcc cgagcaccac gacaccctga ccgcgcccac cgacaccggc   20040
agcgacggct tcacccacaa gttctaccgg gtgccgcgca gcgtgcagga cctcgtgggg   20100
gacagggacg ccatcgccga ctgggccagg ctgacctacg gctggatggg acgcagcccc   20160
gactacaagg ccagcttcct ggtgaccctc ggcgcgaacc ccgactacta cggcgacttc   20220
gcggacaacg cccgccggtg gtacgccacc gcccaggaga acgtgctgtt ctggaaccac   20280
gcggtgatca accctccggt cgaccggcac cggcccgccg acgaggtgga cgacgtcttc   20340
gtgcacgtgg agaaggagtg cgacgacggg ctggtggtga gcggggcgaa ggtggtggcg   20400
accgggtccg cgctcaccca cttcaacttc gtggcgcact acggactgcc cgtgaagaag   20460
aaggagttcg ccctcgtcgc caccctgccc ctggcggcac ccggcgtgaa gctcatctgc   20520
cgccagtcat acgaactggc cgcgagccgc acgggcagcc cgttcgacta cccgctgtcg   20580
agccggctcg acgagaacga caccatcttc atcctggaca aggtgaagat cccctgggag   20640
aacgtcctca tctacgggga caccgccagg gccggcacct tcctgcagac ctccggcttc   20700
acccaccggc tcaccttcca cggggtgacc cggctggccg tgaaactgga cttcctggcg   20760
ggcctgctgc tgaagggcgt ggaggtcacc ggcaccaagg acttccgggg catccagacc   20820
cgggtcggcg aggtcctcgc ctggcgcaac atgttctggg cactgagcga cgcgatggcg   20880
cacaaccccg atccgtggca cgacggagcc ctgctgccca acctcgacta cggcatggcc   20940
taccggtggt tcatgaccgt cggctacccg agggtccggg agatcatcat gcaggacctc   21000
agcagcgggc tgatctacct cacgtcgcac gccaaggact tcaacgaacc tgaactccgt   21060
ccccatctcg accgcttcat gcggggttcc aacggttacg aggcggtgga gcgcgccaag   21120
ctgatgaagc tcatctggga ctcggtgggc accgagttcg cgggccggca cgagctgtac   21180
gagcggaact actccggcaa ccacgagagc gtgcggatcg aactgctgca cgcccagacg   21240
gcttccggtc tcgtcgacca gtaccggggc ttcgccgaac agtgcatggc ggaatacgac   21300
ctggacggct ggacggcacc ggacctggtg ccgcccgacg tcgactgagc gccgcggcca   21360
tccggccgga cgggcccgcc gggcggtacg gcagggggcgg gaggagcccc cccgcccct   21420 gccgctcagc cggtgaccag ggcgagcgtg aaaccgtcgt accccttggt gccgacggtc   21480
tggatcgagg tggcggtgac gtccgagcgg ccggccagca tctcgtggaa ccggcgcacg   21540
ccctggacgc cggcgtcggg atggtccggg tcggtcaccg cgccgcccag gacgacgttg   21600
tcgacgacca ccaccgcgcc cggccgggac agtttcagcg cccaggtgaa gtactcgggg   21660
atgtcgggct tgttggcgtc gacgaacacc atgtcgaagg gggcggtacc gggccggtcg   21720
agggtcggca ggatgtccag cgcccggccg acgtgctgtt cgacgaggtg ggcgacccc    21780 gcctcggcga ggcgcgacgc ggccgactcg gcgaaggacc gctcccactc gatggtgacg   21840
```

```
aggcggccgt ccggcggcag cgcgcgggcc agccagatgc tgctgtaccc gccgaacgtg   21900
ccgatctcca ggatgcgccg cgcctgccgc agacgcgcca gcagatgaag gagtttgccc   21960 tgggggcgc tgacggcgag gtccggcagg tcgaattccc tatgggcctg agcggccttc    22020
gaaagtgctt cgtcctcctt cacgagaagg gagctgaagt agacgtcgac actgttccat   22080
cgctcttgtt ccatggttgc aataattcac gataaaccct cggatggcaa gagcagaatt   22140
cgatatccat ggtgccgtga acctgagaat gcccaggtca gcggcctatt caaggctgtc   22200
cagtcacctt cgccaaagaa attaacgggc ggtcgataat gttcggaaat tccttcggtg   22260
cggcgttgac tgtcgtcctt gcggtcacct agcctcccct tctggaacct tgtgaaaaag   22320
cctgtcccgg ataggagtgt catttcatgc gagaagactc ggccgtcaca acggccgcac   22380
ccccggtgca cctggtgccg gcgatgcacc acctgggcgt ccaaacccgc gacctggaca   22440 actcctggc gtggtacaag gacttcttcg gctgcgccga gacctggacg ctcaccacgt    22500
tctcggacct gacccgcagc aggctccccg gcatcacccg gctcaccgag atcagcgtcg   22560
ccgacgtccg cttccacctc ttcgaacgcg ccgggcacga cccggccctg ccggcggca    22620 acaaggccca gttccagcac gtctgcctcg ccaccggttc cccggaggaa ctgcgcgcct   22680
ggcgcgatcg ctggatcgag ctctaccgct cgggccgcta cgacttcgcg accgatgagc   22740
agcccacgga catcgtggtc gacgccgacg gagtgcacag ctgctacctg ttcgaccccca  22800 acggcctcga gttcgagttc acctacgttc cgggcggtgc ggcatgagcg cgggcccgca   22860
ccggaccgtc accgaactgc cggtcgccga aggctgggac ttcggggact tcccctacgg   22920
cctggagccg ctgaccctgc ccgagccccc gcacgagccc gcggccgacg ttccggacgt   22980
gctgtgcgcc gagcccgccc ccggcggtgc gcggacgtcc tgcccgcgca ccggaccggc   23040
gcccggcctc ccggagctgg cccaccagct cttctggttc cgctggatca ccggacacca   23100
gctgaccttc gccatctggc agttactcgg ccacgcgctg caccaggcgc acgcccggcc   23160
cgaccccggc ccgtcgctgc gagccatgac ggacctgaca cggggcgtaca ccgcgatgct   23220 gctctacacc ggctcctgtc ccaaggacgt ctacagcgac gtgatccggc ccagcatgtt   23280
cctgcagcac cgcggcttca gcgggacctg ggcgccggac ttcgtccccg tccgccggct   23340
gctgcggggc aggaagacgc cgtggcacga gaccccggag ggcggccggc tggccgacga   23400
ggtccgtctc taccacctgg tgcactcggg ggtcgccgcg aaactcgtac ccggcggcag   23460
gtccctgctc caggacaccg cccccacggc ccggccgcac gaccccggga tgcaggcgct   23520
ggtctacgac aactacttcc tcaccctgcg cgccgacgtc ccgaccgccg aggtcgtcga   23580
gcagctccgg cgccgactgg ccgcggtgcg cctggacgtc tcggtcaacg ggctgtaccc   23640
cgggctgacc gcgcaggagg acgccgcact gcccgaggag ttgcgcagcg aggacacaca   23700
ggcctgcgag cgggacttcg acgccgtcct gcggcgcgtc gacggccttg ccgccgcact   23760
cgaccggcgg ttgctcgacg gcacgatcgc ccgctgagcc tgagccaccc gatcacgcga   23820
caggaaagga gcggtggacc gtgcggtacg gagtcgtcgt cctgcccgaa cgccggtggg   23880
cgcaggcccg cgaacagtgg gtccgtgccg aggagttcgg attcgaccac gcctggacct   23940
atgaccagct gatgtggcgt tggctgcgcg acgagccctg gttcggcgcc gtgcccaccc   24000
tggcggcggc ggccgaggcc acctcgaccc tgaccgtggg caccatggtg gccacaccca   24060
cctatcggca cccggtgacg ctggccaagg aggtgatgac cctcgaggac atcgcgggcg   24120
gccggttcgt ctgcgggctg ggagccgggg ccggcggcct cgacgaccgc gtcgtcgatc   24180
cggccgccta ctccccacgg caacgcgccg accgcttcac ggagttcgtc gacctgctcg   24240
```

```
acaagctgct gagccgccgc agcaccacac acaccggcac ctactacgac gtccgggagg    24300
tgcccgtgca cccgggctgc ctggccacgc cccgggtgcc gttcgccatc gcggcgaccg    24360
ggccgcgcgg catgcggctg gcggcccgcc acgccgacat gtggatcacc gcggggcggc    24420
ccggcgactt cgacgcccct ccgtacgagg agacccctgcc ggtgatcaag gagcagctgg   24480
cgcgcctcga cgaggcgtgc gagcggaccg ggcgggatcc cgccacccctg cgccggctgc   24540
tgctgaccgg cgccatggtg ggcggcaccc tggactccgt cgaggcgtac cgcgacgccg    24600
ccggccgctt cggcgaactc ggcatcaccg acttcgtcgt ccactggccc cggccctcct    24660
tcccctacca gggcagggtg gaagtgctgg agcagatcgc gcgggacgtg ctgaccgtcc    24720
ggggcgggga gcggccgtga tcgcctacga gatcgtcgac atgttcaccg gcacgccctt    24780
ccagggctgc gcgctcgggg tggtcccgga cgcgaccgca ctcgacgacg acggcatgcg    24840
ggcggtggcc cgcgagatcg gcctcaccga cggcgttc gtcctgccac ccgagtcgcc     24900
cgacgccacc caccgggtac gggtcttcac cccggagcgg gagtcaccgt acggcgggca   24960
ctccgccatc ggcacggcca ccaccctggt gcggctgggc cgtctgcgcg cggggagct    25020
ggtgcaggag tgcgggggcc gcctgatgac cgtgcgcgcc agtgcccgac gggccacgct    25080
cggcgtccgg ggggagcccg tgccacccgg cgcctgggat cccgtgccgt tgctggaggc    25140
gtgcggcctc accgaggacg acctggtcgc cgggccccgc gtgaccgggt tcggaccggc    25200
cttccacgtg ctgccggtcg gacccgaggc ggtcgcccgt gccgcacacg acccggcgca    25260
ccccgtgtgg tccacctgcc cggacgcggt ggtggtcgcc tacgacaggc gcggacacct    25320
ggccgacgtc agggtcttcg cccccggcta cggcatgccg gaggacccgg cgtgcgcctc    25380
cgccgccctg gcactgggcg cctggctcac cggcgcgggc ctggtgccgg cgacggacgg    25440
tacccgcctt taccgggtcc ggcaggggca cgggctgggc cgccccgccc ggctcgactg    25500
cgccgtgacc gtacgcgacg gccgagcggt cgcagccgag gtgaccgggg aggtggcggc    25560
caccgccgcc ggccggatgc acctgccccg cacggcggcc gtcgcgcgct gagccggggc    25620
ccggggccgtg taccaggccg agccgcggaa ggcacccggt ccggtcgacg cacacccaga   25680
gcacacgacg cgaatccctg tatcgcagaa cgaagaggag aggaacccga ctgtgttgtt    25740
ccgtccagag ctgcgcggca cccgggggcgc ggtcgcctcg acccactggc tggcctcggc   25800
cgcgggcttc cgcatgtacg acaagggcgg caacgcgttc gacgcggccg tcgccgccgc   25860
gttcgtcatc caggtcgtgg agccccacct caacgggccc ggggagacg tgcccgtcct    25920
cgtccaccgg gccgggagcg gccgggtcga cgtcgtctgc ggccagggcc ccatgccccg    25980
ggccgcgacc atcgagaggt tcgaacagct cggcctgtcc gtggtccccg gctccggcct    26040
gctgccccgcg tggtgccccg cgccttcgg cgcgtggctg cgggtcctcg ccgagtacg    26100
caccctgcgt ctggaggacg tcctggagcc ggcgatcggc tacgccgaac gcggctatcc    26160
gctgcttccc aaggcggcgg cgatgatcga ggcgctccag gaactcttcc gcgacgagtg    26220
gaccgagtcc gcccgcacgt acctggtggg cggggccgcg ccgcggcccg gtcagcgcat    26280
gaccaacccc gacctggccc ggacctaccg gcgcgtcctc gacgaggcca gggcggcggg    26340
cgccgatcgc gacaagcaga tcgacgcggc cctgcgcgcg ttctacgagg gcttcgtggc    26400
cgaggccatc gacggctatc tcgccaaggc ggaggagatc gatgccaccg ccgccgcca     26460
ccgcggcctg ctgaccggcg ccgacctggc aggctggcgg gcgacggtgg agccctcgct    26520
ctccttcgac caccgcggcc tcaccgtgca caaggcggga ccctggtccc agggcccggt    26580
```

```
cttcctgcaa cagctcgcgc tgctgcggga gttcgacctc gccggtatgg gaccgcacag   26640
cgcggagttc gtgcacaccg tcaccgaggc ggcgaaactg gcgttcgcgg accgcgaggc   26700
ctggtacggc gatcccgcgc acgcggaggt gccggtcggc gacctgctgg acccggccta   26760
caccgcggcc cgccgcgagc tgatcggcag cgaggcgtcc acggagctgc ggccgggctc   26820
accgggaggc cggacaccgg tgctgccgcc cgtccacgac gagtccgccg gtccggccgg   26880
tccctcctgg ctcggcgagc tcgaggaggg catcccggcg gtggtgcgct ccacggccgc   26940
ccggggcgac acctgctgcg tcaccgccac cgacgcccac gggaacatgg tggtcgcgac   27000
gccgagcggc ggctggctga agagttcgcc ggtggtgccc ggtctgggct cccgctcgg    27060 tacccgtggg cagatggcca cgctcacccg ggggcacgcc aacgcgctgg ctcccggcaa   27120
gcgcccccgc accaccctca gcccgaccct ggtgctccgg gagggcaggc ccgccctggc   27180
gttcggcaca ccgggcggcg accagcagga ccagtggacg ctgcagttct tcctgaggca   27240
caccgaacac ggcatggggc ttcaggaggc cgtcgaggca cggaccttcc acaccgacca   27300
cgtcccgacg tccttcaccc cccggcgttt cgctcccggg acggtgaccg tcgaaagcgg   27360
catgccggag gaaaccatcc aggagctcag gcggcgcggc caccaggtcc gcacggtcgc   27420
cgactacagc ctgagcaagg tgtgtgtcac cggcctggcc agcgacgaca tggtcatcgc   27480
ggcggccagt ccgcgcggcg cgcaggcgta cgccgtcgcg gattgaggat gccgaccgga   27540
tgcgataagt ttccaaacgg aaatcgtctc ggcgaatgga aggggaacgc atggtgcccc   27600
acccgtcact ggacccgggt gaccacatcg ttctgggaga agcacggcag aacaacctca   27660
agggcgtcag cctgcgcatc cccaaggdac ggttgaccgt cttcaccggc gtttcgggat   27720
ccggcaagtc ctccctggtc ttcgggacga tcgccgtcga gtcgcagcgg cagatgaacg   27780
agacctaccc cgcgttcatc cgcaaccgcc tccccaagtt cgagcggccc gacgcggagg   27840
tcatcgagaa cctctccacc gccatcgtga tcgaccagcg cccggtcggc ggcaacgcgc   27900
gctccacggt cggcaccatg accgagatcc acgccatgct gcgggtgctg ttctcccggc   27960
acggcaggcc cagcgcgggt ccctcacaca tgtactcctt caacgatccg cgcggcatgt   28020
gcccggagtg cgagggactc ggatccaggg tgcggctgga tttgaaccgc cttctggacg   28080
aggacaagag cctcaacgag ggcgccatcc gcttccagcc cttcgcggtg gcaccttcc    28140 cgtggcagct gtacgcggag tccgggctgt tcgatcccga cctgccgctg cgggagttct   28200
ccgcggacga ccgcgaactg ctgctgcacg gttccgggtt caaggtcgac cgggccggcc   28260
ggcacggcgt ctacaagaac gagtacgagg gcatcgtgct gcgcttcacc cggcgctacc   28320
tcaaggcggg cctcgacacc ctcaagccga aggaacgggc ggcggtgcag gaggtcgtga   28380
cggaggggcc ctgcgaggcc tgcggaggcg cccggctggg accggccgcg ctcgcgtcgc   28440
ggatcgccgg ggagaacatc gccgactact ccgccctgga ggtcaccgat ctgatcggcc   28500
gcctggagcg caacgacgcc ccaccggtca gcggtggt   ccaggcggcg ctggccgcac   28560
tgcgcaggat cgaggccgtc ggactcggct acctcagcct cgaccgccag accgccacgc   28620
tctccggcgg cgaggcgcag cggctgaaga cggtacgcca cctgggcagc agcctgaccg   28680
ggctgacgta catcttcgac gagccgagcg tgggcctgca cccgcgtgac gtgcgccgtc   28740
tgaacgagct gttgctcgcc ctgcgcgaca agggcaacac cgtgctcgtg gtggagcacg   28800
accgggacgt gatcgccatc gccgaccacg tcgtcgacat gggcccgggc gcgggcagcc   28860
agggcggcga ggtggtctac gagggatcgc cgaccgggtt acgggctcg  dacagcccga   28920 ccggacgcgg cctgcgttcg gtgccgggac tgaagcgccg actgcgcgcc cccgacggca   28980
```

```
ggctgacggt ccgcggcgcg cggctgcaca acctcaagga cgtcacggtc gacgtgccca    29040
ccggtgtgct ggtggcgctg agcggtgtcg ccggctcggg caagagctcc ctcgcccggg    29100
agctggcagc gcggcacccg gaggaaacgg tcgtggtcga ccagtcctcc atcgggatct    29160
cctcccgatc caccccgcgc acgtacaccg acatcatgga caccgtccgg cggctgttcg    29220
cccgcgcatc cggaaccgac cccggcctgt tcagcttcaa ctccgcgggc gcctgcccgg    29280
agtgccaggg ccgcggtgtg atcgagaccg acctcgcgtt catggacccg gtcaccaccg    29340
tctgcgagcg ctgcgagggg cgccgcttca cgacgaggc gctgagccac accctgtccg    29400
gccggaacat cgccgacgtc ctcgccatga cggccgagga ggcgatcggg ttcttcgcgg    29460
aggactccgt ccgccgcaaa ctggccctgc tgacggaggt cggcctcggc tacctgacgc    29520
ttggccgctc cctgtccacc ctgtccggcg gcgaacgcca acggctgaag ctggcgcacc    29580
ggctgcacgc ctccggcagc gtctacatct tcgacgaacc gtccaccggc ctgcacatga    29640
cggacgtggg caagctgctc accctgttcg accgcctcgt cgacggcggc aacacggtgg    29700
tggtcatcga acacgacctc gacgtgctca agtacgcgga ctggatcatc gatctcggcc    29760
cggaggccgg ccggcacggc ggccgggtgg tcttcgaggg caccccggcg gacctggcgc    29820
gggtgcggga atcgcacacc ggccggtgtc tggccgagga cctcgccgca cacggtcacc    29880
tctgacggcc cggagcaccg gctgccgcc gggtccgggc cggggtcgca cccgtcctc    29940 ccgcacacct cccgtccgac aaggagtccg tatgcccctc atccacgtca ccctgctgag    30000
cggtcgcggc gaggaggaga tcgccgccct cggccgggcc gtcacggagg ccgtacacac    30060
cacgctgggc acccccggg aggcgatccg ggtgacggtg gacgcatgcc cgcccgagca    30120
ctggttcgtg ggcggcgtct cgatggcgga gaagaaggcg gcccggggcg gctgagcggt    30180
gctccgttcg ccccgggcgc cgcggttcag gccgcgtccg cgaaccgccg gcggatccgc    30240
ccgacgtgct ccgggtccac ggccgggagg tcgtcgcggg tgagccggcc gctgcgcgtc    30300
agcaggtgcg cgttgaaggc ctccggcgcc agccccacgc agcggtcgat gttctcgaac    30360
cactccaggc tggtcagcgc ggtccgctgc atccgctcca cggcgggccg ccgctcggcc    30420
tcgtaggccg ccagagcctc ggggaccgtc ccgtggtcgt gcagggccgt ggcgagggac    30480
agaccgtcct ccatcgccag tttggtaccc gaaccgatcg agaagtgcgt cgtgtgggcg    30540
ctgtcaccga ggagaacgag gttgccgtgg ctccagtcgc ggttgcgtac ggcagcgaag    30600 cgacccagt acgaccggtt gccccacagc ccgtgtccgt ccagcagacc ggtgaagtac    30660
tccctcaccc tcccgatgct ctccggtcg cccaccgggt catcggaccg gcgctccgcg    30720
gcgcggaaac cggccgcccg ccacaccgcg tcaccgatct ccacgatgaa cgtgctgcga    30780
ccgggggcgt acgggtaggc gtgggcctgc accgggccg ggtcggtctc gaccacggcg    30840
aaggtgagcg cgtcgaacgg ccggtccgtg ccgagccaca tgtaacgcga cccggcctgt    30900
tcccgctccg tgccgaacgc ggcctcgtac cgcgcgcggg tgcgcgatcc cacgccgtcc    30960
gcggcgacga cgaggtcgtg ggacgcgcgc aaccgggaca cctcgggcgc cggggagccg    31020
aagtgcagac gcaccccgag gtcggcgcag cgctcctgaa ggagccgcag cagggtgtgg    31080
cggccgatcg cggcgaaccc gtaccctcg ttgcgctgga cccggcccg gtagcagacg    31140 tcgatccgcg tccaccgggc gaactcggcc tcgacagcct cgaacagagc cgggtcggcg    31200
gcctcgatgc cgccgagggc gccgtcggag aagacgacgc cgaacccgaa cgtgtcgtgg    31260
gccgcgttgg cctcccacac ctccacgacg tcgtggggcc gcaggcgctt gaccaggcag    31320
```

```
gccgtgtaca gcccgccggg accggctccg atcaccgcta tccgcatgac acctcgctgg    31380
ggctccgaga gagatggatg gacgtgcaga gaccagtaaa tgctatccga agagaaatga    31440
tctggtggtc aatctccttt ccagctccgc gagttccggg actgaccgga gcagatcgtt    31500
gcccacacgt aatcaagtct gacgaagga tgcccacatg ccggacgtcc tcaccccac      31560 cccgctgccg gcggccgacc tggcgggcct cttccgcgcc ctggaccgc cgccgttcgc     31620 cctggtgcgt cgtgccgcac cggacgggac cagcaccggc ccgttcgacg tgttcatcgg    31680
caccatggac accgtgcgac gggtgacgga cctgccgtcg ggcccggccg tgccgggcgg    31740
gggaccccac acactggccc tactgccgta ccggtgcctg gccgaaagag ggctggactg    31800
ccacgacgac ggcacaccac tgagggtcct gcggatccgc cggcggcaca cggccgacca    31860
cgccgcgctc accgcggccc tcgccgcggt gcggcccgcg ggagacctcc tcggggaagg    31920
cgccggcttc gacggctccg acgaggacta cgccgacctg gtccgcgacc tcatggccga    31980
cgaggtggca cgcaccggtc tgcacgtcct gatccgcagg gacttcaccg cccggttgcc    32040
aggacacgga cccgtggtgg tgggcgaact gttccgccgg ctgctggccg tggagcacgg    32100
cgcgtactgg acgttcgcgg tgtacaccgg aggccccgac ggtgccgcac tggccggagc    32160
ctcaccgcag ggtcacgtca cactgcgaa cggccgggtc gtgatgcgcc cgatgtgcgg    32220
cacgctccgc cttccacccg gtggccggcc gagcgccgcc gacctggtgg ccttcctgcg    32280
tgacggcaag gagtccgaag aactgggggc cgtggtcgac gcggaactcg ccatgctgtg    32340
ccggatcagc gagggggacg tacgcctgga aggaccgcgc ctgcgaccga tggcccgcgt    32400
actgcacacc gagtgccgca tcagcgccac cgccgcgctg ccggccccggc acacgctcgc    32460 cggctccctg ttcgcggcga ccgccgtggg ccgcccttc gcggacgcgt gccgcgtcat     32520
cacccgccgc gaaccaaccg ggcgcggtta ctacggcggc ctgatcgcgc tgctgggcca    32580
cgacgacgcg ggaaacgagg aactggacac cgccgtgctc atccgcacct tcgaggtgtc    32640
cgggcagggc cggctgaagc tgtcggtcgg agccaccctc gggcccgct ccgtggccgc      32700 cgacgagacg gccgagacgc gcgccaaggc ctcggccctg tgtcggcgc tcgcaagcgg    32760 aggaccgact gcggagggcg gtgccgggcg ccacgcgcgg gctggtcttg gtcgcggccc    32820
ggaggcggcc ggcggcccgg ccaccggtga gcgaagcgga gtgccgggtg accggacgcg    32880
gcaccagcag gccgccggcc ggcagcccac gtccccgcc gacccggcgt ggcgccgtc      32940 ggtgaccgcg gagggcggtg ccggggacca cgcgcgggct ggtcttggtc gcggcccgga    33000
ggcggccggc ggcccggcca ccggtgaggg aggcggagtg ccgggtgacc ggacgcggca    33060
ccagcaggcc gccggccggc agcccacgtc cccgccgac ccggcgtggc gccgtcggt      33120 gaccgcggag ggcggtgccg ggggccacgc gcgggctggt cttggtcgcg gcccggaggc    33180
ggccggcggc ccggccaccg gtgagggagg cggagtgccg ggtgaccgga cgcggcacca    33240
gcaggccgcc ggccggcggc ccacgtcctc cgccgacccg cgtggtgcc cgtcggtgac     33300 cgcggaactg gaccggcgcc gcgcacgtct gtccgcctac tggcaacgcc ccgtcggcc     33360 gggcagccgg cccgctccgc ggccaccggt gctgctcgtc gacacgggtg gcgaggagac    33420
ggcgccgctg gccgccatgc tgcgcggact gggccgcacc gtcgacgtgc gtcccgcgta    33480
ccccgcggcg gccgcgccac ggaccgtcgc gcccggaacc acggtcgtcc tcggccccgg    33540 ccgggtgac ccgttggccc acggcgacga ccgcatcacc gcgctgcggg ccatgacgtc     33600
cgccctcctg tccagcggag cacccacgtt cggggtcggg ctcggcttcc acctcctgct    33660
cgccgtgctg ggtctggccg gggccgcgcg agcgtgggac ggggccaccg gccagcggga    33720
```

```
gatcgaggtc ttcggcagac gcgcgacggt ggggtacggt ggcacgcaca ccgtggtggc   33780
cggcccgcac acggacaccc tcgcgcggcg gctgtccctg acgctctgct acggcccggc   33840
ccacggcgag ctggtggcca tgcgaggccc tcgaaccggc ggcgtcgcct tcctcccggc   33900
atcggtgctg agcgtcgagg gggcggagct gctggatctc ctgctgccct gagcgagcgg   33960
gtgacgggcc gggccccggc cgctcacccg ttcgccgtgc ccccgagctc gagcacggtc   34020
cgcgcggccg actccagcgc gagtgtcatc gagccgccgt tgggctcgaa cgaggtgtgg   34080
tcaccggcga agtggatccg gccctccggc cggcgcatgg ccggcatcag ggaactgtgc   34140
cccatctcgg gaaggatgta ggcgccttcg atgtacggct gctggtccca gaccaccgag   34200
gtgccggtct cgaagtgctc gcgggcaccg ggcagcatcg actcgacgtg ttccagggcg   34260
aagcggatcc gctcctcggg gctcagcacg gcaagcgccc gggcccgcca gccggttatc   34320
aggcactcca gtatcttgcg gggcccgggc aaccggggag tggcgtcccg gacccaccgc   34380
accggcaggt ccgtggagaa actcgcgttg tcctgggccc agaaccgccg gcgcatctgg   34440
aggtagacgc gcacgatcga cgagtacttc acccggcgca tcacggcctg tttggcgtcg   34500
gacagcccgg cgtccgtgaa gtcgatgtgc cggatcgcgc tgaacggcac cgtcaccacc   34560
acgcggtccg cgtccacgga gcgcatgcgg gtgccgtcca ggaaggtgac acgagcgccc   34620
tcgtcgtcct gggcgacccg caccaccgga gcgcggtagc ggatgcggtc cttcagccgc   34680
tcggcgaacg cccgggggaa gcggtcggtt ccgcccttca ccttcgacca ccgggggtcg   34740
gcgttggcca gcgagtgcgg gctggactcg tgccgcagcc aggacagggc ggaggccgtc   34800
ttgaggtccc cgccgcgcat ctccaggaag tgcggttcca ccaggtcgat cgccgccggc   34860
gaagcgcccc gcccggacag cacctcgtac accgagcgcc ggtcgtacgg ttcgagcagg   34920
ggggtcggcg cccagtccgc agccgtgatg tcgggttcca gcgcctcgta ggcgcggcgc   34980
acatagcggt cgatcatgtc ggtgacgctc agcccttct cgtgcggggc gagcgggagc   35040
ccggcgcggt ccagcgagtc ggcgtcggga ccgaagaacc ggttgccgac gaagtacgag   35100
aactggctgc cgaccaggtc ggccgtctcc agttccaccc ccagttcgcg caggtagtgc   35160
atggcgtagt ggcagtgcgg ggtcagcgtc atcgcgccgg cctcggcgta cagaccgtcc   35220
gtgaacggct cgcgcagtgt gtacgcacgc ccgcccggac ggttcgacgc ctccaggacc   35280
gtcacgtcag tgccgcgccg ggccagttcg taggccacgg cgaggcccga caggcccgca   35340
cctatgacga cgaccctgcc gggcacccgg agtcccggca ttcccctgtc gaactcgcga   35400
cgcacgtcgg tctgcgtgac ctcggccatc ggctctccct cccccgtgac tgtgcacggt   35460
tgccgttcat atgattgacg tcaggaaatc atattcggat gctctcaacg gtaaagcctt   35520
gcatctcagg tgtgttgagc cccgcccga cttggtagct gctgaccagc aatcgttgcc   35580
ctcgtcggag ccgtttcctt cgcacccggc cgtcgttcgg cagggcatgg acaccgcacc   35640
gatcctcgtc ctcggagcca ccggctccac gggccggcgt gtcaccgcac acctgcgggc   35700
tctgggagcg ccggtcagag gcgcctcccg gcacagcgcc atccgattcg actggaacga   35760
ccgcagtacg tgggaaccgg ccctgcgggg cgcgaaccgc atgttcctga tggcccccga   35820
cggcatcccc gtccacccgg acctcgtcgg cctggccgcg gacctcggcg tcgaacgcat   35880
cgtcctgctg tccagccgcg ccatcgaggt gataggagac cagaggctga tcgcggccga   35940
ggacaccgtc aagaagtccg gagccgcctg gacgatcctg cgcatcgact ggttcgacca   36000
gaacttcgac gagggcccct tccgcgacgc ggtccgcgcg ggtgagctgg cgctgccgct   36060
```

```
ggggattgc cgacaggggt tcgtggacct ggacgacgtg ggggccgctg ccgcccggac   36120
tctgaccgag gacggacaca ccggccggac gtacgaactg accgggccgc aggcgctctc   36180
cttcggcgag gcgtgcgccg tcatccagga cgtcaccggc cgcccgatga ggttccacgg   36240
cggcgacgac gcctaccgcg ccgcgcagac gtccttcggc cgctccgagg agtccgtcga   36300
acgcgacatc accgcctacg cggcactccg ctccctcggc gacaccgagc tctggacac    36360 cgtgccccgc ctgaccgggc gccgggcccg cacgttccgg gagtacgtca ccgaggccgc   36420
gtccgggaac gactggcccc gccccctgaca ggctcacggt gggcaccggc atgccccgg   36480 ctgtcgggac gggggggcgag ccgcggtcgt cagcggacgc cggtgccgga ccgcggggag  36540
acgagccccg tctcgtaggc gaggatcacc gcctggatcc ggtctctcag cgccagcttc   36600
ccgaggacgt tcgccacatg cgtcttgacg gtcgtttcgg cgaccgagaa ctcggcggcg   36660
atctcggcgt tggacagtcc acgggccatc gcgtggaggg tgtccctctc acgggcggtg   36720
agggccctca ggcccgctgg cggctgcggg ggcgccacct cgagtgcggc gaatcggtcg   36780
agaaggcgtc gggtgacgcg ggggcgatg acggcgtcgc ccgccgcgac cgtgcggatg    36840
gcgtcgacga gggactcggc cgggccgtcc ttgacgagga agccgctggc gcctgctcgg   36900
agggcgtcga gtacgtgctc gtccaggtcg aaggtggtca ggatgatgac gcgggtgtcg    36960
gaggtggagt cgaggagctg tcgcgtggcg tcgatgccgt tcgtgcccgg catgcggatg   37020
tccatgagga cgacgtcggg ctgcaggggct cgggcgtctc ggaccgcggc ccggccgtcc   37080
gccgactccc cgacgacggt gaggcccggc tccgcctcca ggatgtagcg gaagccggtt    37140
cggatc                                                              37146
```

<210> SEQ ID NO 4
<211> LENGTH: 192
<212> TYPE: PRT
<213> ORGANISM: Streptomyces species FH6421

<400> SEQUENCE: 4

```
Leu Leu Glu Ala Ala Gln Leu Phe Ala Glu Gln Gly Tyr Ala Ala
1               5                   10                  15

Thr Ser Val Asn Asp Met Ser Ala Arg Ser Gly Arg Thr Ser Gly Ala
                20                  25                  30

Val Tyr Phe His Tyr Ala Gly Lys Glu Ala Val Ala Val Ala Val Val
            35                  40                  45

Gln Asp Arg Phe Ala Thr Trp Pro Gln Leu Ala Ala Arg Tyr Ala Asp
        50                  55                  60

Glu Ala Val Pro Pro Val Asp Arg Leu Val Ala Leu Ser Tyr Asp Ile
65                  70                  75                  80

Ala His Ala Leu Ala Glu Asp Pro Val Thr Arg Ala Gly Ala Arg Leu
                85                  90                  95

Trp Ala Glu Arg Ala Thr Ile Asn Val Pro Leu Pro His Pro Phe Ala
                100                 105                 110

Leu Trp Thr Thr Ala Ala Thr Arg Leu Leu Ala Lys Ala Arg Leu Ala
            115                 120                 125

Gly His Leu His Pro His Val Arg Pro Ala Arg Ala Ala Arg Thr Leu
        130                 135                 140

Val Pro Ala Phe Phe Gly Leu Cys Ala Leu Thr Glu Glu Leu Glu Gly
145                 150                 155                 160

Thr Ala Ala Leu Thr Asp Arg Leu Thr Asp Trp Trp Gln Leu Thr Leu
                165                 170                 175
```

```
Pro Cys Leu Arg Pro His Pro Val Glu Asp Leu Pro Arg Gly Arg
            180                 185                 190
```

```
<210> SEQ ID NO 5
<211> LENGTH: 162
<212> TYPE: PRT
<213> ORGANISM: Streptomyces species FH6421

<400> SEQUENCE: 5
```

```
Leu Met Thr Arg Thr Asp Ser Pro Arg Ser Ala Ser Glu Thr Ser Ala
1               5                   10                  15

Val Pro Gly Glu Leu Glu Asp Ala Leu Ser His Leu Gln Cys Ile Leu
            20                  25                  30

Val Ala Arg Arg Thr Arg Ser Asn Pro Glu Gly Val Thr Trp Gln Gln
        35                  40                  45

Tyr Asp Val Leu Glu Leu Leu Arg Ile Arg Gly Pro Met Thr Pro Ser
    50                  55                  60

Val Leu Ser Ala Ser Leu Gly Val Ser Arg Ala Thr Thr Ser Lys Ala
65                  70                  75                  80

Leu Arg Val Leu Lys Asp Leu Glu Leu Val Asp Gln Arg Thr Leu Gly
                85                  90                  95

Glu Asp Arg Arg Glu Leu Thr Thr Ser Leu Thr Pro Ala Gly Glu Ala
            100                 105                 110

Phe Leu Thr Arg Val Ala Glu Gln Arg Arg Glu Asn Ala Arg Ile Val
        115                 120                 125

Glu Ala Ala Leu Ser Pro Gly Glu Arg Ala Met Phe Val Glu Leu Cys
    130                 135                 140

His Lys Val Ala Gly Ala Leu Glu Pro His Leu Glu Pro Val Glu Ala
145                 150                 155                 160

Arg Pro
```

```
<210> SEQ ID NO 6
<211> LENGTH: 610
<212> TYPE: PRT
<213> ORGANISM: Streptomyces species FH6421

<400> SEQUENCE: 6
```

```
Val Leu Thr Glu Asn Ala Ser Gly Glu Ala Arg Ser Ala Val Pro Leu
1               5                   10                  15

Thr Leu Thr Glu Gly Phe Asp Arg Val Val Arg Ala Ala Gly His Gln
            20                  25                  30

Val Ala Leu Val Ser Gly Thr Glu Thr Val Thr Tyr Arg Gln Leu Asn
        35                  40                  45

Glu Arg Ala Glu Arg Val Ala Arg Gly Leu Gly Ala Arg Lys Val Ala
    50                  55                  60

Pro Gly Asp Arg Val Gly Val Tyr Leu Arg Arg Ser Pro Asp Leu Tyr
65                  70                  75                  80

Ala Val Met Leu Gly Val Leu Lys Ala Gly Ala Cys Val Val Pro Val
                85                  90                  95

Asn Pro Asp His Pro Ala Pro Phe Val Ser Arg Val Val Ala Glu Ser
            100                 105                 110

Ala Pro Arg Ala Val Val His Asp Ala Gly Thr Pro Ala Val Ala Pro
        115                 120                 125

Ala Ala Pro Gly Ala Pro Leu Trp Val Pro Val Glu Glu Leu Thr Thr
    130                 135                 140

Ala Ala Glu Pro Asp Asp Gly Val Ala Leu Pro Ala Val Asn Asp Pro
```

```
            145                 150                 155                 160
Asp Ser Thr Ala Phe Leu Met Phe Thr Ser Gly Ser Thr Gly Arg Pro
                    165                 170                 175
Lys Gly Val Arg Ile Ala His Arg Gly Leu Ala Arg Leu Gly Pro Tyr
                    180                 185                 190
Ser Gly Glu Leu Arg Met Gly Pro Gln Asp Cys Leu Val Gln Ser Ala
                    195                 200                 205
Ala Phe Ser Phe Ala Ala Ser Thr Ile Glu Ile Trp Leu Ala Leu Leu
    210                 215                 220
His Gly Ala Arg Leu Val Val Met Pro Gln Gly Leu Pro Ser Leu Pro
225                 230                 235                 240
Ala Leu Lys Asp Ala Val Val Arg His Gly Val Thr Ala Leu Ser Leu
                    245                 250                 255
Pro Cys Gly Leu Phe Asn Leu Leu Val Asp Glu Glu Pro Glu Cys Leu
                    260                 265                 270
Arg Gly Leu Arg Val Ile Leu Leu Ser Gly Asp Phe Pro Ser Pro Glu
                    275                 280                 285
His Leu Ser Arg Ala Ala Arg Ala Thr Arg Ala Val Ile Tyr Asn Gly
    290                 295                 300
Tyr Gly Cys Thr Glu Asn Ser Ser Ile Thr Ala Leu Tyr Pro Ile Arg
305                 310                 315                 320
Asp Ala Gly Asp Val Thr Arg Glu Asn Arg Val Pro Val Gly Arg Pro
                    325                 330                 335
Leu Pro Gly Val Thr Leu Glu Val Leu Asp Asp Ser Leu Arg Pro Cys
                    340                 345                 350
Pro Pro Gly Thr Pro Gly Gln Leu Val Val Gly Gly Leu Gly Leu Ala
                    355                 360                 365
Gln Gly Tyr Leu Asn Asp Pro Glu Leu Thr Asn Arg Lys Phe Val Thr
    370                 375                 380
Gly Pro Asp Gly Arg Pro Arg Tyr Leu Thr Gly Asp Leu Ala Arg Ala
385                 390                 395                 400
Thr Glu Asp Gly Asp Ile Val Leu Ile Gly Arg Ala Asp Ser Met Val
                    405                 410                 415
Lys Ile Arg Gly Tyr Arg Val Glu Leu Thr Ala Val Thr Leu Ala Leu
                    420                 425                 430
Arg Ala Leu Asp Gly Ile Gly Asp Ala Val Val Lys Ala Phe Pro Glu
                    435                 440                 445
Gly Ala Gly Glu Lys Ser Leu Thr Ala Phe Tyr Thr Thr Val Asp Gly
    450                 455                 460
Arg Pro Leu Asp Gly Ala Asp Leu Ala Arg Arg Met Gly Asp Gln Leu
465                 470                 475                 480
Pro Ser Tyr Met Val Pro Ser Thr Phe His His Leu Gly Asp Leu Pro
                    485                 490                 495
Arg Asn Ala Asn Gly Lys Ile Asp Arg Ser Ala Leu Thr Asp Pro Ser
                    500                 505                 510
Asp Thr Asn Arg Asp Pro Lys Lys Gly His Thr Ala Val Gln Asn Pro
                    515                 520                 525
Leu Glu Thr Val Val Leu Gln Ala Trp Lys Asp Ile Ser Gly Ala Asp
    530                 535                 540
Asp Phe Thr Thr Thr Asp Ser Phe Leu Gly His Gly Gly Asn Ser Leu
545                 550                 555                 560
His Phe Val Gln Leu Ala Ser Arg Leu Gln Lys Ile Phe Gly Val Glu
                    565                 570                 575
```

-continued

Val Ser Thr Glu Asp Val Phe Arg His Gly Thr Val Glu Gln Leu Ala
        580             585             590

Arg Phe Val Glu Gln Ser Arg Asp Thr Gly Arg Asn Pro Ala Ala Gln
        595             600             605

Thr Gln
   610

<210> SEQ ID NO 7
<211> LENGTH: 1535
<212> TYPE: PRT
<213> ORGANISM: Streptomyces species FH6421

<400> SEQUENCE: 7

Val Asn Ser Pro Leu Arg Thr Thr Val Leu Asp Leu Ala Arg Thr Thr
1               5                   10                  15

Leu Gly Ser Ala Asp Leu Thr Ala His Glu Pro Leu Ala Asp Arg Cys
            20                  25                  30

Glu His Pro Ala Leu Leu Asp Asp Leu Ala Thr Thr Leu Thr Ala Val
        35                  40                  45

Phe Ala Val Glu Ile Thr Gly Ala Asp Leu Ala Ala Gly Ala Thr Val
50                  55                  60

Ala Asp Val Ala Ala Arg Met Asp Asp Arg Arg Asp Ala Pro Arg Ile
65                  70                  75                  80

Pro Glu Leu Arg Ala Gly Leu Ala Pro Arg Asp Gly Arg Ala Val Glu
                85                  90                  95

Ala Ser Phe Gly Gln Ser Gly Ile Trp Leu Ile Asp Gln Tyr Leu Pro
            100                 105                 110

Asn Pro Ala Ala Tyr Asn Gly Pro Phe Phe Val Arg Leu Pro Phe Ser
        115                 120                 125

Ala Asp Pro Asp Arg Leu His Ala Ala Val Arg Gly Val Leu Arg Arg
130                 135                 140

Gln Glu Val Leu Arg Thr Thr Tyr Ala Leu Ser Asp Gly Thr Leu Arg
145                 150                 155                 160

Gln Asn Val Ser Arg Asp Asp Ala Val Val Phe Glu Val Ala Arg
                165                 170                 175

Tyr Gly Asp Asp Lys Glu Leu Asp Ala Leu Val His Arg Val Ala Asn
            180                 185                 190

Leu Arg Leu Asp Leu Ala Arg Gly Pro Val Ile Ala Val Thr Cys Ala
        195                 200                 205

Leu Gly Pro Ala Asn Arg Ser Ala Val Ile Cys Asn Ile His His Ile
    210                 215                 220

Ala Ser Asp Ala Ala Ser Ala Gly Val Phe Leu Arg Glu Leu Leu Asp
225                 230                 235                 240

Ala Tyr Asp Arg Leu Gly Arg Gly Leu Pro Val Glu Ala Asp Pro Leu
                245                 250                 255

Arg Pro Thr Tyr Gly Asp Phe Ser Gln Trp Tyr Arg Glu Leu Met Asn
            260                 265                 270

Pro Glu Ala Leu Thr Arg Ser Leu Asp His Phe Ala Ala Arg Leu Ala
        275                 280                 285

Gly Glu Leu Pro Val Leu Asp Leu Pro Thr Asp Arg Pro Arg Pro Pro
    290                 295                 300

Val Lys Gln His Arg Gly Gly Thr Leu Pro Leu His Leu Pro Ala Ala
305                 310                 315                 320

Ala Ala Asp Asp Phe Glu Ala Leu Ala Arg Thr Glu Gly Val Thr Leu

```
                        325                 330                 335
    Phe Met Ala Leu Val Ala Ala Tyr Ala Val Phe Leu Ser Arg His Thr
                        340                 345                 350
    Gly Gln Arg Arg Val Leu Ile Gly Ser Pro Val Ser Leu Arg Asp Asp
                        355                 360                 365
    Pro Ala Thr His Glu Leu Ile Gly Tyr Phe Val Asn Leu Val Val Leu
                        370                 375                 380
    Gln Gln Glu Ile Asp Asp Arg Met Thr Val Arg Asp Val Leu Arg Arg
385                 390                 395                 400
    Ala Arg Glu Glu Val Ser Glu Ala Leu Arg His Lys Trp Ala Pro Phe
                        405                 410                 415
    Asp Lys Val Val Glu Arg Leu Gln Pro Pro Arg Ser Ser Gly Tyr Thr
                        420                 425                 430
    Pro Leu Val Gln Thr Met Leu Val Leu Thr Gln Gly Asp Ala Gly Arg
                        435                 440                 445
    Ile Ser His Asp Asp Thr Glu Leu Arg Ile Glu Arg Gly Ala Ala His
                        450                 455                 460
    Gly Ala Lys Tyr Asp Leu Ser Leu Val Phe Glu Arg Asp Ser Glu Gly
465                 470                 475                 480
    Leu His Gly Leu Ile Glu Tyr Asp Ala Asp Leu Phe Asp Glu Pro Thr
                        485                 490                 495
    Val Arg Ala Met Gly Asp Arg Leu Arg His Leu Met Glu Gln Phe Ala
                        500                 505                 510
    Arg Arg Pro Asp Ala Pro Leu His Glu Leu Glu Ala Leu Gly Ala Gln
                        515                 520                 525
    Glu Arg Arg Ser Val Leu Val Arg Gly Asp Arg Thr Ala His Ala Val
                        530                 535                 540
    His Asp Ala Pro Val Met Glu Leu Phe Glu Ala Gln Ala Arg Ala Thr
545                 550                 555                 560
    Pro Asp Ala Val Ala Leu Glu Asp Gly Asp Thr Thr Leu Ser Tyr Arg
                        565                 570                 575
    Glu Leu Asp Glu Arg Ala Asn Arg Leu Ala His Val Leu Arg Ala Ser
                        580                 585                 590
    Gly Ala Ala Ala Gly Thr Arg Val Gly Ile Cys Leu Pro Arg Ser His
                        595                 600                 605
    Asp Met Val Val Ala Leu Phe Ala Ile Leu Lys Thr Gly Ala Ala Tyr
                        610                 615                 620
    Val Pro Leu Asp Pro Ser Tyr Pro Arg Gln Arg Ile Thr His Thr Leu
625                 630                 635                 640
    Arg Asp Ala Gly Val Phe Leu Thr Val Thr Asp Ser Ser Leu Ala Asp
                        645                 650                 655
    Glu Leu Pro Pro Arg Glu Pro Leu Phe Val Leu Asp Arg His Asp Gly
                        660                 665                 670
    Pro Ile Ala Ala Ala Pro Ala Thr Gly Leu Gly Arg Val Lys Thr Pro
                        675                 680                 685
    Asp Asp Glu Ile Tyr Val Val His Thr Ser Gly Ser Thr Gly Leu Pro
                        690                 695                 700
    Lys Gly Val Val Ile Ala Asp Arg Thr Val Ala Asn Leu Val Arg Ala
705                 710                 715                 720
    Gln His Arg Cys Ser Pro Ala Gly Ala Thr Gly Arg Thr Leu Gln Tyr
                        725                 730                 735
    Met Ser Leu Ser Phe Asp Val Ser Val Met Glu Ile Leu Gly Thr Leu
                        740                 745                 750
```

```
Cys Val Gly Gly Thr Leu Val Leu Val Ser Glu Glu Leu Arg Lys Asp
            755                 760                 765

Leu His Ala Leu Ala Gly Phe Leu Ala Glu Arg Arg Val Thr Arg Val
    770                 775                 780

Tyr Leu Pro Tyr Ile Ala Leu Gln Gln Leu Ala Ser Leu Ala Thr Asp
785                 790                 795                 800

Ala Gly Val Arg Leu Asp Asp Leu Arg Glu Ile Thr Ser Val Gly Glu
                805                 810                 815

Ala Leu Val Val Ser Pro Gln Ile Arg Glu Phe Ala Thr Arg His Pro
                820                 825                 830

Ala Val Arg Leu Val Asn Met Tyr Gly Pro Ser Glu Thr His Leu Ala
                835                 840                 845

Ser Trp Tyr Pro Leu Thr Gly Ser Pro Ala Thr Trp Pro Asp Arg Pro
850                 855                 860

Pro Ile Gly Arg Pro Val Asp Gly Val Arg Leu Val Val Leu Asp Ala
865                 870                 875                 880

His Met Arg Leu Val Pro Pro Gly Val Pro Gly Glu Leu Tyr Ile Gly
                885                 890                 895

Gly Pro Val Leu Ser Pro Gly Tyr Arg Asn Arg Pro Asp Glu Thr Ala
                900                 905                 910

Arg Arg Phe Leu Pro Asp Pro Phe Gly Gly Pro Ala Asp Arg Leu Tyr
                915                 920                 925

Arg Thr Gly Asp Leu Val Arg Trp Asn Ser Glu Gly Asp Leu Glu Tyr
                930                 935                 940

Leu Gly Arg Thr Asp Asp Gln Ile Lys Ile Arg Gly Tyr Arg Ile Glu
945                 950                 955                 960

Pro Ala Glu Ile Glu Ala Ala Leu Asp Asp Leu Asp Gly Val Ala Ser
                965                 970                 975

Ser Ala Val Ala Ala Val Asp Val Ala Pro Gly Asp Arg Arg Leu Val
                980                 985                 990

Ala Val Leu Glu Thr Ser Arg Thr Trp Glu Thr Ala Glu Leu Arg Arg
                995                 1000                1005

Ala Leu Ser Gly Thr Leu Pro Asp Tyr Met Val Pro Ala Leu Val
    1010                1015                1020

Val Ala Val Glu His Met Pro Thr Thr Pro Ser Gly Lys Ile Asp
    1025                1030                1035

Arg Arg Ala Val Ala Gly Leu Ala Ala Ala Gln Ala Thr Ala Ala
    1040                1045                1050

Arg Thr Ala Pro Ala Pro Pro Gly Arg Pro Arg Pro Gly Leu
    1055                1060                1065

Glu Gln Arg Ile Ala Arg Glu Trp Ala Asp Val Leu Lys Val Pro
    1070                1075                1080

Ala Val Gly Arg Asp Glu Asp Phe Phe Ser Val Gly Gly Asn Ser
    1085                1090                1095

Ile Ile Ala Thr Glu Leu Val Tyr Arg Leu Arg Arg Ala Phe Asp
    1100                1105                1110

Gln Asp Leu Ser Leu Arg Ala Leu Leu Glu Asn Pro Thr Val Ala
    1115                1120                1125

Gly Met Ala Ala Arg Leu Arg Ser Gly Pro Gly Ala Pro Thr Thr
    1130                1135                1140

Ala Pro Ala Ala Leu Arg Glu Asp Ala Thr Leu Pro Asp Asp Leu
    1145                1150                1155
```

-continued

```
Pro Ala Val Thr Gly Thr Pro Val Pro Val Ala Arg Ala Arg Glu
    1160            1165            1170

Val Leu Leu Thr Gly Ala Thr Gly Phe Leu Gly Ser Tyr Leu Leu
    1175            1180            1185

Arg Glu Leu Thr Gly Thr Thr Gly Gly Arg Val His Cys Leu Val
    1190            1195            1200

Arg Ala Ala Asp Glu Arg Ala Gly Met Glu Arg Leu Arg Ala Thr
    1205            1210            1215

Ala Glu Arg Tyr Arg Leu Asp Gly Arg Ile Asp Trp Asn Arg Val
    1220            1225            1230

Arg Ala Val Pro Gly Asp Leu Ser Arg Pro Gly Phe Gly Leu Pro
    1235            1240            1245

Gly Ala Glu Tyr Asp Ala Leu Ala Gly Thr Val Asp Val Val Tyr
    1250            1255            1260

His Ala Ala Ala His Ile Asn Phe Val Leu Pro Tyr Ala Ser Val
    1265            1270            1275

Lys Pro Thr Asn Val Asp Gly Phe Arg His Val Val Arg Phe Ala
    1280            1285            1290

Ala Thr Asp Arg Pro Lys His Val Gln Tyr Met Ser Thr Ile Ala
    1295            1300            1305

Val Phe Pro Pro Gly Glu Ala Pro Asp Gly Thr Val Leu Thr Glu
    1310            1315            1320

Asp Asp Val Pro Glu Ala Cys Glu Arg Leu Gly Ile Gly Tyr Thr
    1325            1330            1335

Gln Ser Lys Trp Val Ala Glu Arg Ile Ala Leu Ala Ala Arg Ala
    1340            1345            1350

His Gly Val Pro Val Thr Ile His Arg Ile Gly Arg Ile Ser Gly
    1355            1360            1365

Asp Ser Val Thr Gly Ala Cys Gln Ser Asp Asp Phe Leu Trp Arg
    1370            1375            1380

Gln Ile Lys Ser Phe Ile Glu Leu Gly Ser Ala Pro Pro Ala Glu
    1385            1390            1395

Asp Leu Thr Thr Asp Leu Leu Pro Val Asp Phe Val Ala Arg Ala
    1400            1405            1410

Val Val Ala Leu Ser Arg His Pro Ala Thr His Asn Arg Thr Leu
    1415            1420            1425

His Val Phe His Pro Ser Gly Ser Asp Phe Thr Pro Val His Ala
    1430            1435            1440

Ala Leu Arg Ala Asp Gly His Arg Leu Glu Ile Val Pro Ala Asp
    1445            1450            1455

Thr Trp Leu Ala Arg Leu Glu Glu Ser Ala Arg Arg Pro Gly Gly
    1460            1465            1470

Asn Ala Leu Ala Ala Ala Val Pro Leu Phe Arg Glu Gly Ala Leu
    1475            1480            1485

Glu Leu Gly Asp Asn Thr Tyr Gly Asn Thr Ala Thr Thr Arg Leu
    1490            1495            1500

Leu Met Asp Leu Gly Leu Pro Trp Pro Ala Ile Asp Glu Gln Ala
    1505            1510            1515

Ile Thr Arg Met Leu Arg Tyr Phe Arg Ser Val Gly Glu Leu Ala
    1520            1525            1530

Asp Asp
    1535
```

-continued

```
<210> SEQ ID NO 8
<211> LENGTH: 406
<212> TYPE: PRT
<213> ORGANISM: Streptomyces species FH6421

<400> SEQUENCE: 8
```

| | | | | | | | | | | | | | | |
|---|---|---|---|---|---|---|---|---|---|---|---|---|---|---|
| Met | Pro | Thr | Ser | Ser | Cys | Pro | Asp | Thr | Ala | Tyr | Asp | Thr | Leu | Ile | Pro |
| 1 | | | | 5 | | | | | 10 | | | | | 15 | |
| Ser | Val | Val | Ala | Ala | Leu | Pro | Ala | Ala | Gln | Gln | Pro | Glu | Trp | Pro | Asp |
| | | | 20 | | | | | 25 | | | | | 30 | | |
| Pro | Gly | Arg | Leu | Ala | Leu | Val | His | Thr | Glu | Leu | Ala | Arg | Ala | Asp | Pro |
| | | 35 | | | | | 40 | | | | | 45 | | | |
| Leu | Val | Thr | Tyr | Asp | Ser | Val | Arg | Ala | Leu | Arg | Arg | Leu | Leu | Ser | Arg |
| 50 | | | | | 55 | | | | | 60 | | | | | |
| Ala | Ala | Glu | Gly | Glu | Leu | Cys | Val | Leu | Gln | Ala | Gly | Asp | Cys | Ala | Glu |
| 65 | | | | | 70 | | | | | 75 | | | | | 80 |
| Asp | Pro | Ala | Glu | Cys | Gly | Pro | Ala | Pro | Leu | Ala | Arg | Lys | Ala | Glu | Met |
| | | | | 85 | | | | | 90 | | | | | 95 | |
| Leu | Asp | Val | Leu | Ser | Asp | Ile | Val | Arg | Thr | Gly | Ala | Gly | Arg | Pro | Val |
| | | | 100 | | | | | 105 | | | | | 110 | | |
| Val | Arg | Val | Gly | Arg | Val | Ala | Gly | Gln | Tyr | Ala | Lys | Pro | Arg | Ser | His |
| | | 115 | | | | | 120 | | | | | 125 | | | |
| Pro | Glu | Glu | Leu | His | Asp | Gly | Val | Arg | Leu | Pro | Val | Tyr | Arg | Gly | Pro |
| | 130 | | | | | 135 | | | | | 140 | | | | |
| Met | Val | Asn | Ala | Pro | His | Pro | Asp | Ala | Asp | Ala | Arg | Arg | Pro | Asp | Pro |
| 145 | | | | | 150 | | | | | 155 | | | | | 160 |
| Ala | Arg | Ile | Leu | Ser | Cys | Tyr | Arg | Ala | Ala | Arg | Arg | Ala | Val | Glu | Ser |
| | | | | 165 | | | | | 170 | | | | | 175 | |
| Leu | Asp | Arg | Leu | Gly | Arg | Gly | Glu | Gly | Ser | Pro | Ala | Glu | Thr | Arg | Val |
| | | | 180 | | | | | 185 | | | | | 190 | | |
| Trp | Thr | Ser | His | Glu | Ala | Leu | Leu | Leu | Asp | Tyr | Glu | Leu | Pro | Leu | Val |
| | | 195 | | | | | 200 | | | | | 205 | | | |
| Arg | Arg | His | Arg | Ser | Gly | Arg | Ser | Tyr | Leu | Ala | Ser | Thr | His | Trp | Pro |
| | 210 | | | | | 215 | | | | | 220 | | | | |
| Trp | Val | Gly | Glu | Arg | Thr | Arg | Gln | Pro | Asp | Gly | Ala | His | Val | Arg | Leu |
| 225 | | | | | 230 | | | | | 235 | | | | | 240 |
| Leu | Ala | Glu | Val | Asp | Asn | Pro | Val | Ala | Cys | Lys | Val | Gly | Pro | Thr | Thr |
| | | | | 245 | | | | | 250 | | | | | 255 | |
| Thr | Val | Glu | Gln | Val | Leu | Ala | Leu | Cys | Thr | Ala | Leu | Asp | Pro | Glu | Arg |
| | | | 260 | | | | | 265 | | | | | 270 | | |
| Ser | Pro | Gly | Arg | Leu | Ser | Leu | Val | Ala | Arg | Phe | Gly | Ala | Ser | Arg | Ile |
| | | 275 | | | | | 280 | | | | | 285 | | | |
| Asp | Gly | Leu | Ala | Pro | Leu | Val | Arg | Ala | Val | Arg | Arg | Ala | Gly | His | Pro |
| | 290 | | | | | 295 | | | | | 300 | | | | |
| Val | Leu | Trp | Leu | Cys | Asp | Pro | Met | His | Gly | Asn | Gly | Glu | Arg | Thr | Ala |
| 305 | | | | | 310 | | | | | 315 | | | | | 320 |
| His | Gly | Leu | Lys | Thr | Arg | Arg | Leu | Ser | Ala | Val | Met | Ala | Glu | Ile | Ser |
| | | | | 325 | | | | | 330 | | | | | 335 | |
| Arg | Phe | Val | Asp | Ile | Val | Ser | Ala | Glu | Gly | Gly | Arg | Ser | Ala | Gly | Leu |
| | | | 340 | | | | | 345 | | | | | 350 | | |
| His | Leu | Glu | Ala | Ser | Pro | Asp | Asp | Ile | Ala | Glu | Cys | Thr | Gly | Ala | Gly |
| | | | 355 | | | | | 360 | | | | | 365 | | |
| Phe | Thr | Pro | Ala | Pro | Gly | Pro | Ala | Tyr | Arg | Thr | Leu | Cys | Asp | Pro | Arg |
| | | 370 | | | | | 375 | | | | | 380 | | | |

Leu Asn Leu Val Gln Ala Val Ala Thr Ala Tyr Trp Arg Leu Pro
385                 390                 395                 400

Ala Leu Glu Ala Val Ala
                405

<210> SEQ ID NO 9
<211> LENGTH: 660
<212> TYPE: PRT
<213> ORGANISM: Streptomyces species FH6421

<400> SEQUENCE: 9

Met Ser Glu Ser Ala Arg Asn Ala Arg Gly Leu Ala Ala Leu Leu Pro
1               5                   10                  15

Pro Pro Gly Thr Pro Phe Ala Val Leu His Arg Pro Gly Ala Gly His
                20                  25                  30

Pro Gly Thr Val Asp Val Val Ser Gly Pro Leu Arg Thr Ala Ala Thr
            35                  40                  45

Leu Ala Glu Leu Ser Leu Asp Asp Glu Ser Ala Pro Ala Ser Gln Gly
        50                  55                  60

Pro Gly Pro Ala His Arg Val Leu Ala Leu Val Pro His Arg Gln Ile
65                  70                  75                  80

Ala Glu Arg Gly Phe Ala Ala Pro Asp Asp Gly Thr Pro Leu Leu Ala
                85                  90                  95

Met Asp Ile Gly Thr Gln His Thr Val Pro Leu Glu Arg Met Leu Ala
            100                 105                 110

Leu Leu Pro Asp Arg Glu Leu His Val Glu Glu Thr Gly Phe Asp Leu
        115                 120                 125

Asp Asp Asp Arg Tyr Ala Ala Gly Val Asp Ala Leu Thr Arg Gln Glu
    130                 135                 140

Ile Gln Arg Gly Gln Gly Ala Asn Phe Val Leu Ala Arg Ser Leu His
145                 150                 155                 160

Gly Arg Ile Arg Asp Phe Asp Arg Thr Arg Ala Leu Ala Ala Leu Arg
                165                 170                 175

Arg Leu Leu Ile Ala Glu Ser Gly Ala Tyr Trp Thr Tyr Leu Val Cys
            180                 185                 190

Thr Gly Asp Arg Tyr Leu Ile Gly Ser Ser Pro Glu Gln His Val Arg
        195                 200                 205

Val Ala Gly Ser Arg Val Ser Met Asn Pro Ile Ser Gly Thr Tyr Arg
    210                 215                 220

Tyr Pro Glu Gly Gly Arg Pro Asp Arg Glu Ser Leu Leu Arg Phe Leu
225                 230                 235                 240

Ala Asp Pro Lys Glu Ile His Glu Leu Tyr Met Val Val Asp Glu Glu
                245                 250                 255

Leu Lys Met Met Thr Glu Leu Cys Gly Ser Arg Val Arg Val Ser Gly
            260                 265                 270

Pro Thr Leu Ala Trp Met Ser Arg Leu Ala His Thr Gln Tyr His Leu
        275                 280                 285

His Gly Glu Ser Pro Leu Pro Leu Thr Asp Ile Leu Arg Gly Thr Leu
    290                 295                 300

Pro Ala Pro Thr Val Thr Gly Ser Pro Val Glu Asn Ala Cys Arg Val
305                 310                 315                 320

Ile Ala Arg His Glu Pro Ala Gly Arg Gly Tyr Tyr Ser Gly Val Leu
                325                 330                 335

Ala Leu Ala Gly Gln Glu Gly Gly Arg Arg Ala Leu Asp Ala Val Ile
            340                 345                 350

Val Leu Arg Thr Ala Asp Ile Thr Ala Asp Gly Ser Val Arg Leu Thr
            355                 360                 365

Thr Gly Ala Thr Val Val Arg Asp Ser Val Pro Arg Glu Glu Ala Ala
    370                 375                 380

Glu Thr Thr Ala Lys Ala Ala Gly Leu Leu Thr Ala Leu Thr Arg Gly
385                 390                 395                 400

Pro Ala Gly Arg Ser Ala Ala Pro Ala His Ala Ala Pro Asp Val Ser
                405                 410                 415

Leu Gly Ala Asp Pro Ala Val Arg Ala Ala Leu Arg Ser Arg Asn Asp
            420                 425                 430

Gly Ile Ala Ala Phe Trp Leu Gly Gly Ala Arg Leu Pro Ala Pro
            435                 440                 445

Ser Pro His Gly Pro Arg Val Ala Val Ile Asp Ala Glu Asp Arg Phe
    450                 455                 460

Thr Ser Met Leu Ala Gln Gln Leu Arg Ala Val Gly Cys His Val Thr
465                 470                 475                 480

Leu His Pro Trp Trp Ser Val Pro Glu Ala Ala Asp Asp Pro Gly Thr
                485                 490                 495

Val Leu Leu Leu Gly Pro Gly Pro Gly Asp Pro Arg Asp Val Gly Asp
            500                 505                 510

Pro Arg Val Ala Arg Leu Arg Ser Leu Ala Gly Arg Arg Leu Ala Arg
    515                 520                 525

Arg Leu Pro Leu Ala Ala Val Cys Leu Gly His Gln Ala Val Cys Gly
530                 535                 540

Val Leu Gly Leu Pro Leu Val Arg Leu Ala Arg Pro Arg Gln Gly Ala
545                 550                 555                 560

Arg Met Arg Val Gly Leu Trp Gly Arg Asp Arg His Val Gly Phe Tyr
                565                 570                 575

Asn Ser Phe Thr Ala Arg Ser Asp Thr Asp Arg Cys Pro Leu Pro Gly
            580                 585                 590

Arg Asp Ala Thr Ala Arg Val Trp Arg Arg Asp Gly Gly Asp Val Val
    595                 600                 605

Ala Leu Asp Gly Pro Gly Leu Ala Thr Val Gln Phe His Ala Glu Ser
610                 615                 620

Leu Leu Thr Glu Asp Gly Pro Asp Ile Leu Arg Glu Leu Val Asp Arg
625                 630                 635                 640

Ala Ala Arg Thr Glu Arg Arg Thr Glu Ala Leu Met Ser Arg Arg Ala
                645                 650                 655

Lys Glu His Ala
            660

<210> SEQ ID NO 10
<211> LENGTH: 199
<212> TYPE: PRT
<213> ORGANISM: Streptomyces species FH6421

<400> SEQUENCE: 10

Val Asn Pro Pro Gly Thr Val Val Ala Asn Ala Ala Leu Asp Pro Arg
1               5                   10                  15

Glu Leu Arg Arg Thr Met Gly His Phe Ala Thr Gly Val Thr Val Leu
            20                  25                  30

Thr Cys Arg Arg Gly Ala Arg Leu His Gly Ala Thr Val Asn Ser Phe
        35                  40                  45

Thr Ser Val Ser Leu Asp Pro Pro Leu Ala Leu Val Ala Leu Asp Arg

```
                    50                  55                  60
Arg Thr Arg Ala Ala Ala Leu Leu Asp Asp Gly Pro Phe Val Val Asn
 65                  70                  75                  80

Leu Leu Gly Glu His Gln Gln Asp Leu Ala Leu His Phe Ala Gly Gly
                     85                  90                  95

Ser Pro Ala Asp Ser Val Pro Trp Val Asp Gly Asp Gly Asp Arg Pro
                    100                 105                 110

Arg Leu Ala Gly Thr Leu Gly His Leu Val Cys Arg Pro Trp Arg Thr
                115                 120                 125

Tyr Asp Gly Gly Asp His Thr Leu His Val Gly Arg Val Glu Glu Phe
            130                 135                 140

Ala Ala Gly Gly Gly Arg Pro Leu Leu Phe Tyr Arg Gly Val Phe Pro
145                 150                 155                 160

Arg Leu Met Pro Asp Gly Gly Asp Pro Glu Gly Pro Glu Glu Val
                165                 170                 175

Trp Ser Leu Cys Leu Asp Gly Pro Gly Pro Ala Thr Asp Gln Phe Val
            180                 185                 190

Thr Asp His Glu Thr Arg Lys
            195

<210> SEQ ID NO 11
<211> LENGTH: 523
<212> TYPE: PRT
<213> ORGANISM: Streptomyces species FH6421

<400> SEQUENCE: 11

Met Ala Pro Asp Asn Gly Gln Ser Ala Ala Pro Gly Thr Ser Gly Ala
  1               5                  10                  15

Ser Thr Gly Lys Ala Arg Val Thr Arg Pro Leu Thr Gly Asp Glu Tyr
                 20                  25                  30

Ile Glu Ser Ile Arg Asp Gly Arg Glu Ile Trp Ala Tyr Gly Glu Lys
             35                  40                  45

Val Asp Asp Val Thr Lys His Pro Ala Phe Arg Asn Thr Val Arg Met
 50                  55                  60

Thr Ala Arg Leu Tyr Asp Ala Leu His Asp Pro Glu His His Asp Thr
 65                  70                  75                  80

Leu Thr Ala Pro Thr Asp Thr Gly Ser Asp Gly Phe Thr His Lys Phe
                 85                  90                  95

Tyr Arg Val Pro Arg Ser Val Gln Asp Leu Val Gly Asp Arg Asp Ala
                100                 105                 110

Ile Ala Asp Trp Ala Arg Leu Thr Tyr Gly Trp Met Gly Arg Ser Pro
            115                 120                 125

Asp Tyr Lys Ala Ser Phe Leu Val Thr Leu Gly Ala Asn Pro Asp Tyr
130                 135                 140

Tyr Gly Asp Phe Ala Asp Asn Ala Arg Arg Trp Tyr Ala Thr Ala Gln
145                 150                 155                 160

Glu Asn Val Leu Phe Trp Asn His Ala Val Ile Asn Pro Pro Val Asp
                165                 170                 175

Arg His Arg Pro Ala Asp Glu Val Asp Asp Val Phe Val His Val Glu
            180                 185                 190

Lys Glu Cys Asp Asp Gly Leu Val Val Ser Gly Ala Lys Val Val Ala
            195                 200                 205

Thr Gly Ser Ala Leu Thr His Phe Asn Phe Val Ala His Tyr Gly Leu
210                 215                 220
```

```
Pro Val Lys Lys Lys Glu Phe Ala Leu Val Ala Thr Leu Pro Leu Ala
225                 230                 235                 240

Ala Pro Gly Val Lys Leu Ile Cys Arg Gln Ser Tyr Glu Leu Ala Ala
            245                 250                 255

Ser Arg Thr Gly Ser Pro Phe Asp Tyr Pro Leu Ser Ser Arg Leu Asp
        260                 265                 270

Glu Asn Asp Thr Ile Phe Ile Leu Asp Lys Val Lys Ile Pro Trp Glu
    275                 280                 285

Asn Val Leu Ile Tyr Gly Asp Thr Ala Arg Ala Gly Thr Phe Leu Gln
290                 295                 300

Thr Ser Gly Phe Thr His Arg Leu Thr Phe His Gly Val Thr Arg Leu
305                 310                 315                 320

Ala Val Lys Leu Asp Phe Leu Ala Gly Leu Leu Lys Gly Val Glu
                325                 330                 335

Val Thr Gly Thr Lys Asp Phe Arg Gly Ile Gln Thr Arg Val Gly Glu
            340                 345                 350

Val Leu Ala Trp Arg Asn Met Phe Trp Ala Leu Ser Asp Ala Met Ala
        355                 360                 365

His Asn Pro Asp Pro Trp His Asp Gly Ala Leu Leu Pro Asn Leu Asp
    370                 375                 380

Tyr Gly Met Ala Tyr Arg Trp Phe Met Thr Val Gly Tyr Pro Arg Val
385                 390                 395                 400

Arg Glu Ile Ile Met Gln Asp Leu Ser Ser Gly Leu Ile Tyr Leu Thr
                405                 410                 415

Ser His Ala Lys Asp Phe Asn Glu Pro Glu Leu Arg Pro His Leu Asp
            420                 425                 430

Arg Phe Met Arg Gly Ser Asn Gly Tyr Glu Ala Val Glu Arg Ala Lys
        435                 440                 445

Leu Met Lys Leu Ile Trp Asp Ser Val Gly Thr Glu Phe Ala Gly Arg
    450                 455                 460

His Glu Leu Tyr Glu Arg Asn Tyr Ser Gly Asn His Glu Ser Val Arg
465                 470                 475                 480

Ile Glu Leu Leu His Ala Gln Thr Ala Ser Gly Leu Val Asp Gln Tyr
                485                 490                 495

Arg Gly Phe Ala Glu Gln Cys Met Ala Glu Tyr Asp Leu Asp Gly Trp
            500                 505                 510

Thr Ala Pro Asp Leu Val Pro Asp Val Asp
        515                 520

<210> SEQ ID NO 12
<211> LENGTH: 222
<212> TYPE: PRT
<213> ORGANISM: Streptomyces species FH6421

<400> SEQUENCE: 12

Met Glu Gln Glu Arg Trp Asn Ser Val Asp Val Tyr Phe Ser Ser Leu
1               5                   10                  15

Leu Val Lys Glu Asp Glu Ala Leu Ser Lys Ala Ala Gln Ala His Arg
            20                  25                  30

Glu Phe Asp Leu Pro Asp Leu Ala Val Ser Ala Pro Gln Gly Lys Leu
        35                  40                  45

Leu His Leu Leu Ala Arg Leu Arg Gln Ala Arg Ile Leu Glu Ile
    50                  55                  60

Gly Thr Phe Gly Gly Tyr Ser Ser Ile Trp Leu Ala Arg Ala Leu Pro
65                  70                  75                  80
```

```
Pro Asp Gly Arg Leu Val Thr Ile Glu Trp Glu Arg Ser Phe Ala Glu
                85                  90                  95

Ser Ala Ala Ser Arg Leu Ala Glu Ala Gly Val Ala His Leu Val Glu
            100                 105                 110

Gln His Val Gly Arg Ala Leu Asp Ile Leu Pro Thr Leu Asp Arg Pro
        115                 120                 125

Gly Thr Ala Pro Phe Asp Met Val Phe Val Asp Ala Asn Lys Pro Asp
    130                 135                 140

Ile Pro Glu Tyr Phe Thr Trp Ala Leu Lys Leu Ser Arg Pro Gly Ala
145                 150                 155                 160

Val Val Val Val Asp Asn Val Leu Gly Gly Ala Val Thr Asp Pro
                165                 170                 175

Asp His Pro Asp Ala Gly Val Gln Gly Val Arg Arg Phe His Glu Met
            180                 185                 190

Leu Ala Gly Arg Ser Asp Val Thr Ala Thr Ser Ile Gln Thr Val Gly
        195                 200                 205

Thr Lys Gly Tyr Asp Gly Phe Thr Leu Ala Leu Val Thr Gly
    210                 215                 220

<210> SEQ ID NO 13
<211> LENGTH: 166
<212> TYPE: PRT
<213> ORGANISM: Streptomyces species FH6421

<400> SEQUENCE: 13

Met Arg Glu Asp Ser Ala Val Thr Thr Ala Ala Pro Pro Val His Leu
1               5                   10                  15

Val Pro Ala Met His His Leu Gly Val Gln Thr Arg Asp Leu Asp Asn
            20                  25                  30

Ser Leu Ala Trp Tyr Lys Asp Phe Phe Gly Cys Ala Glu Thr Trp Thr
        35                  40                  45

Leu Thr Thr Phe Ser Asp Leu Thr Arg Ser Arg Leu Pro Gly Ile Thr
    50                  55                  60

Arg Leu Thr Glu Ile Ser Val Ala Asp Val Arg Phe His Leu Phe Glu
65                  70                  75                  80

Arg Ala Gly His Asp Pro Ala Leu Pro Gly Gly Asn Lys Ala Gln Phe
                85                  90                  95

Gln His Val Cys Leu Ala Thr Gly Ser Pro Glu Glu Leu Arg Ala Trp
            100                 105                 110

Arg Asp Arg Trp Ile Glu Leu Tyr Arg Ser Gly Arg Tyr Asp Phe Ala
        115                 120                 125

Thr Asp Glu Gln Pro Thr Asp Ile Val Val Asp Ala Asp Gly Val His
    130                 135                 140

Ser Cys Tyr Leu Phe Asp Pro Asn Gly Leu Glu Phe Glu Phe Thr Tyr
145                 150                 155                 160

Val Pro Gly Gly Ala Ala
                165

<210> SEQ ID NO 14
<211> LENGTH: 268
<212> TYPE: PRT
<213> ORGANISM: Streptomyces species FH6421

<400> SEQUENCE: 14

Met Ser Ala Gly Pro His Arg Thr Val Thr Glu Leu Pro Val Ala Glu
1               5                   10                  15
```

```
Gly Trp Asp Phe Gly Asp Phe Pro Tyr Gly Leu Glu Pro Leu Thr Leu
             20                  25                  30

Pro Glu Pro His Glu Pro Ala Ala Asp Val Pro Asp Val Leu Cys
         35                  40                  45

Ala Glu Pro Ala Pro Gly Gly Ala Arg Thr Ser Cys Pro Arg Thr Gly
 50                  55                  60

Pro Ala Pro Gly Leu Pro Glu Leu Ala His Gln Leu Phe Trp Phe Arg
 65                  70                  75                  80

Trp Ile Thr Gly His Gln Leu Thr Phe Ala Ile Trp Gln Leu Leu Gly
             85                  90                  95

His Ala Leu His Gln Ala His Ala Arg Pro Asp Pro Gly Pro Ser Leu
             100                 105                 110

Arg Ala Met Thr Asp Leu Thr Arg Ala Tyr Thr Ala Met Leu Leu Tyr
             115                 120                 125

Thr Gly Ser Cys Pro Lys Asp Val Tyr Ser Asp Val Ile Arg Pro Ser
130                 135                 140

Met Phe Leu Gln His Arg Gly Phe Ser Gly Thr Trp Ala Pro Asp Phe
145                 150                 155                 160

Val Pro Val Arg Arg Leu Leu Arg Gly Arg Lys Thr Pro Trp His Glu
             165                 170                 175

Thr Pro Glu Gly Gly Arg Leu Ala Asp Glu Val Arg Leu Tyr His Leu
             180                 185                 190

Val His Ser Gly Val Ala Ala Lys Leu Val Pro Gly Gly Arg Ser Leu
             195                 200                 205

Leu Gln Asp Thr Ala Pro Thr Ala Arg Pro His Asp Pro Arg Met Gln
             210                 215                 220

Ala Leu Val Tyr Asp Asn Tyr Phe Leu Thr Leu Arg Ala Asp Val Pro
225                 230                 235                 240

Thr Ala Glu Val Val Glu Gln Leu Arg Arg Leu Ala Ala Val Arg
                 245                 250                 255

Leu Asp Val Ser Val Asn Gly Leu Tyr Pro Gly Leu
             260                 265

<210> SEQ ID NO 15
<211> LENGTH: 299
<212> TYPE: PRT
<213> ORGANISM: Streptomyces species FH6421

<400> SEQUENCE: 15

Val Arg Tyr Gly Val Val Leu Pro Glu Arg Arg Trp Ala Gln Ala
1               5                   10                  15

Arg Glu Gln Trp Val Arg Ala Glu Glu Phe Gly Phe Asp His Ala Trp
             20                  25                  30

Thr Tyr Asp Gln Leu Met Trp Arg Trp Leu Arg Asp Glu Pro Trp Phe
             35                  40                  45

Gly Ala Val Pro Thr Leu Ala Ala Ala Glu Ala Thr Ser Thr Leu
 50                  55                  60

Thr Val Gly Thr Met Val Ala Thr Pro Thr Tyr Arg His Pro Val Thr
 65                  70                  75                  80

Leu Ala Lys Glu Val Met Thr Leu Glu Asp Ile Ala Gly Gly Arg Phe
             85                  90                  95

Val Cys Gly Leu Gly Ala Gly Ala Gly Gly Leu Asp Asp Arg Val Val
             100                 105                 110

Asp Pro Ala Ala Tyr Ser Pro Arg Gln Arg Ala Asp Arg Phe Thr Glu
```

```
                    115                 120                 125
Phe Val Asp Leu Leu Asp Lys Leu Leu Ser Arg Arg Ser Thr Thr His
    130                 135                 140
Thr Gly Thr Tyr Tyr Asp Val Arg Glu Val Pro Val His Pro Gly Cys
145                 150                 155                 160
Leu Ala Thr Pro Arg Val Pro Phe Ala Ile Ala Thr Gly Pro Arg
                165                 170                 175
Gly Met Arg Leu Ala Ala Arg His Ala Asp Met Trp Ile Thr Ala Gly
                180                 185                 190
Arg Pro Gly Asp Phe Asp Ala Leu Pro Tyr Glu Glu Thr Leu Pro Val
                195                 200                 205
Ile Lys Glu Gln Leu Ala Arg Leu Asp Glu Ala Cys Glu Arg Thr Gly
    210                 215                 220
Arg Asp Pro Ala Thr Leu Arg Arg Leu Leu Thr Gly Ala Met Val
225                 230                 235                 240
Gly Gly Thr Leu Asp Ser Val Glu Ala Tyr Arg Asp Ala Ala Gly Arg
                245                 250                 255
Phe Gly Glu Leu Gly Ile Thr Asp Phe Val Val His Trp Pro Arg Pro
                260                 265                 270
Ser Phe Pro Tyr Gln Gly Arg Val Glu Val Leu Glu Gln Ile Ala Arg
                275                 280                 285
Asp Val Leu Thr Val Arg Gly Gly Glu Arg Pro
    290                 295

<210> SEQ ID NO 16
<211> LENGTH: 291
<212> TYPE: PRT
<213> ORGANISM: Streptomyces species FH6421

<400> SEQUENCE: 16

Val Ile Ala Tyr Glu Ile Val Asp Met Phe Thr Gly Thr Pro Phe Gln
1               5                   10                  15
Gly Cys Ala Leu Gly Val Val Pro Asp Ala Thr Ala Leu Asp Asp Asp
                20                  25                  30
Gly Met Arg Ala Val Ala Arg Glu Ile Gly Leu Thr Glu Thr Ala Phe
                35                  40                  45
Val Leu Pro Pro Glu Ser Pro Asp Ala Thr His Arg Val Arg Val Phe
    50                  55                  60
Thr Pro Glu Arg Glu Ser Pro Tyr Gly Gly His Ser Ala Ile Gly Thr
65                  70                  75                  80
Ala Thr Thr Leu Val Arg Leu Gly Arg Leu Arg Ala Gly Glu Leu Val
                85                  90                  95
Gln Glu Cys Gly Gly Arg Leu Met Thr Val Arg Ala Ser Ala Arg Arg
                100                 105                 110
Ala Thr Leu Gly Val Arg Gly Glu Pro Val Pro Pro Gly Ala Trp Asp
                115                 120                 125
Pro Val Pro Leu Leu Glu Ala Cys Gly Leu Thr Glu Asp Asp Leu Val
    130                 135                 140
Ala Gly Pro Arg Val Thr Gly Phe Gly Pro Ala Phe His Val Leu Pro
145                 150                 155                 160
Val Gly Pro Glu Ala Val Ala Arg Ala His Asp Pro Ala His Pro
                165                 170                 175
Val Trp Ser Thr Cys Pro Asp Ala Val Val Val Ala Tyr Asp Arg Arg
                180                 185                 190
```

```
Gly His Leu Ala Asp Val Arg Val Phe Ala Pro Gly Tyr Gly Met Pro
            195                 200                 205

Glu Asp Pro Ala Cys Ala Ser Ala Ala Leu Ala Leu Gly Ala Trp Leu
            210                 215                 220

Thr Gly Ala Gly Leu Val Pro Ala Thr Asp Gly Thr Arg Leu Tyr Arg
225                 230                 235                 240

Val Arg Gln Gly His Gly Leu Gly Arg Pro Ala Arg Leu Asp Cys Ala
                245                 250                 255

Val Thr Val Arg Asp Gly Arg Ala Val Ala Ala Glu Val Thr Gly Glu
                260                 265                 270

Val Ala Ala Thr Ala Ala Gly Arg Met His Leu Pro Arg Thr Ala Ala
                275                 280                 285

Val Ala Arg
    290

<210> SEQ ID NO 17
<211> LENGTH: 597
<212> TYPE: PRT
<213> ORGANISM: Streptomyces species FH6421

<400> SEQUENCE: 17

Val Leu Phe Arg Pro Glu Leu Arg Gly Thr Arg Gly Ala Val Ala Ser
1               5                   10                  15

Thr His Trp Leu Ala Ser Ala Ala Gly Phe Arg Met Tyr Asp Lys Gly
                20                  25                  30

Gly Asn Ala Phe Asp Ala Ala Val Ala Ala Phe Val Ile Gln Val
                35                  40                  45

Val Glu Pro His Leu Asn Gly Pro Gly Gly Asp Val Pro Val Leu Val
    50                  55                  60

His Arg Ala Gly Ser Gly Arg Val Asp Val Val Cys Gly Gln Gly Pro
65                  70                  75                  80

Met Pro Arg Ala Ala Thr Ile Glu Arg Phe Glu Gln Leu Gly Leu Ser
                85                  90                  95

Val Val Pro Gly Ser Gly Leu Leu Pro Ala Val Val Pro Gly Ala Phe
                100                 105                 110

Gly Ala Trp Leu Arg Val Leu Ala Glu Tyr Gly Thr Leu Arg Leu Glu
            115                 120                 125

Asp Val Leu Glu Pro Ala Ile Gly Tyr Ala Glu Arg Gly Tyr Pro Leu
            130                 135                 140

Leu Pro Lys Ala Ala Ala Met Ile Glu Ala Leu Gln Glu Leu Phe Arg
145                 150                 155                 160

Asp Glu Trp Thr Glu Ser Ala Arg Thr Tyr Leu Val Gly Gly Ala Ala
                165                 170                 175

Pro Arg Pro Gly Gln Arg Met Thr Asn Pro Asp Leu Ala Arg Thr Tyr
            180                 185                 190

Arg Arg Val Leu Asp Glu Ala Arg Ala Ala Gly Ala Asp Arg Asp Lys
            195                 200                 205

Gln Ile Asp Ala Ala Leu Arg Ala Phe Tyr Glu Gly Phe Val Ala Glu
            210                 215                 220

Ala Ile Asp Gly Tyr Leu Ala Lys Ala Glu Glu Ile Asp Ala Thr Gly
225                 230                 235                 240

Arg Arg His Arg Gly Leu Leu Thr Gly Ala Asp Leu Ala Gly Trp Arg
                245                 250                 255

Ala Thr Val Glu Pro Ser Leu Ser Phe Asp His Arg Gly Leu Thr Val
                260                 265                 270
```

His Lys Ala Gly Pro Trp Ser Gln Gly Pro Val Phe Leu Gln Leu
        275                 280                 285

Ala Leu Leu Arg Glu Phe Asp Leu Ala Gly Met Gly Pro His Ser Ala
    290                 295                 300

Glu Phe Val His Thr Val Thr Glu Ala Ala Lys Leu Ala Phe Ala Asp
305                 310                 315                 320

Arg Glu Ala Trp Tyr Gly Asp Pro Ala His Ala Glu Val Pro Val Gly
                325                 330                 335

Asp Leu Leu Asp Pro Ala Tyr Thr Ala Ala Arg Arg Glu Leu Ile Gly
                340                 345                 350

Ser Glu Ala Ser Thr Glu Leu Arg Pro Gly Ser Pro Gly Gly Arg Thr
            355                 360                 365

Pro Val Leu Pro Pro Val His Asp Glu Ser Ala Gly Pro Ala Gly Pro
    370                 375                 380

Ser Trp Leu Gly Glu Leu Glu Glu Gly Ile Pro Ala Val Val Arg Ser
385                 390                 395                 400

Thr Ala Ala Arg Gly Asp Thr Cys Cys Val Thr Ala Thr Asp Ala His
                405                 410                 415

Gly Asn Met Val Val Ala Thr Pro Ser Gly Gly Trp Leu Lys Ser Ser
                420                 425                 430

Pro Val Val Pro Gly Leu Gly Phe Pro Leu Gly Thr Arg Gly Gln Met
            435                 440                 445

Ala Thr Leu Thr Arg Gly His Ala Asn Ala Leu Ala Pro Gly Lys Arg
    450                 455                 460

Pro Arg Thr Thr Leu Ser Pro Thr Leu Val Leu Arg Glu Gly Arg Pro
465                 470                 475                 480

Ala Leu Ala Phe Gly Thr Pro Gly Gly Asp Gln Gln Asp Gln Trp Thr
                485                 490                 495

Leu Gln Phe Phe Leu Arg His Thr Glu His Gly Met Gly Leu Gln Glu
                500                 505                 510

Ala Val Glu Ala Arg Thr Phe His Thr Asp His Val Pro Thr Ser Phe
    515                 520                 525

Thr Pro Arg Arg Phe Ala Pro Gly Thr Val Thr Val Glu Ser Gly Met
    530                 535                 540

Pro Glu Glu Thr Ile Gln Glu Leu Arg Arg Gly His Gln Val Arg
545                 550                 555                 560

Thr Val Ala Asp Tyr Ser Leu Ser Lys Val Cys Val Thr Gly Leu Ala
                565                 570                 575

Ser Asp Asp Met Val Ile Ala Ala Ser Pro Arg Gly Ala Gln Ala
            580                 585                 590

Tyr Ala Val Ala Asp
        595

<210> SEQ ID NO 18
<211> LENGTH: 769
<212> TYPE: PRT
<213> ORGANISM: Streptomyces species FH6421

<400> SEQUENCE: 18

Met Glu Gly Glu Arg Met Val Pro His Pro Ser Leu Asp Pro Gly Asp
1               5                   10                  15

His Ile Val Leu Gly Glu Ala Arg Gln Asn Asn Leu Lys Gly Val Ser
            20                  25                  30

Leu Arg Ile Pro Lys Gly Arg Leu Thr Val Phe Thr Gly Val Ser Gly

-continued

```
                35                  40                  45
Ser Gly Lys Ser Ser Leu Val Phe Gly Thr Ile Ala Val Glu Ser Gln
 50                  55                  60

Arg Gln Met Asn Glu Thr Tyr Pro Ala Phe Ile Arg Asn Arg Leu Pro
 65                  70                  75                  80

Lys Phe Glu Arg Pro Asp Ala Glu Val Ile Glu Asn Leu Ser Thr Ala
                 85                  90                  95

Ile Val Ile Asp Gln Arg Pro Val Gly Asn Ala Arg Ser Thr Val
                100                 105                 110

Gly Thr Met Thr Glu Ile His Ala Met Leu Arg Val Leu Phe Ser Arg
                115                 120                 125

His Gly Arg Pro Ser Ala Gly Pro Ser His Met Tyr Ser Phe Asn Asp
                130                 135                 140

Pro Arg Gly Met Cys Pro Glu Cys Glu Gly Leu Gly Ser Arg Val Arg
145                 150                 155                 160

Leu Asp Leu Asn Arg Leu Leu Asp Glu Asp Lys Ser Leu Asn Glu Gly
                165                 170                 175

Ala Ile Arg Phe Gln Pro Phe Ala Val Gly Thr Phe Pro Trp Gln Leu
                180                 185                 190

Tyr Ala Glu Ser Gly Leu Phe Asp Pro Asp Leu Pro Leu Arg Glu Phe
                195                 200                 205

Ser Ala Asp Asp Arg Glu Leu Leu His Gly Ser Gly Phe Lys Val
210                 215                 220

Asp Arg Ala Gly Arg His Gly Val Tyr Lys Asn Glu Tyr Glu Gly Ile
225                 230                 235                 240

Val Leu Arg Phe Thr Arg Arg Tyr Leu Lys Ala Gly Leu Asp Thr Leu
                245                 250                 255

Lys Pro Lys Glu Arg Ala Ala Val Gln Glu Val Val Thr Glu Gly Pro
                260                 265                 270

Cys Glu Ala Cys Gly Gly Ala Arg Leu Gly Pro Ala Ala Leu Ala Ser
                275                 280                 285

Arg Ile Ala Gly Glu Asn Ile Ala Asp Tyr Ser Ala Leu Glu Val Thr
290                 295                 300

Asp Leu Ile Gly Arg Leu Glu Arg Asn Asp Ala Pro Pro Val Lys Pro
305                 310                 315                 320

Val Val Gln Ala Ala Leu Ala Ala Leu Arg Arg Ile Glu Ala Val Gly
                325                 330                 335

Leu Gly Tyr Leu Ser Leu Asp Arg Gln Thr Ala Thr Leu Ser Gly Gly
                340                 345                 350

Glu Ala Gln Arg Leu Lys Thr Val Arg His Leu Gly Ser Ser Leu Thr
                355                 360                 365

Gly Leu Thr Tyr Ile Phe Asp Glu Pro Ser Val Gly Leu His Pro Arg
                370                 375                 380

Asp Val Arg Arg Leu Asn Glu Leu Leu Ala Leu Arg Asp Lys Gly
385                 390                 395                 400

Asn Thr Val Leu Val Val Glu His Asp Arg Asp Val Ile Ala Ile Ala
                405                 410                 415

Asp His Val Val Asp Met Gly Pro Gly Ala Gly Ser Gln Gly Gly Glu
                420                 425                 430

Val Val Tyr Glu Gly Ser Pro Thr Gly Leu Arg Gly Ser Asp Ser Pro
                435                 440                 445

Thr Gly Arg Gly Leu Arg Ser Val Pro Gly Leu Lys Arg Arg Leu Arg
450                 455                 460
```

```
Ala Pro Asp Gly Arg Leu Thr Val Arg Gly Ala Arg Leu His Asn Leu
465                 470                 475                 480

Lys Asp Val Thr Val Asp Val Pro Thr Gly Val Leu Val Ala Leu Ser
            485                 490                 495

Gly Val Ala Gly Ser Gly Lys Ser Ser Leu Ala Arg Glu Leu Ala Ala
            500                 505                 510

Arg His Pro Glu Glu Thr Val Val Asp Gln Ser Ser Ile Gly Ile
            515                 520                 525

Ser Ser Arg Ser Thr Pro Ala Thr Tyr Thr Asp Ile Met Asp Thr Val
            530                 535                 540

Arg Arg Leu Phe Ala Arg Ala Ser Gly Thr Asp Pro Gly Leu Phe Ser
545                 550                 555                 560

Phe Asn Ser Ala Gly Ala Cys Pro Glu Cys Gln Gly Arg Gly Val Ile
            565                 570                 575

Glu Thr Asp Leu Ala Phe Met Asp Pro Val Thr Thr Val Cys Glu Arg
            580                 585                 590

Cys Glu Gly Arg Arg Phe Asn Asp Glu Ala Leu Ser His Thr Leu Ser
            595                 600                 605

Gly Arg Asn Ile Ala Asp Val Leu Ala Met Thr Ala Glu Glu Ala Ile
            610                 615                 620

Gly Phe Phe Ala Glu Asp Ser Val Arg Arg Lys Leu Ala Leu Leu Thr
625                 630                 635                 640

Glu Val Gly Leu Gly Tyr Leu Thr Leu Gly Arg Ser Leu Ser Thr Leu
            645                 650                 655

Ser Gly Gly Glu Arg Gln Arg Leu Lys Leu Ala His Arg Leu His Ala
            660                 665                 670

Ser Gly Ser Val Tyr Ile Phe Asp Glu Pro Ser Thr Gly Leu His Met
            675                 680                 685

Thr Asp Val Gly Lys Leu Leu Thr Leu Phe Asp Arg Leu Val Asp Gly
690                 695                 700

Gly Asn Thr Val Val Ile Glu His Asp Leu Asp Val Leu Lys Tyr
705                 710                 715                 720

Ala Asp Trp Ile Ile Asp Leu Gly Pro Glu Ala Gly Arg His Gly Gly
            725                 730                 735

Arg Val Val Phe Glu Gly Thr Pro Ala Asp Leu Ala Arg Val Arg Glu
            740                 745                 750

Ser His Thr Gly Arg Cys Leu Ala Glu Asp Leu Ala Ala His Gly His
            755                 760                 765

Leu
```

<210> SEQ ID NO 19
<211> LENGTH: 67
<212> TYPE: PRT
<213> ORGANISM: Streptomyces species FH 6421

<400> SEQUENCE: 19

```
Met Pro Leu Ile His Val Thr Leu Leu Ser Gly Arg Gly Glu Glu
1               5                   10                  15

Ile Ala Ala Leu Gly Arg Ala Val Thr Glu Ala Val His Thr Thr Leu
            20                  25                  30

Gly Thr Pro Arg Glu Ala Ile Arg Val Thr Val Asp Ala Cys Pro Pro
            35                  40                  45

Glu His Trp Phe Val Gly Gly Val Ser Met Ala Glu Lys Lys Ala Ala
    50                  55                  60
```

Arg Gly Gly
65

<210> SEQ ID NO 20
<211> LENGTH: 400
<212> TYPE: PRT
<213> ORGANISM: Streptomyces species FH6421

<400> SEQUENCE: 20

Leu His Val His Pro Ser Leu Ser Glu Pro Gln Arg Gly Val Met Arg
1               5                   10                  15

Ile Ala Val Ile Gly Ala Gly Pro Gly Gly Leu Tyr Thr Ala Cys Leu
            20                  25                  30

Val Lys Arg Leu Arg Pro His Asp Val Val Glu Val Trp Glu Ala Asn
        35                  40                  45

Ala Ala His Asp Thr Phe Gly Phe Gly Val Val Phe Ser Asp Gly Ala
    50                  55                  60

Leu Gly Gly Ile Glu Ala Ala Asp Pro Ala Leu Phe Glu Ala Val Glu
65                  70                  75                  80

Ala Glu Phe Ala Arg Trp Thr Arg Ile Asp Val Cys Tyr Arg Gly Arg
                85                  90                  95

Val Gln Arg Asn Glu Gly Tyr Gly Phe Ala Ala Ile Gly Arg His Thr
            100                 105                 110

Leu Leu Arg Leu Leu Gln Glu Arg Cys Ala Asp Leu Gly Val Arg Leu
        115                 120                 125

His Phe Gly Ser Pro Ala Pro Glu Val Ser Arg Leu Arg Ala Ser His
    130                 135                 140

Asp Leu Val Val Ala Ala Asp Gly Val Gly Ser Arg Thr Arg Ala Arg
145                 150                 155                 160

Tyr Glu Ala Ala Phe Gly Thr Glu Arg Glu Gln Ala Gly Ser Arg Tyr
                165                 170                 175

Met Trp Leu Gly Thr Asp Arg Pro Phe Asp Ala Leu Thr Phe Ala Val
            180                 185                 190

Val Glu Thr Asp His Gly Pro Val Gln Ala His Ala Tyr Pro Tyr Ala
        195                 200                 205

Pro Gly Arg Ser Thr Phe Ile Val Glu Ile Gly Asp Ala Val Trp Arg
    210                 215                 220

Ala Ala Gly Phe Arg Ala Ala Glu Arg Arg Ser Asp Asp Pro Val Gly
225                 230                 235                 240

Asp Arg Glu Ser Ile Gly Arg Val Arg Glu Tyr Phe Thr Gly Leu Leu
                245                 250                 255

Asp Gly His Gly Leu Trp Gly Asn Arg Ser Tyr Trp Gly Arg Phe Ala
            260                 265                 270

Ala Val Arg Asn Arg Asp Trp Ser His Gly Asn Leu Val Leu Leu Gly
        275                 280                 285

Asp Ser Ala His Thr Thr His Phe Ser Ile Gly Ser Gly Thr Lys Leu
    290                 295                 300

Ala Met Glu Asp Gly Leu Ser Leu Ala Thr Ala Leu His Asp His Gly
305                 310                 315                 320

Thr Val Pro Glu Ala Leu Ala Ala Tyr Glu Ala Glu Arg Arg Pro Ala
                325                 330                 335

Val Glu Arg Met Gln Arg Thr Ala Leu Thr Ser Leu Glu Trp Phe Glu
            340                 345                 350

Asn Ile Asp Arg Cys Val Gly Leu Ala Pro Glu Ala Phe Asn Ala His

```
                  355                 360                 365
Leu Leu Thr Arg Ser Gly Arg Leu Thr Arg Asp Asp Leu Pro Ala Val
    370                 375                 380
Asp Pro Glu His Val Gly Arg Ile Arg Arg Phe Ala Asp Ala Ala
385                 390                 395                 400

<210> SEQ ID NO 21
<211> LENGTH: 804
<212> TYPE: PRT
<213> ORGANISM: Streptomyces species FH6421

<400> SEQUENCE: 21

Met Pro Asp Val Leu Thr Pro Thr Pro Leu Pro Ala Ala Asp Leu Ala
1               5                   10                  15
Gly Leu Phe Arg Ala Leu Asp Pro Pro Phe Ala Leu Val Arg Arg
            20                  25                  30
Ala Ala Pro Asp Gly Thr Ser Thr Gly Pro Phe Asp Val Phe Ile Gly
        35                  40                  45
Thr Met Asp Thr Val Arg Arg Val Thr Asp Leu Pro Ser Gly Pro Ala
    50                  55                  60
Val Pro Gly Gly Pro His Thr Leu Ala Leu Leu Pro Tyr Arg Cys
65                  70                  75                  80
Leu Ala Glu Arg Gly Leu Asp Cys His Asp Asp Gly Thr Pro Leu Arg
                85                  90                  95
Val Leu Arg Ile Arg Arg Arg His Thr Ala Asp His Ala Ala Leu Thr
            100                 105                 110
Ala Ala Leu Ala Ala Val Arg Pro Ala Gly Asp Leu Leu Gly Glu Gly
        115                 120                 125
Ala Gly Phe Asp Gly Ser Asp Glu Asp Tyr Ala Asp Leu Val Arg Asp
    130                 135                 140
Leu Met Ala Asp Glu Val Ala Arg Thr Gly Leu His Val Leu Ile Arg
145                 150                 155                 160
Arg Asp Phe Thr Ala Arg Leu Pro Gly His Gly Pro Val Val Gly
                165                 170                 175
Glu Leu Phe Arg Arg Leu Leu Ala Val Glu His Gly Ala Tyr Trp Thr
            180                 185                 190
Phe Ala Val Tyr Thr Gly Gly Pro Asp Gly Ala Ala Leu Ala Gly Ala
        195                 200                 205
Ser Pro Gln Gly His Val Thr Leu Arg Asn Gly Arg Val Val Met Arg
    210                 215                 220
Pro Met Cys Gly Thr Leu Arg Leu Pro Pro Gly Gly Arg Pro Ser Ala
225                 230                 235                 240
Ala Asp Leu Val Ala Phe Leu Arg Asp Gly Lys Glu Ser Glu Glu Leu
                245                 250                 255
Gly Ala Val Val Asp Ala Glu Leu Ala Met Leu Cys Arg Ile Ser Glu
            260                 265                 270
Gly Asp Val Arg Leu Glu Gly Pro Arg Leu Arg Pro Met Ala Arg Val
        275                 280                 285
Leu His Thr Glu Cys Arg Ile Ser Ala Thr Ala Ala Leu Pro Ala Arg
    290                 295                 300
His Thr Leu Ala Gly Ser Leu Phe Ala Ala Thr Ala Val Gly Arg Pro
305                 310                 315                 320
Phe Ala Asp Ala Cys Arg Val Ile Thr Arg Arg Glu Pro Thr Gly Arg
                325                 330                 335
```

```
Gly Tyr Tyr Gly Gly Leu Ile Ala Leu Leu Gly His Asp Asp Ala Gly
                340                 345                 350

Asn Glu Glu Leu Asp Thr Ala Val Leu Ile Arg Thr Phe Glu Val Ser
        355                 360                 365

Gly Gln Gly Arg Leu Lys Leu Ser Val Gly Ala Thr Leu Gly Pro Arg
    370                 375                 380

Ser Val Ala Ala Asp Glu Thr Ala Glu Thr Arg Ala Lys Ala Ser Ala
385                 390                 395                 400

Leu Val Ser Ala Leu Ala Ser Gly Gly Pro Thr Ala Glu Gly Gly Ala
                405                 410                 415

Gly Arg His Ala Arg Ala Gly Leu Gly Arg Gly Pro Glu Ala Ala Gly
            420                 425                 430

Gly Pro Ala Thr Gly Glu Arg Ser Gly Val Pro Gly Asp Arg Thr Arg
            435                 440                 445

His Gln Gln Ala Ala Gly Arg Gln Pro Thr Ser Pro Ala Asp Pro Ala
        450                 455                 460

Trp Arg Pro Ser Val Thr Ala Glu Gly Ala Gly Asp His Ala Arg
465                 470                 475                 480

Ala Gly Leu Gly Arg Gly Pro Glu Ala Ala Gly Gly Pro Ala Thr Gly
                485                 490                 495

Glu Gly Gly Gly Val Pro Gly Asp Arg Thr Arg His Gln Gln Ala Ala
                500                 505                 510

Gly Arg Gln Pro Thr Ser Pro Ala Asp Pro Ala Trp Arg Pro Ser Val
            515                 520                 525

Thr Ala Glu Gly Ala Gly Gly His Ala Arg Ala Gly Leu Gly Arg
        530                 535                 540

Gly Pro Glu Ala Ala Gly Gly Pro Ala Thr Gly Glu Gly Gly Gly Val
545                 550                 555                 560

Pro Gly Asp Arg Thr Arg His Gln Gln Ala Ala Gly Arg Arg Pro Thr
                565                 570                 575

Ser Ser Ala Asp Pro Ala Trp Cys Pro Ser Val Thr Ala Glu Leu Asp
            580                 585                 590

Arg Arg Arg Ala Arg Leu Ser Ala Tyr Trp Gln Arg Pro Arg Arg Pro
        595                 600                 605

Gly Ser Arg Pro Ala Pro Arg Pro Val Leu Leu Val Asp Thr Gly
    610                 615                 620

Gly Glu Glu Thr Ala Pro Leu Ala Ala Met Leu Arg Gly Leu Gly Arg
625                 630                 635                 640

Thr Val Asp Val Arg Pro Ala Tyr Pro Ala Ala Ala Pro Arg Thr
                645                 650                 655

Val Ala Pro Gly Thr Thr Val Val Leu Gly Pro Gly Pro Gly Asp Pro
            660                 665                 670

Leu Ala His Gly Asp Asp Arg Ile Thr Ala Leu Arg Ala Met Thr Ser
        675                 680                 685

Ala Leu Leu Ser Ser Gly Ala Pro Thr Phe Gly Val Gly Leu Gly Phe
    690                 695                 700

His Leu Leu Leu Ala Val Leu Gly Leu Ala Gly Ala Ala Arg Ala Trp
705                 710                 715                 720

Asp Gly Ala Thr Gly Gln Arg Glu Ile Glu Val Phe Gly Arg Arg Ala
                725                 730                 735

Thr Val Gly Tyr Gly Gly Thr His Thr Val Val Ala Gly Pro His Thr
            740                 745                 750

Asp Thr Leu Ala Arg Arg Leu Ser Leu Thr Leu Cys Tyr Gly Pro Ala
```

```
              755                 760                 765
His Gly Glu Leu Val Ala Met Arg Gly Pro Arg Thr Gly Val Ala
    770                 775                 780

Phe Leu Pro Ala Ser Val Leu Ser Val Glu Gly Ala Glu Leu Leu Asp
785                 790                 795                 800

Leu Leu Leu Pro

<210> SEQ ID NO 22
<211> LENGTH: 481
<212> TYPE: PRT
<213> ORGANISM: Streptomyces species FH6421

<400> SEQUENCE: 22

Met Ala Glu Val Thr Gln Thr Asp Val Arg Arg Glu Phe Asp Arg Gly
1               5                   10                  15

Met Pro Gly Leu Arg Val Pro Gly Arg Val Val Ile Gly Ala Gly
            20                  25                  30

Leu Ser Gly Leu Ala Val Ala Tyr Glu Leu Ala Arg Arg Gly Thr Asp
        35                  40                  45

Val Thr Val Leu Glu Ala Ser Asn Arg Pro Gly Gly Arg Ala Tyr Thr
    50                  55                  60

Leu Arg Glu Pro Phe Thr Asp Gly Leu Tyr Ala Glu Ala Gly Ala Met
65                  70                  75                  80

Thr Leu Thr Pro His Cys His Tyr Ala Met His Tyr Leu Arg Glu Leu
                85                  90                  95

Gly Val Glu Leu Glu Thr Ala Asp Leu Val Gly Ser Gln Phe Ser Tyr
            100                 105                 110

Phe Val Gly Asn Arg Phe Phe Gly Pro Asp Ala Asp Ser Leu Asp Arg
        115                 120                 125

Ala Gly Leu Pro Leu Ala Pro His Glu Lys Gly Leu Ser Val Thr Asp
    130                 135                 140

Met Ile Asp Arg Tyr Val Arg Ala Tyr Glu Ala Leu Glu Pro Asp
145                 150                 155                 160

Ile Thr Ala Ala Asp Trp Ala Pro Thr Pro Leu Leu Glu Pro Tyr Asp
                165                 170                 175

Arg Arg Ser Val Tyr Glu Val Leu Ser Gly Arg Gly Ala Ser Pro Ala
            180                 185                 190

Ala Ile Asp Leu Val Glu Pro His Phe Leu Glu Met Arg Gly Gly Asp
        195                 200                 205

Leu Lys Thr Ala Ser Ala Leu Ser Trp Leu Arg His Glu Ser Ser Pro
    210                 215                 220

His Ser Leu Ala Asn Ala Asp Pro Arg Trp Ser Lys Val Lys Gly Gly
225                 230                 235                 240

Thr Asp Arg Phe Pro Arg Ala Phe Ala Glu Arg Leu Lys Asp Arg Ile
                245                 250                 255

Arg Tyr Arg Ala Pro Val Val Arg Val Ala Gln Asp Asp Glu Gly Ala
            260                 265                 270

Arg Val Thr Phe Leu Asp Gly Thr Arg Met Arg Ser Val Asp Ala Asp
        275                 280                 285

Arg Val Val Thr Val Pro Phe Ser Ala Ile Arg His Ile Asp Phe
    290                 295                 300

Thr Asp Ala Gly Leu Ser Asp Ala Lys Gln Ala Val Met Arg Arg Val
305                 310                 315                 320

Lys Tyr Ser Ser Ile Val Arg Val Tyr Leu Gln Met Arg Arg Arg Phe
```

-continued

```
                    325                 330                 335
Trp Ala Gln Asp Asn Ala Ser Phe Ser Thr Asp Leu Pro Val Arg Trp
            340                 345                 350

Val Arg Asp Ala Thr Pro Arg Leu Pro Gly Pro Arg Lys Ile Leu Glu
            355                 360                 365

Cys Leu Ile Thr Gly Trp Arg Ala Arg Ala Leu Ala Val Leu Ser Pro
        370                 375                 380

Glu Glu Arg Ile Arg Phe Ala Leu Glu His Val Glu Ser Met Leu Pro
385                 390                 395                 400

Gly Ala Arg Glu His Phe Glu Thr Gly Thr Ser Val Val Trp Asp Gln
                405                 410                 415

Gln Pro Tyr Ile Glu Gly Ala Tyr Ile Leu Pro Glu Met Gly His Ser
                420                 425                 430

Ser Leu Met Pro Ala Met Arg Arg Pro Glu Gly Arg Ile His Phe Ala
            435                 440                 445

Gly Asp His Thr Ser Phe Glu Pro Asn Gly Gly Ser Met Thr Leu Ala
        450                 455                 460

Leu Glu Ser Ala Ala Arg Thr Val Leu Glu Leu Gly Gly Thr Ala Asn
465                 470                 475                 480

Gly
```